(12) United States Patent
Kesteleyn et al.

(10) Patent No.: US 7,608,726 B2
(45) Date of Patent: Oct. 27, 2009

(54) SUBSTITUTED INDOLEPYRIDINIUM AS ANTI-INFECTIVE COMPOUNDS

(75) Inventors: Bart Rudolf Romanie Kesteleyn, Berlare (BE); Wim Van De Vreken, Beveren (BE); Natalie Maria Francisca Kindermans, Mechelen (BE); Maxime Francis Jean-Marie Ghislain Canard, La Hulpe (BE); Kurt Hertogs, Antwerp (BE); Eva Bettens, Zoersel (BE); Veronique Corine Paul De Vroey, Boechout (BE); Dirk Edward Désiré Jochmans, Herent (BE)

(73) Assignee: Tibotec Pharmaceuticals Ltd., Little Island, Co. Cork (IE)

( * ) Notice: Subject to any disclaimer, the term of this patent is extended or adjusted under 35 U.S.C. 154(b) by 505 days.

(21) Appl. No.: 10/535,007

(22) PCT Filed: Nov. 14, 2003

(86) PCT No.: PCT/EP03/50837

§ 371 (c)(1),
(2), (4) Date: May 12, 2005

(87) PCT Pub. No.: WO2004/046143

PCT Pub. Date: Mar. 6, 2004

(65) Prior Publication Data

US 2006/0173000 A1 Aug. 3, 2006

(30) Foreign Application Priority Data

Nov. 15, 2002 (EP) .................. 02079783

(51) Int. Cl.
*C07D 491/00* (2006.01)
(52) U.S. Cl. .................. 549/81; 549/84
(58) Field of Classification Search .................. 546/81, 546/84
See application file for complete search history.

(56) References Cited

FOREIGN PATENT DOCUMENTS

WO WO 02/055520 A2 7/2002
WO WO 02/059123 A2 8/2002

OTHER PUBLICATIONS

Ryabova et al. Russian Chemical Bulletin, International Edition, 2001 (50), 1449-1456. p. 1449, formula 1.*
Latsetti et al. STN Accession No. 2002:483896;Document No. 137:352993 Abstract of Russian chemical Bulletin (Translation of Izvestiya Akademii Nauk, Seriya Khimicheskaya) (2002) 51(3), 506-512.*
International Search Report dated Apr. 30, 2004 for related International Application No. PCT/EP2003/050837.

* cited by examiner

*Primary Examiner*—D. Margaret Seaman
*Assistant Examiner*—Nizal S Chandrakumar

(57) ABSTRACT

The present invention concerns the compounds of formula (I)

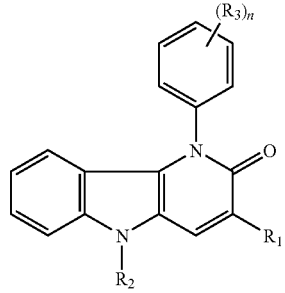

Figure 1:
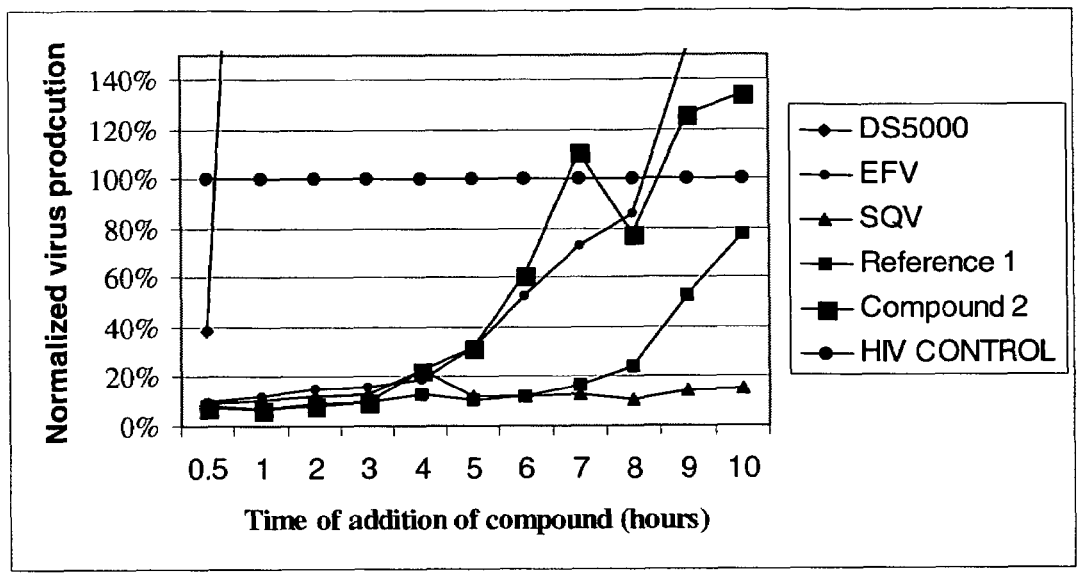

their N-oxides, salts, stereoisomeric forms, racemic mixtures, prodrugs, esters and metabolites, wherein n is 1, 2 or 3; $R_1$ is H, CN, halo, aminoC(=O), C(=O)OH, $C_{1-4}$alkyloxyC(=O), $C_{1-4}$alkylC(=O), mono- or di($C_{1-4}$alkyl)aminoC(=O), arylaminoC(=O), N-(aryl)-N—($C_{1-4}$alkyl)aminoC(=O), methanimidamidyl, N-hydroxy-methanimidamidyl, mono- or di($C_{1-4}$alkyl)methanimidamidyl, $Het_1$ or $Het_2$; $R_2$ is H, $C_{1-10}$alkyl, $C_{2-10}$alkenyl, $C_{3-7}$cycloalkyl, wherein said $C_{1-10}$alkyl, $C_{2-10}$alkenyl and $C_{3-7}$cycloalkyl may be optionally substituted; $R_3$ is nitro, cyano, amino, halo, hydroxy, $C_{1-4}$alkyloxy, hydroxyC(=O), aminoC(=O), $C_{1-4}$alkyloxyC(=O), mono- or di($C_{1-4}$alkyl)aminoC(=O), $C_{1-4}$alkylC(=O), methanimidamidyl, mono- or di($C_{1-4}$alkyl)methanimidamidyl, N-hydroxy-methanimidamidyl or $Het_1$; for use as a medicine. The invention further relates to a novel subgroup of the compounds of formula (I), and to compositions comprising compounds of formula (I).

17 Claims, 1 Drawing Sheet

SUBSTITUTED INDOLEPYRIDINIUM AS ANTI-INFECTIVE COMPOUNDS

The present invention relates to the use of substituted indolepyridinium as anti-infective compounds, and to pharmaceutical compositions and diagnostic kits comprising them. The present invention also concerns combinations of the present substituted indolepyridinium compounds with another anti-retroviral agent. It further relates to their use in assays as reference compounds or as reagents.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

AIDS patients are currently treated with HIV protease inhibitors (PIs), nucleoside reverse transcriptase inhibitors (NRTIs), non-nucleoside reverse transcriptase inhibitors (NNRTIs) and nucleotide reverse transcriptase inhibitors (NtRTIs). Those compounds are often administered in drug cocktails comprising two or more compounds of the above classes of drugs. Despite the fact that these antiretrovirals are very useful, they have a common limitation, namely, the targeted enzymes in the HIV virus are able to mutate in such a way that the known drugs become less effective, or even ineffective against these mutant HIV viruses. Or, in other words, the HIV virus creates an ever-increasing resistance against the available drugs.

Resistance of retroviruses, and in particular the HIV virus, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need for new compounds for retrovirus therapy, more particularly for AIDS therapy. This need is particularly acute for compounds that are active not only on wild type HIV virus, but also on the increasingly more common resistant HIV viruses.

Known antiretrovirals, often administered in a combination therapy regimen, will eventually cause resistance as stated above. This often may force the physician to boost the plasma levels of the active drugs in order for said antiretrovirals to regain effectivity against the mutated HIV viruses. The consequence of which is a highly undesirable increase in pill burden. Boosting plasma levels may also lead to an increased risk of non-compliance with the prescribed therapy.

Currently used commercially available HIV reverse transcriptase inhibitors belong to three different classes, the NRTIs such as zidovudine, didanosine, zalcibatine, stavudine, abacavir and lamivudine, the NtRTIs such as tenofovir, and NNRTIs such as nevirapine, delavirdine and efavirenz. The NRTIs and NtRTIs are base analogs that target the active site of HIV reverse transcriptase (RT). Currently used NNRTI are known for rapid emergence of resistance due to mutations at amino acids that surround the NNRTI binding site (J AIDS 2001, 26, S25-S33).

Thus, there is a high medical need for anti-infective compounds that target HIV reverse transcriptase, in particular anti-retroviral compounds that are able to delay the occurrence of resistance and that combat a broad spectrum of mutants of the HIV virus.

WO 02/055520 and WO 02/059123 disclose benzoylalkylindolepyridinium compounds as antiviral compounds. Ryabova et al. disclose the synthesis of certain benzoylalkyl-indolepyridinium compounds (Russian Chem. Bull. 2001, 50(8), 1449-1456) (Chem. Heterocycl. Compd. (Engl.Translat.)36; 3; 2000; 301-306; Khim.Geterotsikl.Soedin.; RU; 3; 2000; 362-367).

It is now found that substituted indolepyridinium compounds of formula (I),

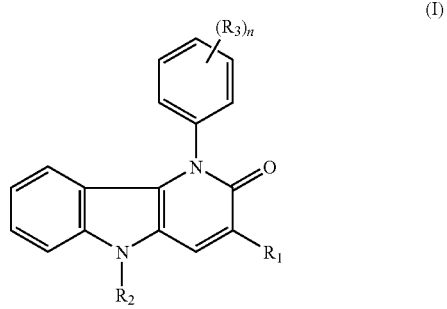

their N-oxides, salts, stereoisomeric forms, racemic mixtures, prodrugs, esters and metabolites, wherein n is 1, 2 or 3;

$R_1$ is hydrogen, cyano, halo, aminocarbonyl, hydroxycarbonyl, $C_{1-4}$alkyloxycarbonyl, $C_{1-4}$alkylcarbonyl, mono- or di($C_{1-4}$alkyl)aminocarbonyl, arylaminocarbonyl, N-(aryl)-N-($C_{1-4}$alkyl)aminocarbonyl, methanimidamidyl, N-hydroxymethanimidamidyl, mono- or di($C_{1-4}$alkyl)methanimidamidyl, $Het_1$ or $Het_2$;

$R_2$ is hydrogen, $C_{1-10}$alkyl, $C_{2-10}$alkenyl, $C_{3-7}$cycloalkyl, wherein said $C_{1-10}$alkyl, $C_{2-10}$alkenyl and $C_{3-7}$cycloalkyl, each individually and independently, may be optionally substituted with a substituent selected from the group consisting of cyano, $NR_{4a}R_{4b}$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $N(R_{4a}R_{4b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-ylcarbonyl, thiomorpholin-1-ylcarbonyl, 1-oxothiomorpholin-1-ylcarbonyl and 1,1-dioxo-thiomorpholin-1-ylcarbonyl;

$R_3$ is nitro, cyano, amino, halo, hydroxy, $C_{1-4}$alkyloxy, hydroxycarbonyl, aminocarbonyl, $C_{1-4}$alkyloxycarbonyl, mono- or di($C_{1-4}$alkyl)aminocarbonyl, $C_{1-4}$alkylcarbonyl, methanimidamidyl, mono- or di($C_{1-4}$alkyl)methanimidamidyl, N-hydroxy-methanimidamidyl or $Het_1$;

$R_{4a}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

$R_{4b}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

aryl is phenyl optionally substituted with one or more substituents each individually selected from the group consisting of $C_{1-6}$alkyl, $C_{1-4}$alkoxy, halo, hydroxy, amino, trifluoromethyl, cyano, nitro, hydroxy$C_{1-6}$alkyl, cyano$C_{1-6}$alkyl, mono- or di($C_{1-4}$alkyl)amino, amino$C_{1-4}$alkyl, mono- or di($C_{1-4}$alkyl)amino$C_{1-4}$alkyl;

$Het_1$ is a 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl;

$Het_2$ is pyridyl, pyrimidinyl, pyrazinyl, pyridazinyl or triazinyl, wherein any ring carbon atom of each of said 6-membered nitrogen containing aromatic rings may optionally be substituted with a substituent selected from the group consisting of $C_{1-4}$alkyl;

inhibit the replication of HIV virus.

In one embodiment, the invention relates to the inhibition of the replication of HIV virus by substituted indolepyridinium compounds of formula (I) wherein $R_1$ is cyano, $C_{1-4}$alkylaminocarbonyl or $C_{1-4}$alkyloxycarbonyl; $R_2$ is hydrogen or $C_{1-6}$alkyl; n is 1 and $R_3$ is nitro.

The compounds of formula (I) are active against wild type HIV virus and also against a variety of mutant HIV viruses including mutant HIV viruses exhibiting resistance against commercially available reverse transcriptase (RT) inhibitors. The compounds of formula (I) are therefore useful as a medicine, and thus also useful in the manufacture of a medicament useful for preventing, treating or combating infection or disease associated with HIV infection.

A subgroup of the compounds of formula (I) is deemed novel and consists of those compounds of formula (I) provided they are different from 2,5-dihydro-1-(4-nitrophenyl)-2-oxo-1H-pyrido[3,2-b]indole-3-carbonitrile, and 2,5-dihydro-5-methyl-1-(4-nitrophenyl)-2-oxo-1H-pyrido[3,2-b]indole-3-carbonitrile.

Thus, the present invention also concerns the compounds of formula (I) having the formula

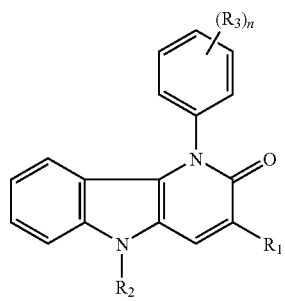

their N-oxides, salts, stereoisomeric forms, racemic mixtures, prodrugs, esters and metabolites, wherein n is 1, 2 or 3;

$R_1$ is hydrogen, cyano, halo, aminocarbonyl, hydroxycarbonyl, $C_{1-4}$alkyloxycarbonyl, $C_{1-4}$alkylcarbonyl, mono- or di($C_{1-4}$alkyl)aminocarbonyl, arylaminocarbonyl, N-(aryl)-N-($C_{1-4}$alkyl)aminocarbonyl, methanimidamidyl, N-hydroxymethanimidamidyl, mono- or di($C_{1-4}$alkyl)methanimidamidyl, $Het_1$ or $Het_2$;

$R_2$ is hydrogen, $C_{1-10}$alkyl, $C_{2-10}$alkenyl, $C_{3-7}$cycloalkyl, wherein said $C_{1-10}$alkyl, $C_{2-10}$alkenyl and $C_{3-7}$cycloalkyl, each individually and independently, may be optionally substituted with a substituent selected from the group consisting of cyano, $NR_{4a}R_{4b}$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $N(R_{4a}R_{4b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-ylcarbonyl, thiomorpholin-1-ylcarbonyl, 1-oxothiomorpholin-1-ylcarbonyl and 1,1-dioxo-thiomorpholin-1-ylcarbonyl;

$R_3$ is nitro, cyano, amino, halo, hydroxy, $C_{1-4}$alkyloxy, hydroxycarbonyl, aminocarbonyl, aminothiocarbonyl, $C_{1-4}$alkyloxycarbonyl, mono- or di($C_{1-4}$alkyl)-aminocarbonyl, $C_{1-4}$alkylcarbonyl, methanimidamidyl, mono- or di($C_{1-4}$alkyl)methanimidamidyl, N-hydroxy-methanimidamidyl or $Het_1$;

$R_{4a}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

$R_{4b}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

aryl is phenyl optionally substituted with one or more substituents each individually selected from the group consisting of $C_{1-6}$alkyl, $C_{1-4}$alkoxy, halo, hydroxy, amino, trifluoromethyl, cyano, nitro, hydroxy$C_{1-6}$alkyl, cyano$C_{1-6}$alkyl, mono- or di($C_{1-4}$alkyl)amino, amino$C_{1-4}$alkyl, mono- or di($C_{1-4}$alkyl)amino$C_{1-4}$alkyl;

Het$_1$ is a 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl;

Het$_2$ is pyridyl, pyrimidinyl, pyrazinyl, pyridazinyl or triazinyl, wherein any ring carbon atom of each of said 6-membered nitrogen containing aromatic rings may optionally be substituted with a substituent selected from the group consisting of $C_{1-4}$alkyl;

provided that the compound is different from 2,5-dihydro-1-(4-nitrophenyl)-2-oxo-1H-pyrido[3,2-b]indole-3-carbonitrile, and 2,5-dihydro-5-methyl-1-(4-nitrophenyl)-2-oxo-1H-pyrido[3,2-b]indole-3-carbonitrile.

One embodiment concerns the compounds of formula (I), their N-oxides, salts, stereoisomeric forms, racemic mixtures, prodrugs, esters and metabolites, wherein R$_1$ is cyano, $C_{1-4}$alkylaminocarbonyl or $C_{1-4}$alkyloxycarbonyl; R$_2$ is hydrogen or $C_{1-6}$alkyl; n is 1 and R$_3$ is nitro; provided that the compound is different from 2,5-dihydro-1-(4-nitrophenyl)-2-oxo-1H-pyrido[3,2-b]indole-3-carbonitrile, and 2,5-dihydro-5-methyl-1-(4-nitrophenyl)-2-oxo-1H-pyrido[3,2-b]indole-3-carbonitrile.

The term "$C_{1-4}$alkyl" as a group or part of a group defines straight and branched chained saturated hydrocarbon radicals having from 1 to 4 carbon atoms, such as, for example, methyl, ethyl, propyl, butyl, 2-methyl-propyl and the like.

The term "$C_{1-6}$alkyl" as a group or part of a group defines straight and branched chained saturated hydrocarbon radicals having from 1 to 6 carbon atoms such as, for example, the groups defined for $C_{1-4}$alkyl and pentyl, hexyl, 2-methylbutyl, 3-methylpentyl and the like.

The term "$C_{2-6}$alkyl" as a group or part of a group defines straight and branched chained saturated hydrocarbon radicals having from 2 to 6 carbon atoms such as for example, ethyl, propyl, butyl, 2-methyl-propyl, pentyl, hexyl, 2-methylbutyl, 3-methylpentyl and the like.

The term "$C_{1-10}$alkyl" as a group or part of a group defines straight and branched chained saturated hydrocarbon radicals having from 1 to 10 carbon atoms such as, for example, the groups defined for $C_{1-6}$alkyl and heptyl, octyl, nonyl, decyl and the like.

The term $C_{2-6}$alkenyl as a group or part of a group defines straight and branched chained hydrocarbon radicals having saturated carbon-carbon bonds and at least one double bond, and having from 2 to 6 carbon atoms, such as, for example, ethenyl, prop-1-enyl, but-1-enyl, but-2-enyl, pent-1-enyl, pent-2-enyl, hex-1-enyl, hex-2-enyl, hex-3-enyl, 1-methyl-pent-2-enyl and the like.

The term $C_{2-10}$alkenyl as a group or part of a group defines straight and branched chained hydrocarbon radicals having saturated carbon-carbon bonds and at least one double bond, and having from 2 to 10 carbon atoms, such as, for example, the groups of $C_{2-6}$alkenyl and hept-1-enyl, hept-2-enyl, hept-3-enyl, oct-1-enyl, oct-2-enyl, oct-3-enyl, non-1-enyl, non-2-enyl, non-3-enyl, non-4-enyl, dec-1-enyl, dec-2-enyl, dec-3-enyl, dec-4-enyl, 1-methyl-pent-2-enyl and the like.

The term $C_{3-7}$cycloalkyl is generic to cyclopropyl, cyclobutyl, cyclopentyl, cyclohexyl and cycloheptyl.

The term halo is generic to fluoro, chloro, bromo or iodo.

The term methanimidamidyl is the radical name for H$_2$N—CH=NH following the Chemical Abstracts Nomenclature (CAS). Like wise N-hydroxy-methanimidamidyl is CAS radical name for H$_2$N—CH=N—OH.

The term "$C_{6-14}$aryl" means an aromatic hydrocarbon ring having from 6 to 14 ring members such as, for example, phenyl, naphthalene, anthracene and phenanthrene. It should be noted that different isomers of the various heterocycles may exist within the definitions as used throughout the specification. For example, oxadiazolyl may be 1,2,4-oxadiazolyl or 1,3,4-oxadiazolyl or 1,2,3-oxadiazolyl; likewise for thiadiazolyl which may be 1,2,4-thiadiazolyl or 1,3,4-thiadiazolyl or 1,2,3-thiadiazolyl; pyrrolyl may be 1H-pyrrolyl or 2H-pyrrolyl.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

When any variable (e.g. halogen or $C_{1-4}$alkyl) occurs more than one time in any constituent, each definition is independent.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either by routine manipulation or in vivo, to the parent compound.

Prodrugs are characterized by excellent aqueous solubility, increased bioavailability and are readily metabolized into the active inhibitors in vivo.

For therapeutic use, the salts of the compounds of formula (I) are those wherein the counterion is pharmaceutically or physiologically acceptable. However, salts having a pharmaceutically unacceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecyl-sulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms that the compounds of the present invention are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide.

The present compounds may also exist in their tautomeric forms. Such forms, although not explicitly indicated in the above formula are intended to be included within the scope of the present invention. For example, within the definition of Het, a 5 membered aromatic heterocycle such as for example an 1,2,4-oxadiazole may be substituted with a hydroxy or a thio group in the 5-position, thus being in equilibrium with its respective tautomeric form as depicted below.

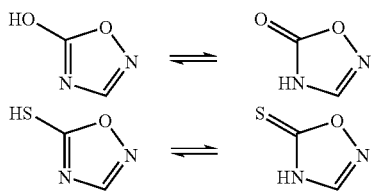

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", or "the present compounds" or similar term is meant to include the compounds of general formula (I), their N-oxides, salts, stereoisomeric forms, racemic mixtures, prodrugs, esters and metabolites, as well as their quaternized nitrogen analogues. An interesting subgroup of the compounds of formula (I) or any subgroup thereof are the N-oxides, salts and all the stereoisomeric forms of the compounds of formula (I).

In one embodiment, n is 1 and the $R_3$ group on the phenyl ring in the compound of formula (I) is in para-position vis-à-vis the nitrogen atom in the fused pyridine moiety as depicted herein below and hereinafter referred to as compounds of formula (II)

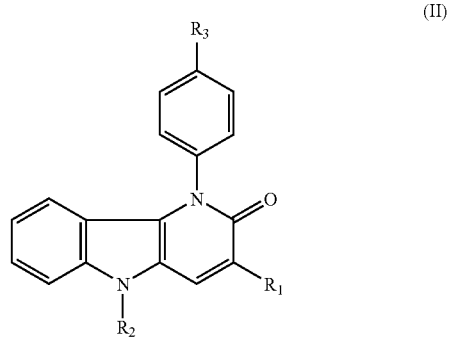

An interesting subgroup of the compounds of formula (II) are those compounds of formula (II), hereinafter referred to compounds of formula (II-a), wherein $R_3$ is nitro.

A particular group of compounds are those compounds of formula (I) wherein $R_1$ is cyano, methyloxycarbonyl, methylaminocarbonyl, ethyloxycarbonyl and ethylaminocarbonyl, more in particular wherein $R_1$ is cyano, ethyloxycarbonyl and ethylaminocarbonyl, even more in particular wherein $R_1$ is cyano.

Another particular group of compounds are those compounds of formula (I) wherein $R_2$ is hydrogen or $C_{1-4}$alkyl, more in particular wherein $R_2$ is hydrogen or methyl, even more in particular wherein $R_2$ is methyl.

Yet another particular group of compounds are those compounds of formula (1) wherein $R_1$ is cyano and $R_2$ is hydrogen or methyl.

A particular group of novel compounds are those compounds of formula (I) wherein $R_1$ is $C_{1-4}$alkylaminocarbonyl or $C_{1-4}$alkyloxycarbonyl.

Another particular group of novel compounds are those compounds of formula (I) wherein $R_1$ is $C_{1-4}$alkylaminocarbonyl or $C_{1-4}$alkyloxycarbonyl and $R_2$ is hydrogen or methyl.

Another particular group of novel compounds are those compounds of formula (I) wherein $R_1$ is methyloxycarbonyl, methylaminocarbonyl, ethyloxycarbonyl or ethylaminocarbonyl, and $R_2$ is hydrogen or methyl.

Another particular group of novel compounds are those compounds of formula (I) wherein $R_2$ is $C_{2-6}$alkyl.

Another particular group of novel compounds are those compounds of formula (I), wherein when $R_1$ is cyano then $R_2$ is different from hydrogen or methyl.

Yet another particular group of compounds are those compounds of formula (I) wherein $R_2$ is hydrogen or $C_{1-4}$alkyl, and the nitro group on the phenyl ring is in the ortho or meta position vis-à-vis the nitrogen atom in the fused pyridine moiety.

A suitable group of compounds are those compounds of formula (I) as a salt, wherein the salt is selected from trifluoroacetate, fumarate, chloroacetate, methanesulfonate, oxalate, acetate and citrate.

An interesting subgroup of the compounds of formula (I) are those compounds of formula (I) or subgroups thereof wherein any combination of the following restrictions applies n is 1 or 2, more in particular wherein n is 1;

$R_1$ is hydrogen, cyano, halo, aminocarbonyl, hydroxycarbonyl, $C_{1-4}$alkyloxycarbonyl, arylaminocarbonyl, N-hydroxy-methanimidamidyl, mono- or di($C_{1-4}$alkyl)methanimidamidyl, $Het_1$ or $Het_2$;

$R_2$ is hydrogen, $C_{1-10}$alkyl, $C_{2-10}$alkenyl, $C_{3-7}$cycloalkyl or $C_{1-10}$alkyl substituted with substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl or 4-($C_{1-4}$alkyl)-piperazin-1-ylcarbonyl;

$R_3$ is nitro, cyano, amino, halo, hydroxy, $C_{1-4}$alkyloxy, hydroxycarbonyl, aminocarbonyl, aminothiocarbonyl, $C_{1-4}$alkyloxycarbonyl, $C_{1-4}$alkylcarbonyl, mono- or di($C_{1-4}$alkyl)methanimidamidyl, N-hydroxy-methanimidamidyl or $Het_1$;

$R_{4a}$ is $C_{1-4}$alkyl;

$R_{4b}$ is $C_{1-4}$alkyl or $C_{1-4}$alkyl substituted morpholinyl;

aryl is phenyl optionally substituted with one or more substituents each individually selected from the group consisting of $C_{1-6}$alkyl, $C_{1-4}$alkoxy, cyano, nitro;

$Het_1$ is a 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{3-7}$cycloalkyl, halo, cyano, trifluoromethyl, cyano$C_{1-4}$alkyl, mono- or di($C_{1-4}$alkyl)amino, mono- or di($C_{1-4}$alkyl)amino$C_{2-6}$alkenyl, isoxazolyl, aryl, hydroxycarbonyl, $C_{1-4}$alkyloxycarbonyl, oxo, thio; and wherein the foregoing isoxazolyl may optionally be substituted with $C_{1-4}$alkyl;

$Het_2$ is pyridyl;

Examples of such combinations of the above mentioned restrictions are for instance the combination of n is 1 or 2, more in particular wherein n is 1; and $R_3$ is nitro, cyano, amino, halo, hydroxy, $C_{1-4}$alkyloxy, hydroxycarbonyl, aminocarbonyl, aminothiocarbonyl, $C_{1-4}$alkyloxycarbonyl, $C_{1-4}$alkylcarbonyl, mono- or di($C_{1-4}$alkyl)methanimidamidyl, N-hydroxy-methanimidamidyl or $Het_1$.

or the combination of $R_1$ is hydrogen, cyano, halo, aminocarbonyl, hydroxycarbonyl, $C_{1-4}$alkyloxycarbonyl, arylaminocarbonyl, N-hydroxy-methanimidamidyl, mono- or di($C_{1-4}$alkyl)methanimidamidyl, $Het_1$ or $Het_2$; and aryl is phenyl optionally substituted with one or more substituents each individually selected from the group consisting of $C_{1-6}$alkyl, $C_{1-4}$alkoxy, cyano, nitro; and $Het_1$ is a 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{3-7}$cycloalkyl, halo, cyano, trifluoromethyl, cyano$C_{1-4}$alkyl, mono- or di($C_{1-4}$alkyl)amino, mono- or di($C_{1-4}$alkyl)amino$C_{2-6}$alkenyl, isoxazolyl, aryl, hydroxycarbonyl, $C_{1-4}$alkyloxycarbonyl, oxo, thio; and wherein the foregoing isoxazolyl may optionally be substituted with $C_{1-4}$alkyl; and $Het_2$ is pyridyl;

or the combination of $R_2$ is hydrogen, $C_{1-10}$alkyl, $C_{2-10}$alkenyl, $C_{3-7}$cycloalkyl or $C_{1-10}$alkyl substituted with substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl or 4-($C_{1-4}$alkyl)-piperazin-1-ylcarbonyl; and $R_{4a}$ is $C_{1-4}$alkyl; and $R_{4b}$ is $C_{1-4}$alkyl or $C_{1-4}$alkyl substituted morpholinyl;

or the combination of $R_2$ is hydrogen, $C_{1-10}$alkyl, $C_{2-10}$alkenyl, $C_{3-7}$cycloalkyl or $C_{1-10}$alkyl substituted with substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl or 4-($C_{1-4}$alkyl)-piperazin-1-ylcarbonyl; and aryl is phenyl optionally substituted with one or more substituents each individually selected from the group consisting of $C_{1-6}$alkyl, $C_{1-4}$alkoxy, cyano, nitro;

or the combination of $R_2$ is hydrogen, $C_{1-10}$alkyl, $C_{2-10}$alkenyl, $C_{3-7}$cycloalkyl or $C_{1-10}$alkyl substituted with substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl or 4-($C_{1-4}$alkyl)-piperazin-1-ylcarbonyl; and aryl is phenyl optionally substituted with one or more substituents each individually selected from the group consisting of $C_{1-6}$alkyl, $C_{1-4}$alkoxy, cyano, nitro; and
$R_{4a}$ is $C_{1-4}$alkyl; and
$R_{4b}$ is $C_{1-4}$alkyl or $C_{1-4}$alkyl substituted morpholinyl;

or the combination of
$R_3$ is nitro, cyano, amino, halo, hydroxy, $C_{1-4}$alkyloxy, hydroxycarbonyl, aminocarbonyl, aminothiocarbonyl, $C_{1-4}$alkyloxycarbonyl, $C_{1-4}$alkylcarbonyl, mono- or di($C_{1-4}$alkyl)methanimidamidyl, N-hydroxy-methanimidamidyl or $Het_1$; and
$Het_1$ is a 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{3-7}$cycloalkyl, halo, cyano, trifluoromethyl, cyano$C_{1-4}$alkyl, mono- or di($C_{1-4}$alkyl)amino, mono- or di($C_{1-4}$alkyl)amino$C_{2-6}$alkenyl, isoxazolyl, aryl, hydroxycarbonyl, $C_{1-4}$alkyloxycarbonyl, oxo, thio; and wherein the foregoing isoxazolyl may optionally be substituted with $C_{1-4}$alkyl;

or the combination of
n is 1 or 2, more in particular wherein n is 1; and
$R_1$ is hydrogen, cyano, halo, aminocarbonyl, hydroxycarbonyl, $C_{1-4}$alkyloxycarbonyl, arylaminocarbonyl, N-hydroxy-methanimidamidyl, mono- or di($C_{1-4}$alkyl)methanimidamidyl, $Het_1$ or $Het_2$; and
$R_2$ is hydrogen, $C_{1-10}$alkyl, $C_{2-10}$alkenyl, $C_{3-7}$cycloalkyl or $C_{1-10}$alkyl substituted with substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl or 4-($C_{1-4}$alkyl)-piperazin-1-ylcarbonyl; and
$R_3$ is nitro, cyano, amino, halo, hydroxy, $C_{1-4}$alkyloxy, hydroxycarbonyl, aminocarbonyl, aminothiocarbonyl, $C_{1-4}$alkyloxycarbonyl, $C_{1-4}$alkylcarbonyl, mono- or di($C_{1-4}$alkyl)methanimidamidyl, N-hydroxy-methanimidamidyl or $Het_1$.

In one embodiment, $R_1$ is hydrogen, cyano, halo, aminocarbonyl, N-hydroxy-methanimidamidyl, $Het_1$; in particular, $R_1$ is hydrogen, cyano, bromo, tetrazolyl or oxadiazolyl optionally substituted with a substituent selected from the group consisting of $C_{1-4}$alkyl, $C_{2-6}$alkenyl, $C_{3-7}$cycloalkyl, hydroxy, $C_{1-4}$alkoxy, amino, cyano, trifluoromethyl, hydroxy$C_{1-4}$alkyl, cyano$C_{1-4}$alkyl, mono- or di($C_{1-4}$alkyl) amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio.

Suitable compounds are those compounds of formula (II) wherein $R_3$ is nitro and $R_1$ is hydrogen, cyano, halo, aminocarbonyl, N-hydroxy-methanimidamidyl, $Het_1$. More suitable compounds are those compounds of formula (II) wherein $R_3$ is nitro, $R_2$ is $C_{1-6}$alkyl and $R_1$ is hydrogen, cyano, bromo, tetrazolyl or oxadiazolyl optionally substituted with a substituent selected from the group consisting of $C_{1-4}$alkyl, $C_{2-6}$alkenyl, $C_{3-7}$cycloalkyl, hydroxy, $C_{1-4}$alkoxy, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio.

In another embodiment, $R_2$ is hydrogen, $C_{1-10}$alkyl, $C_{2-10}$alkenyl, $C_{3-7}$cycloalkyl, wherein said $C_{1-10}$alkyl may be optionally substituted with a substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl, 4-($C_{1-4}$alkyl)-piperazin-1-ylcarbonyl; in particular $R_2$ is hydrogen, $C_{1-6}$alkyl, $C_{2-6}$alkenyl, cyclopropyl, cyclopentyl, wherein said $C_{1-6}$alkyl may be optionally substituted with a substituent selected from the group consisting of cyano, di($C_{1-4}$alkyl)amino, pyrrolidinyl, piperidinyl, 4-(methyl)-piperazinyl, morpholinyl, phenyl, imidazolyl, pyridyl, hydroxycarbonyl, $N(R_{4a}R_{4b})$carbonyl, $C_{1-4}$alkyloxycarbonyl, 4-(methyl)-piperazin-1-ylcarbonyl.

Suitable compounds are those compounds of formula (II) wherein $R_3$ is nitro and $R_1$ is cyano and $R_2$ is $C_{1-10}$alkyl, $C_{2-10}$alkenyl, $C_{3-7}$cycloalkyl, wherein said $C_{1-10}$alkyl may be optionally substituted with a substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl, 4-($C_{1-4}$alkyl)-piperazin-1-ylcarbonyl.

In another embodiment, $R_3$ is nitro, cyano, halo, $C_{1-4}$alkyloxy, hydroxycarbonyl, aminocarbonyl, mono- or di($C_{1-4}$alkyl)methanimidamidyl, N-hydroxymethanimidamidyl or $Het_1$; more in particular, $R_3$ is nitro, cyano, halo, $C_{1-4}$alkyloxy, hydroxycarbonyl, aminocarbonyl, mono- or di($C_{1-4}$alkyl)methanimidamidyl, N-hydroxy-methanimidamidyl, oxadiazolyl, thienyl, thiazolyl, furanyl, isoxazolyl wherein each of said oxadiazolyl, thienyl, thiazolyl, furanyl, isoxazolyl may be substituted with a substituent selected from the group consisting of $C_{1-4}$alkyl, $C_{2-6}$alkenyl, $C_{3-7}$cycloalkyl, hydroxy, $C_{1-4}$alkoxy, amino, cyano, trifluoromethyl, hydroxy$C_{1-4}$alkyl, cyano$C_{1-4}$alkyl, mono- or di($C_{1-4}$alkyl) amino, amino$C_{1-4}$alkyl, mono- or di($C_{1-4}$alkyl)amino$C_{1-4}$ alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl.

Suitable compounds are those compounds of formula (II) wherein $R_1$ is cyano and $R_3$ is nitro, cyano, halo, $C_{1-4}$alkyloxy, hydroxycarbonyl, aminocarbonyl, mono- or di($C_{1-4}$ alkyl)methanimidamidyl, N-hydroxy-methanimidamidyl or $Het_1$. More suitable compounds are those compounds of formula (II) wherein $R_1$ is cyano, $R_2$ is $C_{1-6}$alkyl and $R_3$ is nitro, cyano, halo, $C_{1-4}$alkyloxy, hydroxycarbonyl, aminocarbonyl, mono- or di($C_{1-4}$alkyl)methanimidamidyl, N-hydroxy-methanimidamidyl, oxadiazolyl, thienyl, thiazolyl, furanyl, isoxazolyl wherein each of said oxadiazolyl, thienyl, thiazolyl, furanyl, isoxazolyl may be substituted with a substituent selected from the group consisting of $C_{1-4}$alkyl, $C_{2-6}$alkenyl, $C_{3-7}$cycloalkyl, hydroxy, $C_{1-4}$alkoxy, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl) amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl.

Another embodiment concerns compounds of formula (I) wherein n is 1, $R_1$ is cyano, halo or oxadiazolyl optionally substituted with a substituent selected from the group consisting of $C_{1-4}$alkyl, $C_{2-6}$alkenyl, $C_{3-7}$cycloalkyl, hydroxy, $C_{1-4}$alkoxy, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl;

$R_2$ is $C_{1-6}$alkyl, hydrogen, $C_{2-6}$alkenyl, $R_3$ is nitro, $C_{1-6}$alkyl optionally substituted with piperidinyl, pyrrolidinyl, N($R_{4a}R_{4b}$), morpholinyl, pyridyl, cyano, 4-($C_{1-4}$alkyl)-piperazin-1-yl.

Yet another embodiment relates to compounds of formula (I) wherein $Het_1$ is furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, each of which individually and independently may be optionally substituted with a substituent selected from the group consisting of $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl.

Preferred compounds are 1-(4-Nitro-phenyl)-2-oxo-2,5-dihydro-1H-pyrido[3,2-b]indole-3-carbonitrile;

5-Methyl-1-(4-nitro-phenyl)-2-oxo-2,5-dihydro-1H-pyrido[3,2-b]indole-3-carbonitrile;

5-Isobutyl-1-(4-nitro-phenyl)-2-oxo-2,5-dihydro-1H-pyrido[3,2-b]indole-3-carbonitrile;

5-Allyl-1-(4-nitro-phenyl)-2-oxo-2,5-dihydro-1H-pyrido[3,2-b]indole-3-carbonitrile;

5-Butyl-1-(4-nitro-phenyl)-2-oxo-2,5-dihydro-1H-pyrido[3,2-b]indole-3-carbonitrile;

5-Ethyl-1-(4-nitro-phenyl)-2-oxo-2,5-dihydro-1H-pyrido[3,2-b]indole-3-carbonitrile;

5-(2-Morpholin-4-yl-ethyl)-1-(4-nitro-phenyl)-2-oxo-2,5-dihydro-1H-pyrido[3,2-b]-indole-3-carbonitrile;

5-Methyl-1-(4-nitro-phenyl)-1,5-dihydro-pyrido[3,2-b]indol-2-one;

5-But-3-enyl-1-(4-nitro-phenyl)-2-oxo-2,5-dihydro-1H-pyrido[3,2-b]indole-3-carbonitrile;

1-(4-Nitro-phenyl)-2-oxo-5-(2-pyrrolidin-1-yl-ethyl)-2,5-dihydro-1H-pyrido[3,2-b]-indole-3-carbonitrile;

1-(4-Nitro-phenyl)-2-oxo-5-(2-piperidin-1-yl-ethyl)-2,5-dihydro-1H-pyrido[3,2-b]-indole-3-carbonitrile;

5-(3-Dimethylamino-propyl)-1-(4-nitro-phenyl)-2-oxo-2,5-dihydro-1H-pyrido[3,2-b]-indole-3-carbonitrile;

3-Bromo-5-methyl-1-(4-nitro-phenyl)-1,5-dihydro-pyrido[3,2-b]indol-2-one

5-Methyl-1-(3-nitro-phenyl)-2-oxo-2,5-dihydro-1H-pyrido[3,2-b]indole-3-carbonitrile;

1-(4-Nitro-phenyl)-2-oxo-5-(3-piperidin-1-yl-propyl)-2,5-dihydro-1H-pyrido[3,2-b]indole-3-carbonitrile;

5-(4-Morpholin-4-yl-butyl)-1-(4-nitro-phenyl)-2-oxo-2,5-dihydro-1H-pyrido[3,2-b]-indole-3-carbonitrile;

1-(4-Nitro-phenyl)-2-oxo-5-(4-pyrrolidin-1-yl-butyl)-2,5-dihydro-1H-pyrido[3,2-b]-indole-3-carbonitrile;

5-[3-(4-Methyl-piperazin-1-yl)-propyl]-1-(4-nitro-phenyl)-2-oxo-2,5-dihydro-1H-pyrido[3,2-b]indole-3-carbonitrile;

5-Cyanomethyl-1-(4-nitro-phenyl)-2-oxo-2,5-dihydro-1H-pyrido[3,2-b]indole-3-carbonitrile;

5-(3-Morpholin-4-yl-propyl)-1-(4-nitro-phenyl)-2-oxo-2,5-dihydro-1H-pyrido[3,2-b]-indole-3-carbonitrile;

1-(4-Nitro-phenyl)-2-oxo-5-(4-piperidin-1-yl-butyl)-2,5-dihydro-1H-pyrido[3,2-b]-indole-3-carbonitrile;

5-(4-Dimethylamino-butyl)-1-(4-nitro-phenyl)-2-oxo-2,5-dihydro-1H-pyrido[3,2-b]-indole-3-carbonitrile;

1-(4-Nitro-phenyl)-2-oxo-5-pyridin-4-ylmethyl-2,5-dihydro-1H-pyrido[3,2-b]indole-3-carbonitrile;

3-(5-tert-Butyl-[1,2,4]oxadiazol-3-yl)-5-methyl-1-(4-nitro-phenyl)-1,5-dihydropyrido[3,2-b]indol-2-one;

5-Methyl-1-(4-nitro-phenyl)-3-(5-trifluoromethyl-[1,2,4]oxadiazol-3-yl)-1,5-dihydropyrido[3,2-b]indol-2-one;

and their N-oxides, salts and stereoisomers.

Most preferred compounds are

5-Methyl-1-(4-nitro-phenyl)-2-oxo-2,5-dihydro-1H-pyrido[3,2-b]indole-3-carbonitrile;

5-(2-Morpholin-4-yl-ethyl)-1-(4-nitro-phenyl)-2-oxo-2,5-dihydro-1H-pyrido[3,2-b]-indole-3-carbonitrile;

1-(4-Nitro-phenyl)-2-oxo-5-(2-piperidin-1-yl-ethyl)-2,5-dihydro-1H-pyrido[3,2-b]-indole-3-carbonitrile;

1-(4-Nitro-phenyl)-2-oxo-5-(2-pyrrolidin-1-yl-ethyl)-2,5-dihydro-1H-pyrido[3,2-b]-indole-3-carbonitrile; and their N-oxides, salts and stereoisomers.

The compounds of the present invention inhibit the HIV reverse transcriptase and may also inhibit reverse transcriptases having similarity to HIV reverse transcriptase. Such similarity may be determined using programs known in the art including BLAST. In one embodiment, the similarity at the amino acid level is at least 25%, interestingly at least 50%, more interestingly at least 75%. In another embodiment, the similarity at the amino acid level at the binding pocket, for the compounds of the present invention, is at least 75%, in particular at least 90% as compared to HIV reverse transcriptase. Compounds of the present invention have been tested in other lentivirusses besides HIV-1, such as, for example, SIV and HIV-2.

The compounds of the present invention have a good selectivity as measured by the ratio between $EC_{50}$ and $CC_{50}$ as described and exemplified in the antiviral analysis example. The compounds of the present invention have also a favorable specificity. There exists a high dissociation between the activity on lentiviruses versus other retroviridae, such as MLV, and versus non-viral pathogens. For instance, compound 2 had an $EC_{50}$ value of more than 32 µM for *Mycobacterium b.*, *Plasmodium f*, *Trypanosoma b.* and *Trypanosoma c.* whereas the $EC_{50}$ value for wild-type HIV was well below 100 nM.

The standard of "sensitivity" or alternatively "resistance" of a HIV reverse transcriptase enzyme to a drug is set by the commercially available HIV reverse transcriptase inhibitors. Existing commercial HIV reverse transcriptase inhibitors including efavirenz, nevirapine and delavirdine may loose effectivity over time against a population of HIV virus in a patient. The reason being that under pressure of the presence of a particular HIV reverse transcriptase inhibitor, the existing population of HIV virus, usually mainly wild type HIV reverse transcriptase enzyme, mutates into different mutants which are far less sensitive to that same HIV reverse transcriptase inhibitor. If this phenomenon occurs, one talks about resistant mutants. If those mutants are not only resistant to that one particular HIV reverse transcriptase inhibitor, but also to multiple other commercially available HIV reverse transcriptase inhibitors, one talks about multi-drug resistant HIV reverse transcriptase. One way of expressing the resistance of a mutant to a particular HIV reverse transcriptase inhibitor is making the ratio between the $EC_{50}$ of said HIV reverse transcriptase inhibitor against mutant HIV reverse transcriptase over $EC_{50}$ of said HIV reverse transcriptase inhibitor against wild type HIV reverse transcriptase. Said ratio is also called fold change in resistance (FR). The $EC_{50}$ value represents the amount of the compound required to protect 50% of the cells from the cytopathogenic effect of the virus.

Many of the mutants occurring in the clinic have a fold resistance of 100 or more against the commercially available HIV reverse transcriptase inhibitors, like nevirapine, efavirenz, delavirdine. Clinically relevant mutants of the HIV reverse transcriptase enzyme may be characterized by a mutation at codon position 100, 103 and 181. As used herein a codon position means a position of an amino acid in a protein sequence. Mutations at positions 100, 103 and 181 relate to non-nucleoside RT inhibitors (D'Aquila et al. Topics in HIV medicine, 2002, 10, 11-15). Examples of such clinical relevant mutant HIV reverse transcriptases are listed in Table 1.

TABLE 1

List of mutations present in reverse transcriptase of the HIV strains used.

| | |
|---|---|
| A | Y181C |
| B | K103N |
| C | L100I; K103N |
| D | L100I; K103N |
| E | F227C |
| F | Y188L |
| G | V106A, F227L |
| H | K103N, Y181C |
| I | K101E, K103N |
| J | 131L, L100I, K103N, E138G, Y181C, L214F |
| K | K2OR, E28K, M41L, E44A, D67N, L74I, K103N, V118I, D123N, S162C, Y181C, G196K, Q207E, L210W, L214F, T215Y, K219N, P225H, D250E, P272A, R277K, I293V, P297K, K311R, R358K, T376A, E399D, T400L |

An interesting group of compounds are those compounds of formula (I) having a fold resistance ranging between 0.01 and 100 against at least one mutant HIV reverse transcriptase, suitably ranging between 0.1 and 100, more suitably ranging between 0.1 and 50, and even more suitably ranging between 0.1 and 30. Of particular interest are the compounds of formula (I) showing a fold resistance against at least one mutant HIV reverse transcriptase ranging between 0.1 and 20, and even more interesting are those compounds of formula (I) showing a fold resistance against at least one mutant HIV reverse transcriptase ranging between 0.1 and 10.

An interesting group of compounds are those compounds of formula (I) having a fold resistance, determined according to the methods herein described, in the range of 0.01 to 100 against HIV species having at least one mutation in the amino acid sequence of HIV reverse transcriptase as compared to the wild type sequence (genbank accession e.g. M38432, K03455, gi 327742) at a position selected from 100, 103 and 181; in particular at least two mutations selected from the positions 100, 103 and 181. Even more interesting are those compounds within said interesting group of compounds having a fold resistance in the range of 0.1 to 100, in particular in the range 0.1 to 50, more in particular in the range 0.1 to 30. Most interesting are those compounds within said interesting group of compounds having a fold resistance in the range of 0.1 and 20, especially ranging between 0.1 and 10.

In one embodiment, the compounds of the present invention show a fold resistance in the ranges mentioned just above against at least one clinically relevant mutant HIV reverse transcriptases.

A particular group of compounds are those compounds of formula (I) having an $IC_{50}$ of 1 µM or lower, suitably an $IC_{50}$ of 100 nM or lower vis-à-vis the wild type virus upon in vitro screening according to the methods described herein.

The ability of the present compounds to inhibit HIV-1, HIV-2, SIV and HIV viruses with reverse transcriptase (RT) enzymes having mutated under pressure of the currently known RT inhibitors, together with the absence of cross resistance with currently known RT inhibitors indicate that the present compounds bind differently to the RT enzyme when compared to the known NNRTIs and NRTIs. With respect to the cross resistance, a study with more than 8000 viruses showed that the calculated correlation coefficient between the present compound 2 and known NRTIs, such as for example 3TC, abacavir, AZT, D4T, DDC, DDI, was in all cases lower than 0.28 with an exception of 3TC where the correlation coefficient was about 0.63. The correlation coefficient between the present compound 2 and known NNRTIs such as for example capravirine, delavirdine, nevirapine and efavirenz was in all cases about 0.13 or lower.

The compounds of the present invention show antiretroviral properties, in particular against Human Immunodeficiency Virus (HIV), which is the aetiological agent of Acquired Immune Deficiency Syndrome (AIDS) in humans. The HIV virus preferentially infects CD4 receptor containing cells such as human T4 cells and destroys them or changes their normal function, particularly the coordination of the immune system. As a result, an infected patient has an ever-decreasing number of T4 cells, which moreover behave abnormally. Hence, the immunological defence system is unable to combat infections and/or neoplasms and the HIV infected subject usually dies by opportunistic infections such as pneumonia, or by cancers. Other diseases associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC). The HIV virus also infects CD8-receptor containing cells. Other target cells for HIV virus include microglia, dendritic cells, B-cells and macrophages.

Due to their favourable pharmacological properties, particularly their activity against HIV reverse transcriptase enzymes, the compounds of the present invention or any subgroup thereof may be used as medicines against above-mentioned diseases or in the prophylaxis thereof. Said use as a medicine or method of treatment comprises the systemic administration to HIV-infected subjects of an amount effective to combat the conditions associated with HIV.

In one embodiment, the present invention concerns the use of a compound of formula (I) or any subgroup thereof in the manufacture of a medicament useful for preventing, treating or combating infection or disease associated with HIV infection.

In another embodiment, the present invention concerns the use of a compound of formula (I) or any subgroup thereof in the manufacture of a medicament useful for inhibiting replication of a HIV virus, in particular a HIV virus having a mutant HIV reverse transcriptase, more in particular a multi-drug resistant mutant HIV reverse transcriptase.

In yet another embodiment, the present invention relates to the use of a compound of formula (I) or any subgroup thereof in the manufacture of a medicament useful for preventing, treating or combating a disease associated with HIV viral infection wherein the reverse transcriptase of the HIV virus is mutant, in particular a multi-drug resistant mutant HIV reverse transcriptase.

The compounds of formula (I) or any subgroup thereof are also useful in a method for preventing, treating or combating infection or disease associated with HIV infection in a mammal, comprising administering to said mammal an effective amount of a compound of formula (I) or any subgroup thereof.

In another aspect, the compounds of formula (I) or any subgroup thereof are useful in a method for preventing, treating or combating infection or disease associated with infection of a mammal with a mutant HIV virus, comprising administering to said mammal an effective amount of a compound of formula (I) or any subgroup thereof.

In another aspect, the compounds of formula (I) or any subgroup thereof are useful in a method for preventing, treating or combating infection or disease associated with infection of a mammal with a multi drug-resistant HIV virus, comprising administering to said mammal an effective amount of a compound of formula (I) or any subgroup thereof.

In yet another aspect, the compounds of formula (I) or any subgroup thereof are useful in a method for inhibiting replication of a HIV virus, in particular a HIV virus having a mutant HIV reverse transcriptase, more in particular a multi-drug resistant mutant HIV reverse transcriptase, comprising administering to a mammal in need thereof an effective amount of a compound of formula (I) or any subgroup thereof.

Most interestingly, a mammal as mentioned in the present methods is a human being.

The compounds of the present invention may also find use in inhibiting ex vivo samples containing HIV or expected to be exposed to HIV. Hence, the present compounds may be used to inhibit HIV present in a body fluid sample that contains or is suspected to contain or be exposed to HIV.

Particular reaction procedures to make the present compounds are described below. In the preparations described below, the reaction products may be isolated from the medium and, if necessary, further purified according to methodologies generally known in the art such as, for example, extraction, crystallization, trituration and chromatography.

Route 1: Synthesis of Present Compounds wherein $R_3$ is Nitro, Cyano ($R_{3'}$)

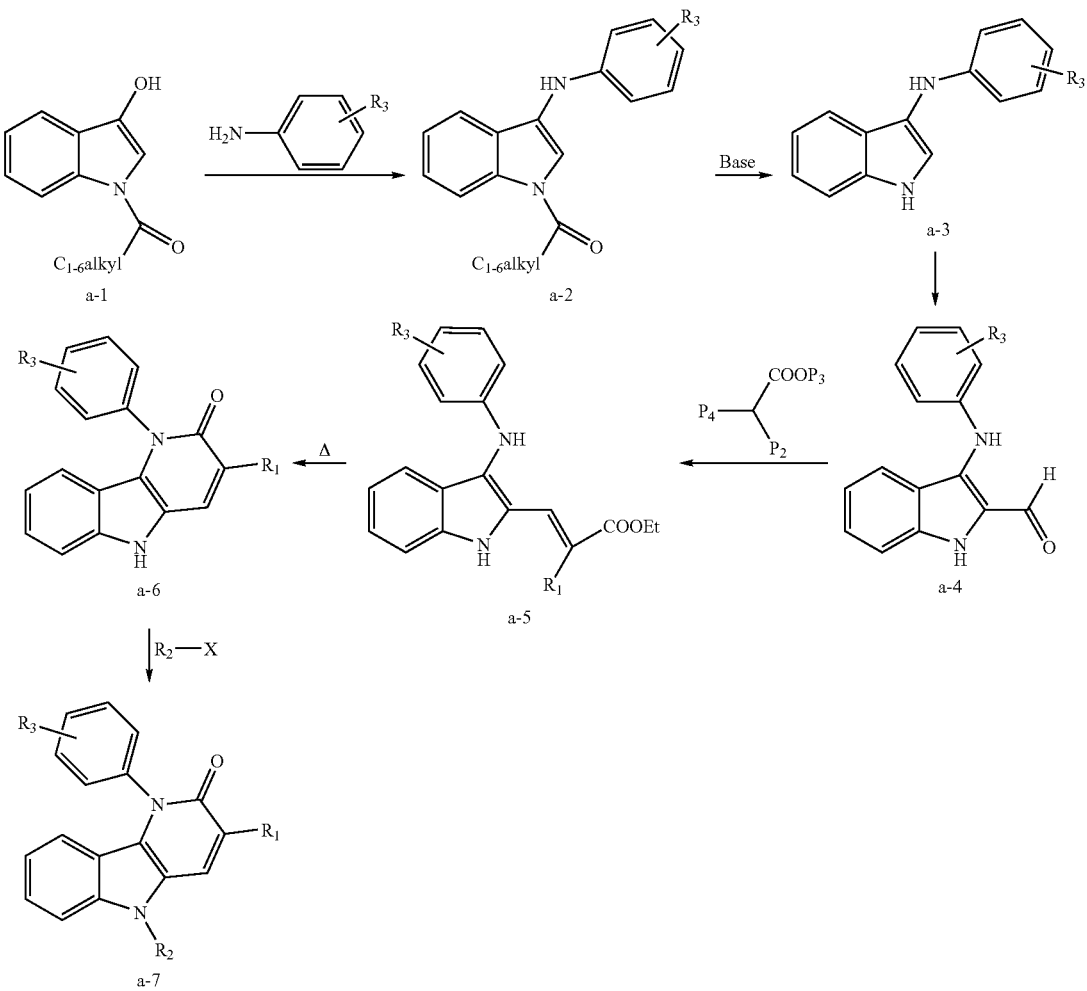

The synthesis of compounds (a-6) and (a-7) conveniently starts from 1-$C_{1-6}$alkylcarbonyl-3-hydroxyindole (a-1). Condensation of (a-1) with nitroaniline at elevated temperatures and in a suitable solvent such as acetic acid, toluene, benzene, an alcohol and the like, yields 3-((nitrophenyl)amino)indole (a-2). In one embodiment, the nitroaniline is para-nitroaniline. Intermediate (a-2) can then be deacylated with a base, such as for example triethylamine, sodiumhydroxide, sodiumacetate, potassiumacetate or potassiumcarbonate and the like, in a suitable solvent, such as for example methanol or ethanol, and at elevated temperature, yielding intermediate (a-3). Formylation of intermediate (a-3) results in indole aldehyde (a-4) and may be performed by employing for instance a Vilsmeier reaction. Condensation of intermediate (a-4) results in intermediate (a-5). In one embodiment, said condensation may be performed using a base such as for example triethylamine, sodiumacetate, potassiumacetate, piperidine and the like, in a wide variety of solvents, and with a oxycarbonylmethylene reagent of formula $CHR_1P_2$—C(=O)—$OP_1$, wherein $P_1$ represents $C_{1-6}$alkyl, $C_{6-14}$aryl or $C_{6-14}$aryl-$C_{1-6}$alkyl and $P_2$ represents a hydrogen, a carboxylic ester, a phosphonium salt or a phosphonate ester. Suitably, the reagent is of formula $CH_2R_1$—C(=O)—$OP_1$, wherein $P_1$ is $C_{1-6}$alkyl. Subsequent intramolecular cyclisation of intermediate (a-5) at elevated temperature and in a solvent like ethyleneglycol, dioxane, N,N-dimethylformamide, dimethylsulfoxide, glyme, diglyme and the like, yields compound (a-6) which may be transformed into a compound of formula (a-7) using an N-alkylation reaction with an intermediate of formula $R_2$—X wherein X is a leaving group. Examples of such leaving groups include sulfonates such as tosylate, mesylate; acetates; halogens such bromide, iodide, chloride and fluoride.

Other transformations from the compounds of formula (a-6) and (a-7) may be performed using art-known transformation techniques. For instance, the compounds of formula (a-6) or (a-7) wherein $R_3$ is nitro may be reduced to $R_3$ being amino, and may then be further derivatized. Further examples of transformation reactions are given in example schemes A2 through A15 in the experimental part.

The order of the mentioned steps in said process scheme A may be different. For instance the formylation may be performed prior to deacylation.

Oxycarbonylmethylene reagents of formula $CHR_1P_2$—C(=O)—$OP_1$ wherein $P_2$ represents a carboxylic ester are for instance dicarboxylic esters of formula $P_1O$—C(=O)—$CHP_2$—C(=O)—$OP_1$. Oxycarbonylmethylene reagents of formula $CHR_1P_2$—C(=O)—$OP_1$ wherein $P_2$ represents a phosphonium salt may for instance have the formula $(P_1)_3$P=$CR_1$—C(=O)—$OP_1$. Oxycarbonylmethylene reagents of formula $CHR_1P_2$—C(=O)—$OP_1$ wherein $P_2$ represents $(P_1O)_2P$(=O)— may for instance have the formula $(P_1O)_2P$(=O)—$CHR_1$—C(=O)—$OP_1$.

Route 2: Synthesis of Present Compounds wherein $R_3$ is Halo or $C_{1-6}$alkyloxy ($R_3''$)

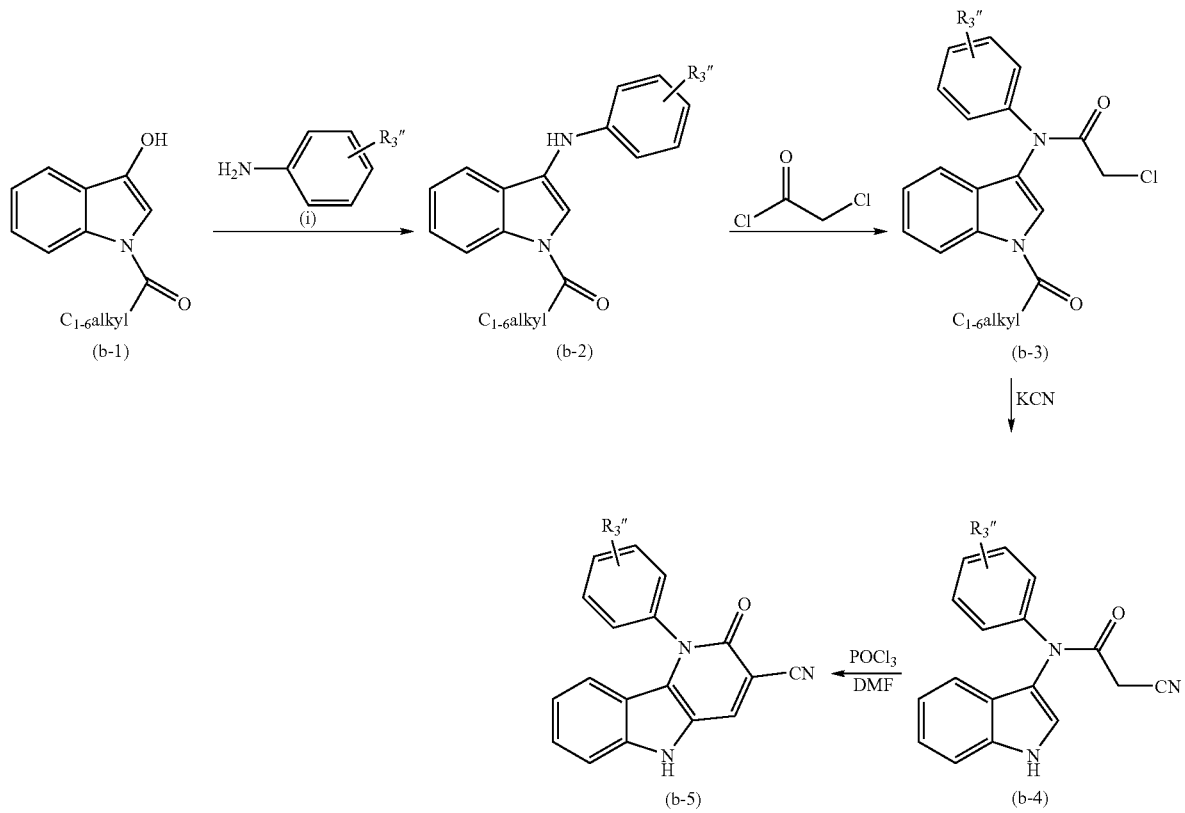

The intermediate (b-1) may be reacted with a reagent of formula (i) in a suitable solvent such as for example toluene, acetic acid, an alcohol and the like, in the presence of a catalyst such as for example p-toluenesulfonic acid to yield an intermediate of formula (b-2). Elevated temperatures and stirring may enhance the reaction. Said intermediate (b-2) may then be reacted with chloroacetyl chloride or a functional derivative thereof, suitable at elevated temperature, to yield an intermediate of formula (b-3). Said intermediate of formula (b-3) may be deprotected using a suitable base such as trietylamine, sodiumacetate, potassium acetate, sodiumhydroxide, potassiumhydroxide, potassiumcarbonate and the like, in a solvent like methanol or ethanol. Stirring and heating may enhance the reaction. The thus formed intermediate of formula (b-4) may be cyclised by first using potassiumcyanide or tetrabutylammoniumcyanide, and subsequently submitting the intermediate to a Vilsmeier formylation using POCl$_3$ in N,N-dimethylformamide to form compound (b-5) which belongs to the class of compounds of formula (I).

Said compound (b-5) may further be transformed into other compounds of formula (I) using art-known transformation reactions. Of which several are described in the exemplary scheme in the experimental part of the description. For example where R$_3$ is Br, Br may be transformed into a Heterocyclic ring using Heterocyclic borates and palladium.

Route 3: Synthesis of Present Compounds wherein R$_3$ is Cyano, Nitro or C$_{1-6}$alkyloxycarbonyl (R$_3$''')

The intermediate (c-1) may be reacted with a reagent of formula (i) in a suitable solvent such as for example toluene, acetic acid, an alcohol and the like, in the presence of a catalyst such as for example p-toluenesulfonic acid to yield an intermediate of formula (c-2). Elevated temperatures and stirring may enhance the reaction. Said intermediate (c-2) may then be reacted with acetic anhydride in the presence of a catalyst such as for example pyridine or dimethylaminopyridine or the like, suitable at elevated temperature, to yield an intermediate of formula (c-3). The thus formed intermediate of formula (c-3) may be reacted using a Vilsmeier reaction with POCl$_3$ in N,N-dimethylformamide to form intermediate (c-4) which in turn can be further cyclised to compound (c-5) in an aqueous acidic environment.

Said compound (c-5), belonging to the class of compounds of formula (I), may further be transformed into other compounds of formula (I) using art-known transformation reactions. Of which several are described in the exemplary scheme in the experimental part of the description. For example R$_3$ being C$_{1-6}$alkyloxycarbonyl may be transformed to the equivalent carboxylic acid or amide. Also R$_3$ being cyano may be transformed to a heterocycle such as a tetrazolyl, oxadiazolyl, thiazolyl etc.

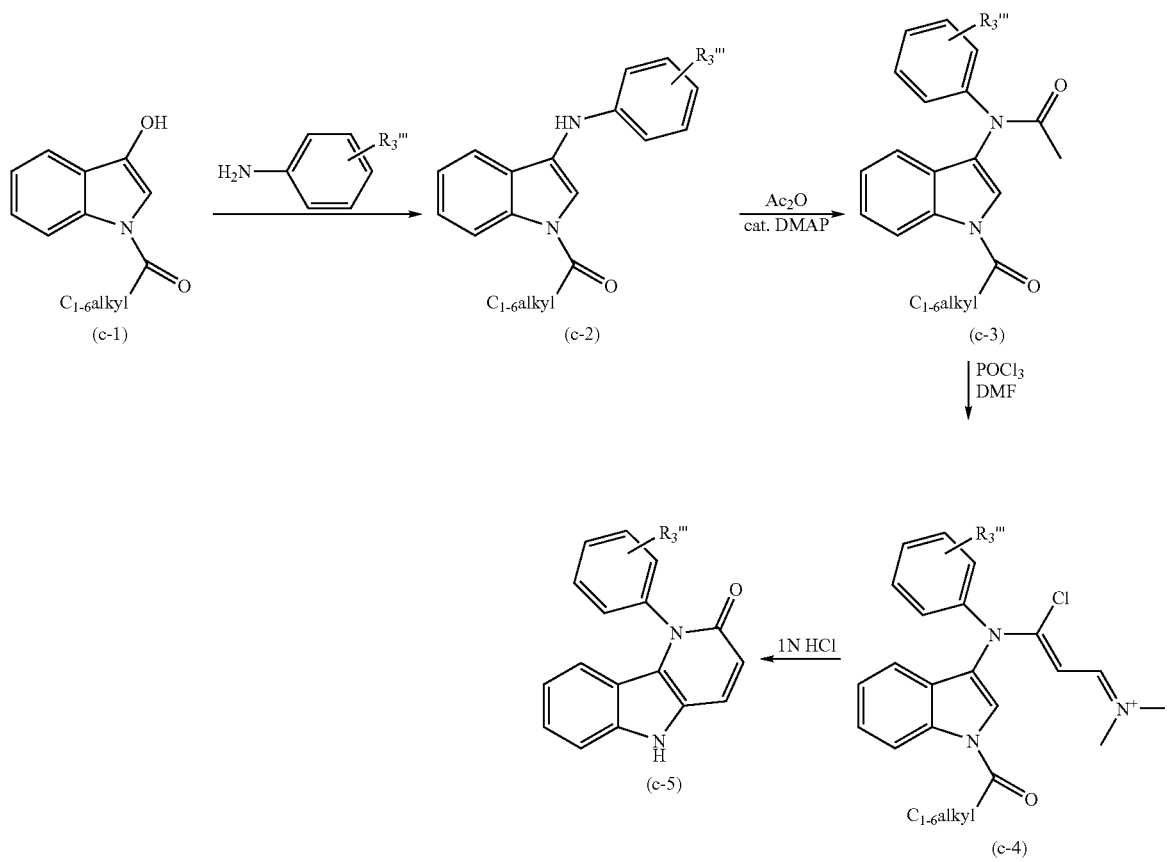

Route 4: Synthesis of Present Compounds wherein $R_1$ is Hydrogen

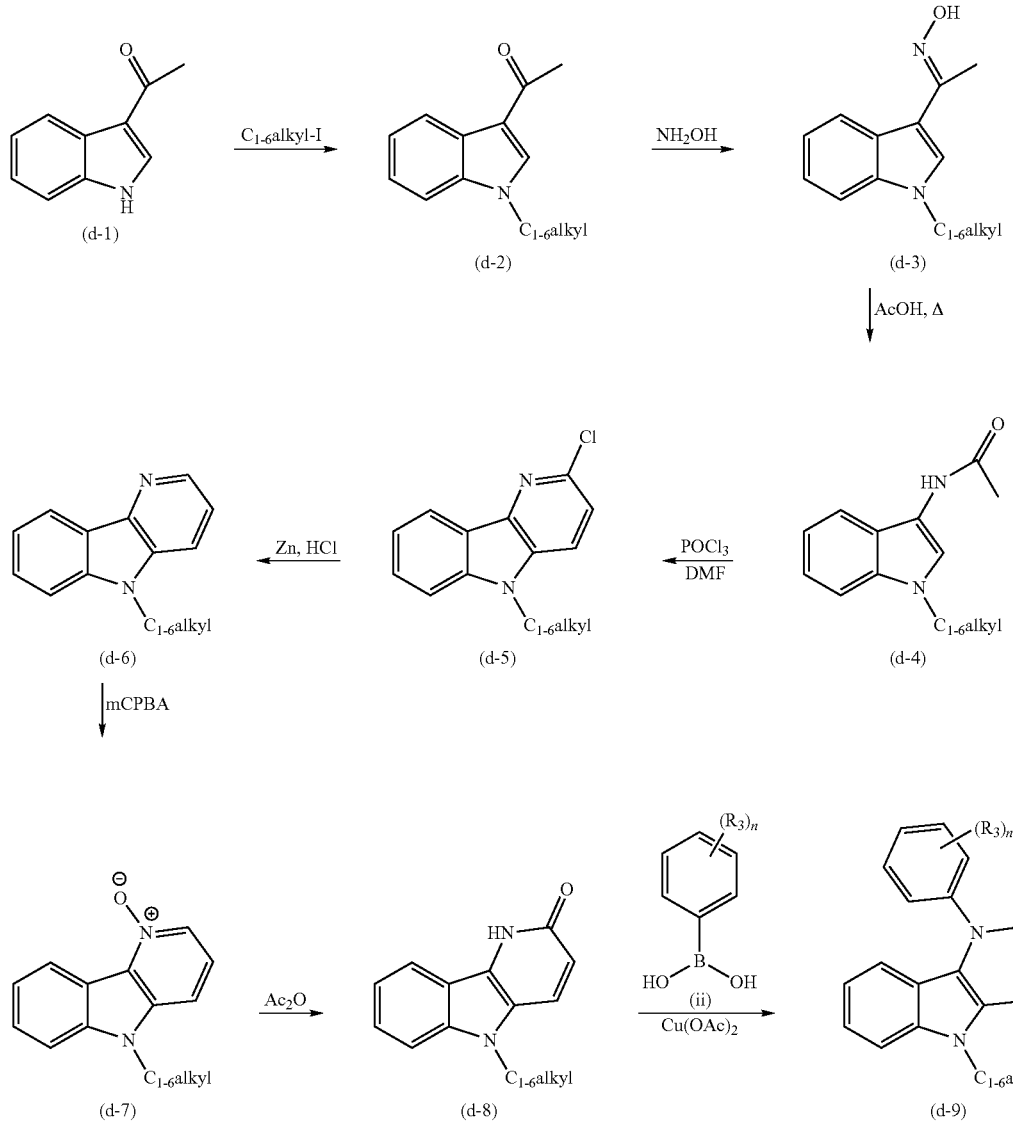

An intermediate of formula (d-1) can be reacted with a $C_{1-6}$alkyliodide or $C_{1-6}$alkylsulfate in the presence of a base such as for example potassium carbonate, potassiumhydroxide, sodiumhydroxide and the like, in a reaction-inert solvent such as for example N,N-dimethylformamide, acetonitrile, acetone, ethanol, water and the like. Stirring may enhance the reaction rate. The thus formed intermediate of formula (d-2) can then be further reacted with hydroxylamine in a solvent like water, ethanol or a mixture thereof and in the presence of a base like sodiumacetate, potassium acetate, potassium carbonate, sodiumacetate and the like, to form an intermediate of formula (d-3). Upon heating and bringing the intermediate of formula (d-3) in an acidic aqueous environment, an intermediate of formula (d-4) is formed. Said intermediate can then be subjected to an intramolecular cyclisation in the presence of $POCl_3$ in N,N-dimethylformamide. Cooling the reaction mixture may be advantageous. The thus formed intermediate of formula (d-5) can be treated with Zinc in an acidic aqueous environment such as HCl to form an intermediate of formula (d-6). The N-oxide can be prepared using metachloroperbenzoic acid, waterperoxide, tert-butylhydroperoxide and the like, or a functional equivalent thereof in a solvent such as, for example, dichloromethane, chloroform, an alcohol, toluene or the like, and employing elevated temperatures. Said N-oxide of formula (d-7) can be further reacted, suitably at elevated temperature, with acetic anhydride to form the intermediate of formula (d-8). Finally, a boronic acid of formula (ii) can be used to prepare the compounds of formula (I) equivalent to the formula (d-9). Said reaction step involves the use of copper(II) acetate or an equivalent thereof in a solvent such as for example N,N-dimethylformamide, dichloromethane, toluene, an alcohol, chloroform and the like. Suitable a quencher like pyridine may be added to the reaction mixture. Elevating the temperature may enhance the reaction.

Route 5: Synthesis of Present Compounds with Different R2

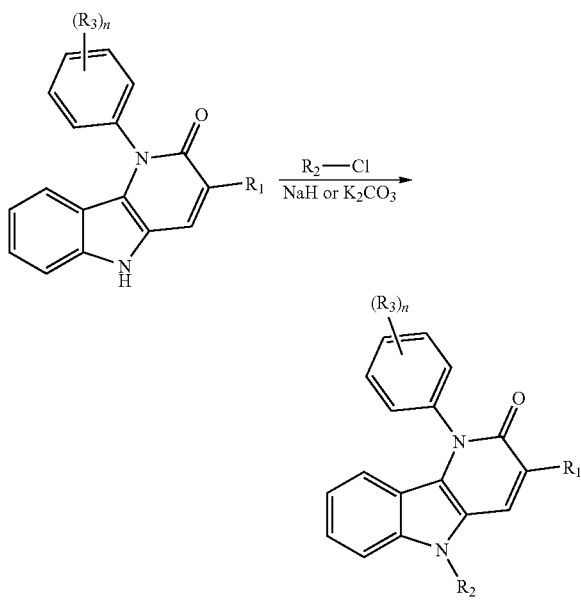

The compounds of formula (I) wherein $R_2$ is hydrogen can be transformed into compounds of formula (I) wherein $R_2$ is different from hydrogen. For this purpose, reagents like $R_2$—Cl wherein Cl is a leaving group can be used in the presence of a base such as sodium hydride or potassium carbonate, potassium hydroxide, sodiumhydroxide and the like. Other suitable leaving groups may also be employed such as for example sulfonates such as tosylate, mesylate; acetates; halogens such bromide, iodide, chloride and fluoride. The reaction procedure can be used for introducing for instance methyl, ethyl, cyclopropyl, butyl, isobytul, isopentyl, cyclopentyl;
allyl, homoallyl, benzyl;
4-pyridinylmethyl, 3-pyridinylmethyl, 2-pyridinylmethyl; 4-imidazolyl-ethyl;
dimethylamino(-ethyl, -propyl, -butyl), piperidino(-ethyl, -propyl, -butyl), pyrrolidino(-ethyl, -propyl, -butyl), N-methyl-piperazino(-ethyl, -propyl, -butyl), pyrrolidino(-ethyl, -propyl, -butyl);
cyanomethyl, cyanoethyl;
alkylation with ethyl bromoacetate and further conversion of the ester to carboxyxlic acid and amides;

Other transformation reactions not specifically mentioned above may also be performed. Some examples thereof are mentioned in the exemplary schemes in the experimental part of the description.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A basic nitrogen occurring in the present compounds can be quaternized with any agent known to those of ordinary skill in the art including, for instance, lower alkyl halides, dialkyl sulfates, long chain halides and aralkyl halides according to art-known procedures.

The present compounds can thus be used in animals, preferably in mammals, and in particular in humans as pharmaceuticals per se, in mixtures with one another or in the form of pharmaceutical preparations.

Consequently, the present invention relates to pharmaceutical preparations that as active constituents contain an effective dose of at least one of the compounds of formula (I) in addition to customary pharmaceutically innocuous excipients and auxiliaries. The pharmaceutical preparations normally contain 0.1 to 90% by weight of a compound of formula (I). The pharmaceutical preparations can be prepared in a manner known per se to one of skill in the art. For this purpose, at least one of a compound of formula (I), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries that are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retroviral infections such as HIV infection, in particular, in the treatment of infections with multi-drug resistant retroviruses. Thus, to prevent, combat or treat HIV infections and the disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, RPR 103611, YK-FH312, IC 9564, 5-helix, D-peptide ADS-J1; co-receptor binding inhibitors, such as, for example, AMD 3100, AMD-3465, AMD7049, AMD3451 (Bicyclams), TAK 779, T-22, ALX40-4C; SHC-C (SCH351125), SHC-D, PRO-140, RPR103611; RT inhibitors, such as, for example, foscarnet and prodrugs; nucleoside RTIs, such as, for example, AZT, 3TC, DDC, DDI, D4T, Abacavir, FTC, DAPD (Amdoxovir), dOTC (BCH-10652), fozivudine, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, QM96521, GW420867X, DPC 961, DPC963, DPCO82, DPC083, calanolide A, SJ-3366, TSAO, 4"-deaminated TSAO, MV 150, MV026048, PNU-142721; RNAse H inhibitors, such as, for example, SP1093V, PD126338; TAT inhibitors, such as, for example, RO-5-3335, K12, K37; integrase inhibitors, such as, for example, L 708906, L 731988, S-1360; protease inhibitors, such as, for example, amprenavir and fosamprenavir, ritonavir, nelfinavir, saquinavir, indinavir, lopinavir, palinavir, BMS 186316, atazanavir, DPC 681, DPC 684, tipranavir, AG1776, mozenavir, DMP-323, GS3333, KNI413, KNI-272, L754394, L756425, LG-71350, PD 161374, PD 173606, PD 177298, PD 178390, PD178392, PNU 140135, TMC-114, maslinic acid, U-140690; glycosylation inhibitors, such as, for example, castanospermine, deoxynojirimycine; entry inhibitors CGP64222.

The combination may provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, and naltrexone) with antibiotics (e.g., pentamidine isothiorate) cytokines (e.g. Th2), modulators of cytokines, chemokines or modulators of chemokines, chemokine receptors (e.g. CCR5, CXCR4), modulators chemokine receptors, or hormones (e.g. growth hormone) to ameliorate, combat, or eliminate HIV infection and its symptoms. Such combination therapy in different formulations, may be administered simultaneously, sequentially or independently of each other. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. It is known that several isoenzymes exist of cytochrome P450, one of which is cytochrome P450 3A4. Ritonavir is an example of a modulator of metabolization via cytochrome P450. Such combination therapy in different formulations, may be administered simultaneously, sequentially or independently of each other. Alternatively, such combination may be administered as a single formulation, whereby the active ingredients are released from the formulation simultaneously or separately. Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum Dilute, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefore such as solubilizers, emulsifiers or further auxiliaries, are brought into solution, suspension, or emulsion. The compounds of formula (I) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavours.

Other convenient ways to enhance the solubility of the compounds of the present invention in pharmaceutical compositions are described in WO 94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2 % aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those that physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include ☐iluted☐c and anionic surfactants.

Yet another interesting way of formulating the present compounds involves a pharmaceutical composition whereby the present compounds are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The route of administration may depend on the condition of the subject, co-medication and the like.

Another aspect of the present invention concerns a kit or container comprising a compound of formula (I) in an amount effective for use as a standard or reagent in a test or assay for determining the ability of a potential pharmaceutical to inhibit HIV reverse transcriptase, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram®. The Antivirogram® is a highly automated, high throughput, second generation, recombinant assay that can measure susceptibility, especially viral susceptibility, to the compounds of the present invention. (Hertogs K et al. *Antimicrob Agents Chemother*, 1998; 42(2):269-276, incorporated by reference).

Interestingly, the compounds of the present invention may comprise chemically reactive moieties capable of forming covalent bonds to localized sites such that said compound have increased tissue retention and half-lives. The term "chemically reactive group" as used herein refers to chemical groups capable of forming a covalent bond. Reactive groups will generally be stable in an aqueous environment and will usually be carboxy, phosphoryl, or convenient acyl group, either as an ester or a mixed anhydride, or an imidate, or a maleimidate thereby capable of forming a covalent bond with functionalities such as an amino group, a hydroxy or a thiol at the target site on for example blood components such as albumine. The compounds of the present invention may be linked to maleimide or derivatives thereof to form conjugates.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight co-medication and individual responsiveness of the human or animal to be treated and on whether the therapy is acute or prophylactic. Customarily, the daily dose of a compound of formula (I) in the case of administration to a patient approximately 75 kg in weight is 1 mg to 3 g, preferably 3 mg to 1 g, more preferably, 5 mg to 0.5 g. The dose can be administered in the form of an individual dose, or divided into several, e.g. two, three, or four, individual doses.

LEGENDS OF THE FIGURES

Figure 2:
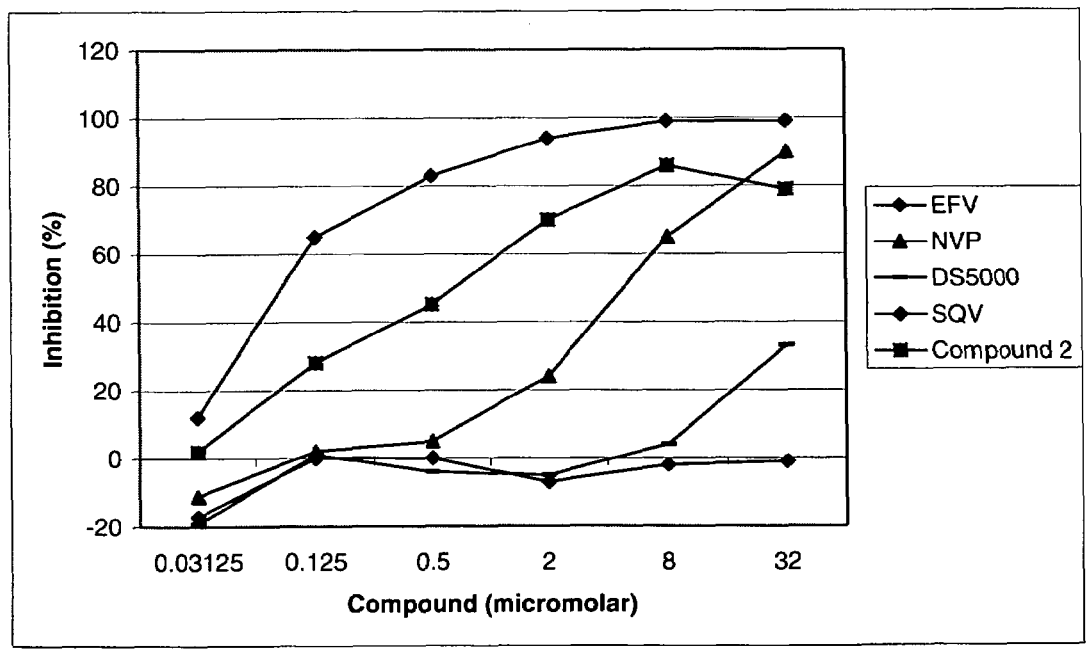

FIG. 1: Time of addition experiment.
Y-axis: normalized virus production in %. X-axis: time of addition, in hours, of the compounds under investigation, following infection of the cells with HIV-LAI.
FIG. 2: In vitro inhibition of reverse transcriptase.
Y-axis: percentage inhibition of HIV reverse transcriptase compared to control. X-axis: amount of compound added to wells in micromolar.

EXPERIMENTAL PART

Preparation of the compounds of formula (I) and their intermediates triethylamine in refluxing methanol and formylation of intermediate (c) using phosphorus oxychloride in dimetylformamide resulted in intermediate (d) (Ryabova, S. Yu.; Tugusheva, N. Z.; Alekseeva, L. M.; Granik, V. G.; Pharm. Chem. J. (Engl. Transl.); EN; 30; 7; 1996; 472-477; Khim.Farm.Zh.; RU; 30; 7; 1996; 42-46). Knoevenagel condensation of intermediate (d) with ethyl cyanoacetate in the presence of a catalytic amount of triethylamine and subsequent intramolecular cyclisation of intermediate (e) under reflux in 1,2-ethanediol, yielded compound (1) (1-(4-nitrophenyl)-2-oxo-2,5-dihydro-1H-pyrido[3,2-b]indole-3-carbonitrile) (Ryabova, S. Yu.; Alekseeva, L. M.; Granik, B. G.; Chem. Heterocycl. Compd. (Engl.Translat.)36; 3; 2000; 301-306; Khim.Geterotsikl.Soedin.; RU; 3; 2000; 362-367). N-methy-

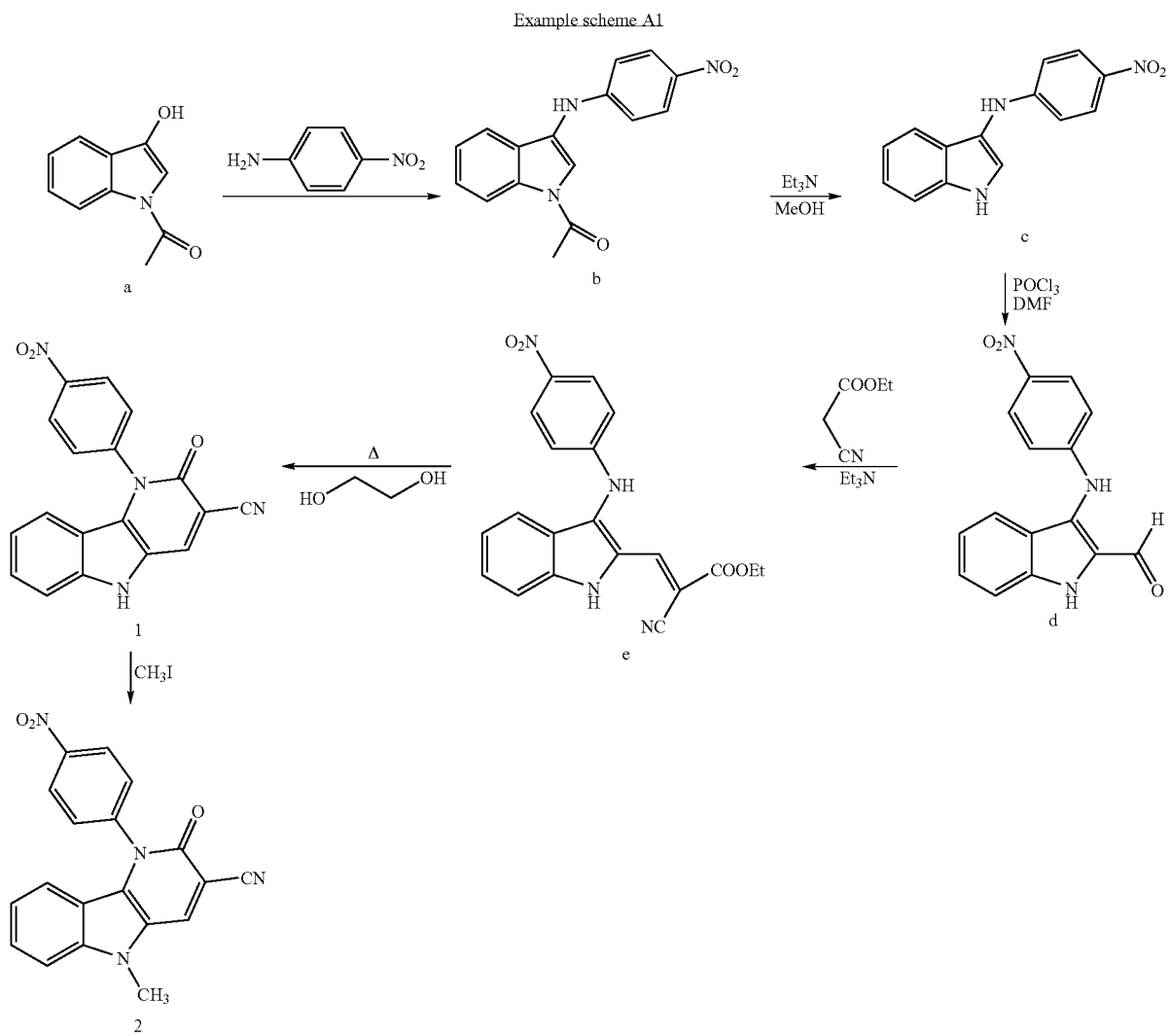

The synthesis of compounds (f) and (g) started from the commercially available 1-acetyl-3-hydroxyindole (a). Condensation of intermediate (a) with 4-nitroaniline, under refluxing conditions in acetic acid, yielded 3-((4-nitrophenyl)amino)indole (b) (Valezheva et al.; Chem.Heterocycl.Compd.(Engl.Transl.); 14; 1978; 757,759,760; Khim.Geterotsikl. Soedin.; 14; 1978; 939). Deacylation of intermediate (b) with lation using methyl iodide led to compound (2) (5-methyl-1-(4-nitro-phenyl)-2-oxo-2,5-dihydro-1H-pyrido[3,2-b]indole-3-carbonitrile).

More in particular, to a mixture of N-acetyl-3-hydroxyindole (a) (0.114 mol, 20 g) in acetic acid (150 ml), was added 4-nitroaniline (1.5 equiv., 0.171 mol, 23.65 g). The mixture was heated at reflux for 5 hours and cooled to room temperature. An orange precipitate was filtered off and washed with isopropanol and diisopropyl ether, affording intermediate b [S. Yu. Ryabova, N. Z. Tugusheva, L. M. Alekseeva, V. G. Granik *Pharmaceutical Chemistry Journal* 1996, 30, 472-477] (20.71 g, yield=62%, purity(LC)>98%).

Intermediate b (0.070 mol, 20.71 g) was mixed with methanol (200 ml) and triethylamine (3 equiv., 0.210 mol, 21.27 g) and the mixture was heated at reflux for 4 hours, cooled to room temperature and evaporated under reduced pressure to a dry powder. The crude product c [S. Yu. Ryabova, N. Z. Tugusheva, L. M. Alekseeva, V. G. Granik *Pharmaceutical Chemistry Journal* 1996, 30, 472-477] (purity(LC)>95%) was used as such in the next step.

To ice-cooled N,N-dimethylformamide (hereinafter referred to as DMF) (50 ml) was added dropwise phosphorus oxychloride (3 equiv., 0.210 mol, 32.22 g) keeping the internal temperature <10° C. and the cooled mixture was stirred for 1 hour. Then, a solution of c in DMF (100 ml) was added dropwise, keeping the reaction temperature <10° C. during the addition. The ice-bath was removed and the reaction mixture was stirred at room temperature for 1.5 hours. The mixture was poured into ice-water (1 liter) and then heated overnight at 60° C. and cooled to room temperature. The precipitate was isolated by filtration, washed successively with water, isopropanol and diisopropyl ether to afford intermediate d [S. Yu. Ryabova, N. Z. Tugusheva, L. M. Alekseeva, V. G. Granik *Pharmaceutical Chemistry Journal* 1996, 30, 472-477] (15.93 g, yield=81%, purity (LC)>95%).

To a mixture of d (0.056 mol, 15.93 g) in isopropanol (ISOmI) was added triethylamine (1.5 equiv., 0.085 mol, 8.59 g) and ethyl cyanoacetate (0.068 mol, 7.69 g). The mixture was heated at reflux for 2 hours, cooled to room temperature, filtered and the residue was successively washed with isopropanol and diisopropyl ether to afford intermediate e [S. Yu. Ryabova, L. M. Alekseeva, B. G. Granik *Chemistry of Heterocyclic Compounds* 2000, 36, 301-306] (16.42 g, yield=78%, purity(LC)>95%).

A stirred suspension of d (0.043 mol, 16.42 g) in ethyleneglycol (200 ml) was heated at reflux for 2 hours and cooled to room temperature. The precipitate was isolated by filtration and washed successively with isopropanol and diisopropyl ether. Crude compound 1 was crystallised from DMF/water as follows: the crude precipitate was dissolved in warm DMF (250 ml). To the warm solution, water (100 ml) was added and the solution was cooled to room temperature, allowing compound 1 to precipitate. The precipitate was isolated by filtration and washed successively with isopropanol and diisopropyl ether to afford compound 1[2] (10.52 g, yield=73%, purity (LC)>98%). $^1$H NMR (δ, DMSO-D6): 6.11 (1H, d, J≈8 Hz), 6.86 (1H, t, J≈8 Hz), 7.38 (1H, t, J≈8 Hz), 7.54 (1H, d, J≈8 Hz), 7.91 (2H, d, J=8.6 Hz), 8.55 (2H, d, J=8.6 Hz), 8.70 (1H, s), 12.00 (1H, br s).

To a mixture of compound 1 (6.05 mmol, 2.0 g) in DMF (20 ml) was added potassium carbonate (2 equiv., 12.11 mmol, 1.674 g) and methyl iodide (1.5 equiv., 9.08 mmol, 1.289 g) and the mixture was heated at reflux for 2 hours. The warm suspension was further diluted with DMF (40 ml). Water (40 ml) was added dropwise to the warm solution and the mixture was cooled to room temperature, allowing compound 2 to crystallise. The precipitate was isolated by filtration and washed successively with isopropanol and diisopropyl ether, affording compound 2 (2.085 g, yield=91%, purity (LC)>98%). $^1$H NMR (δ, DMSO-D6): 3.93 (3H, s), 6.12 (1H, d, J≈8 Hz), 6.89 (1H, t, J≈8Hz), 7.45 (1H, t, J≈8Hz), 7.64 (1H, d, J≈8Hz), 7.89 (2H, d, J=8.5 Hz), 8.54 (2H, d, J=8.5 Hz), 8.99 (1H, s)

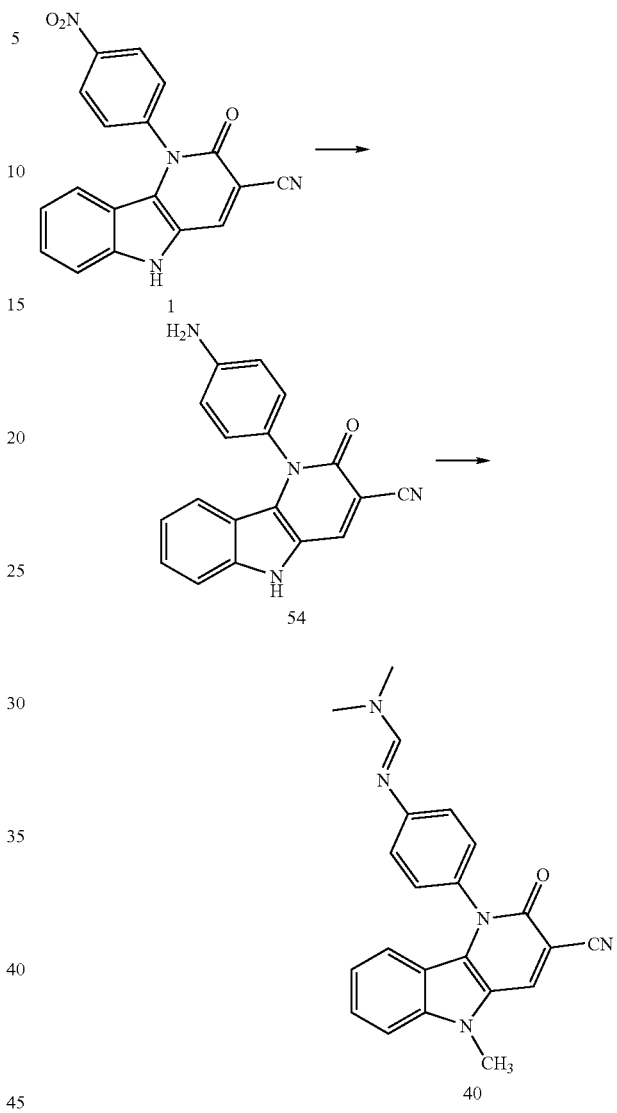

Example scheme A2

A solution of tin(II) chloride dihydrate (10 equiv., 0.060 mol, 13.54 g) in concentrated hydrochloric acid (20 ml) was added dropwise to a cooled (0° C.) solution of 1 (0.006 mol, 2 g) in ethanol 50 ml). The mixture was heated at 60° C. for 4 hours. The solution was cooled to room temperature and aqueous saturated sodium bicarbonate was added until pH>7. Compound 54 was isolated by filtration and washed successively with isopropanol and diisopropyl ether (1.23 g, yield=68% (purity(LC)>98%).

N,N-dimethylformamide dimethyl acetal (10 equiv., 3.33 mmol, 396 mg) was added to a mixture of compound 54 (0.333 mmol, 100 mg) in DMF (1 ml). The reaction mixture was heated at reflux for 1 hour. After cooling, the reaction mixture was cooled to room temperature, the solution was diluted with diisopropyl ether and stirred for ½ hour. The precipitate was isolated by filtration and washed with diisopropyl ether affording compound 40 (103 mg, yield=84 %, purity (LC)=96%).

Example scheme A4

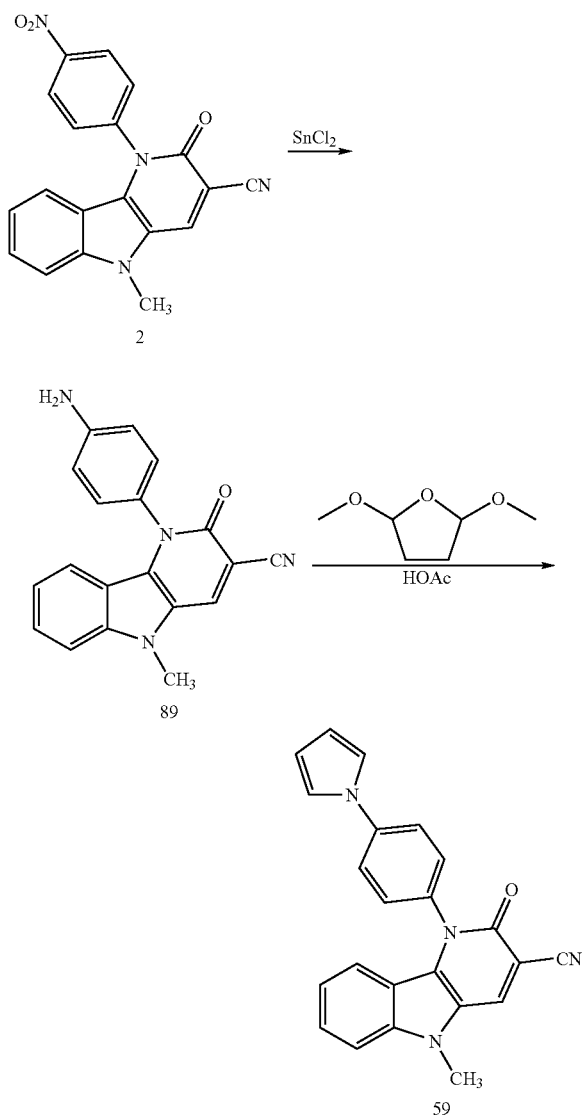

Example scheme A6

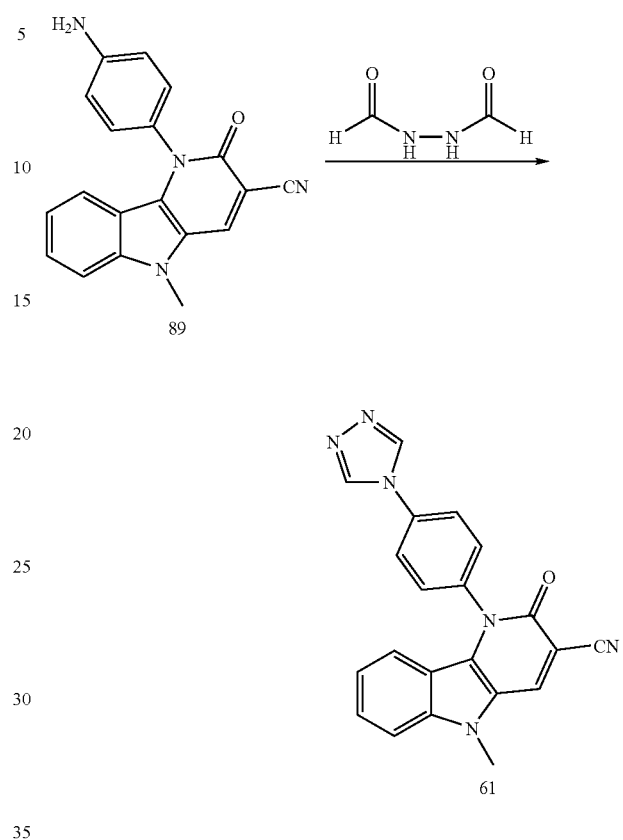

To a stirred solution of 7 (0.312 mmol, 107 mg) in ethanol (1 ml), a solution of tin(II) chloride dihydrate (3.5 equiv., 1.09 mmol, 245 mg) in concentrated hydrochloric acid (0.4 ml) was added and the reaction mixture was stirred at 60° C. for 2 hours. The reaction mixture was diluted with water and sodium bicarbonate was added until pH>7. The precipitate was isolated by filtration. The precipitate was washed with isopropanol and diisopropyl ether affording crude compound 89 that was used as such in the next step.

A solution of 2,5-dimethoxytetrahydrofuran (160 mg, 1.21 mmol, 2.9 equiv.) in acetic acid (2.5 ml) was added dropwise to a solution of the amine 89 (132 mg, 0.42 mmol) in acetic acid (5 mL) at 90° C. The mixture was stirred at 90° C. for 5 minutes and cooled to room temperature. The precipitate was filtered and washed with water. 130 mg brown solid was obtained. The crude product was further purified by preparative HPLC, affording compound 59 (63 mg, yield=41 %, purity (LC)=94%) as brown solid.

To a mixture of the amine 89 (104 mg, 0.33 mmol) in pyridine (3 ml) was added diformylhydrazine (87 mg, 0.99 mmol), followed by trimethylsilyl chloride (539 mg, 4.96 mmol) and triethylamine (234 mg, 2.32 mmol) dropwise. The reaction was heated at 100° C. for 2.5 hours and cooled to room temperature. The mixture was concentrated and co-evaporated with toluene. The resulting residue was taken up into methanol and filtered. The filtrate was concentrated to give 110 mg of a yellow solid. The crude product was purified by preparative HPLC affording compound 61 as a bright-yellow solid (50 mg, yield=41%).

Example scheme A7

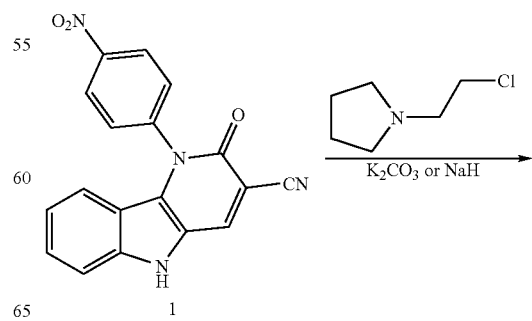

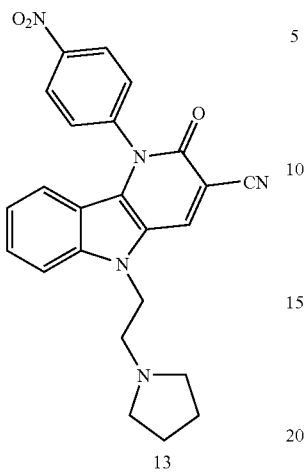

13

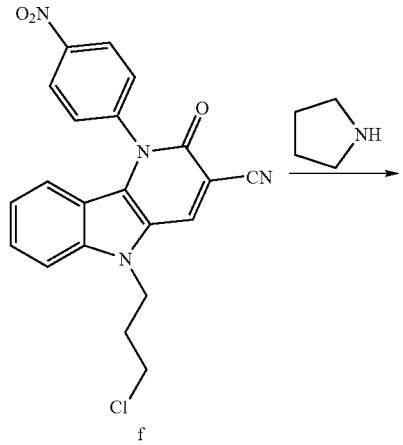

f

Method A: To a stirred solution of compound 1 (0.6 mmol, 0.200 g) in DMF (15 ml) was added potassium carbonate (3 equiv., 1.8 mmol, 0.248 g) and 1-(2-chloroethyl)-pyrrolidine hydrochloride (1.5 equiv., 0.9 mmol, 0.152 g) and the mixture was heated at reflux for 5 hours. The mixture was cooled to room temperature, water was added and the precipitate was isolated by filtration and washed successively with isopropanol and diisopropyl ether to afford compound 13 (0.192 g, yield=75%, purity(LC)>95%).

Method B: To a stirred mixture of compound 1 (6.1 mmol, 2.00 g) in DMF (20 ml) was added-under $N_2$-atmosphere at room temperature-sodium hydride (13 mmol, 0.538 g 60%). The reaction mixture was stirred at room temperature for 30 min and 1-(2-chloroethyl)pyrrolidine (6.6 mmol, 1.13 g) was added portionwise. The mixture was stirred overnight at room temperature. The solvent was removed under reduced pressure, water was added the aqueous solution was extraction with ethylacetate (3x). The organic phase was dried (MgSO$_4$), filtered and the solvent was removed under reduced pressure. The crude product was purified on silica (dichloromethane/methanol 90/10) to yield compound 13 (1.023 g, yield=40%(LC), purity>98%).

Example scheme A8

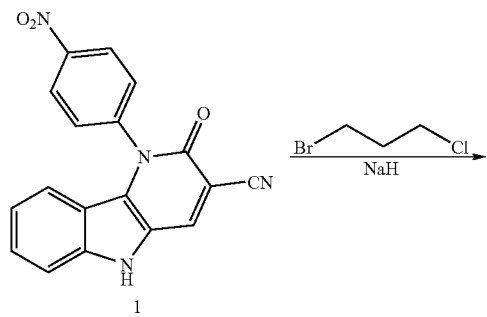

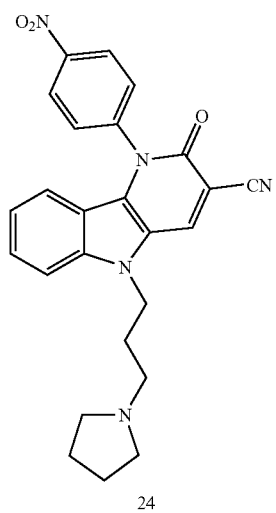

24

To a mixture of compound 1 (3 mmol, 1.00 g) in DMF (25 ml), was added sodium hydride (1.2 equiv., 3.6 mmol, 172 mg of 50% NaH in mineral oil) and the mixture was heated for 1 hour to 50° C. The mixture was cooled to room temperature and 1-bromo-3-chloropropane (1.5 equiv. 4.5 mmol, 0.702 g) was added. The reaction mixture was stirred overnight at room temperature. The reaction mixture containing intermediate f was used as such in the next step.

Pyrrolidine (1.5 equiv., 0.909 mmol, 0.065 g) was added to 5 ml of the reaction mixture of the former step containing intermediate f (0.606 mmol) and the mixture was heated for 5 hours at 70° C. The reaction mixture was cooled to room temperature, precipitated with water and successively washed with isopropanol and diisopropyl ether. Purification by preparative HPLC gave compound 24 (0.040 g, yield=15%, purity (LC)>95%).

Example scheme A9

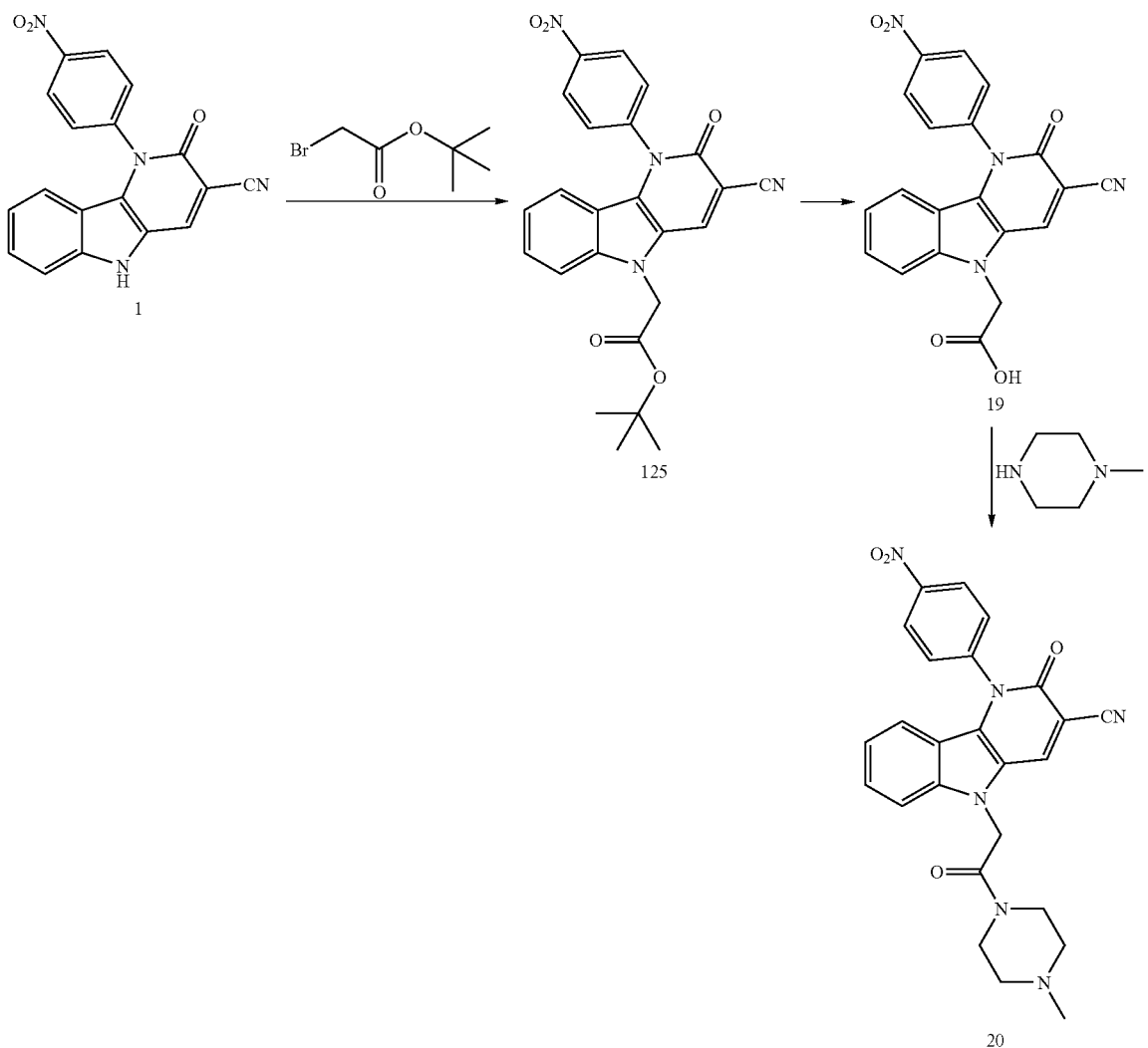

To a stiffed mixture of compound 1 (2 mmol, 0.660 g) in DMF (7.5 ml) was added potassium carbonate (6 mmol, 0.828 g) and tert-butyl-2-bromoacetate (2 equiv., 4 mmol, 0.776 g) and the mixture was heated to reflux for 1 hour. Compound 125 was not isolated and used as such in the next step.

To the crude reaction mixture of compound 18 was added 12 N hydrochloric acid until pH=0-1. The mixture was heated to reflux for 1 hour, cooled to room temperature and precipitated with water. The precipitate was isolated by filtration and washed successively with water, isopropanol and diisopropyl ether to afford compound 19 (0.495 g, yield=64%, purity>98%).

To a mixture of compound 19 (0.1 3mmol, 0.0050 g) in DMF (4 ml) was added 1,1'-carbonylduimidazole and the mixture was stirred at room temperature for 2 hours. 1-Methylpiperazine was added and the mixture was stirred overnight at room temperature. Compound 20 precipitated on the addition of water and the product was isolated by filtration.

The precipitate was successively washed with isopropanol and diisopropyl ether to give 20 (0.039g, yield=63%, purity (LC)>95%).

Example scheme A10

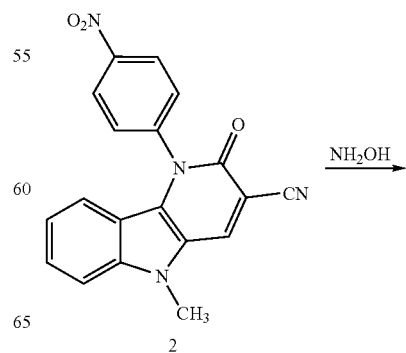

-continued

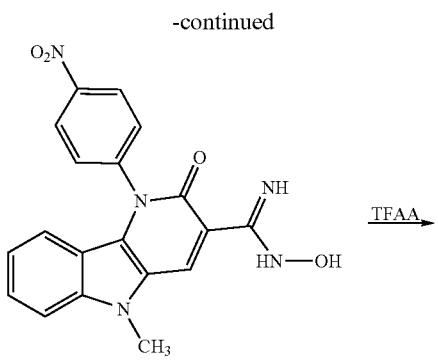
70

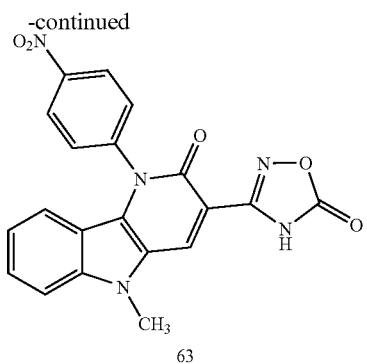
63

To a stirred mixture of compound 70 (0.265 mmol, 0.100 g) in acetonitrile (15 ml) was added 1,1'-carbonyldiimidazole (0.318 mmol, 0.052 g) and the mixture was heated at reflux overnight. The mixture was cooled to room temperature, water was added and extracted with dichloromethane (3×30 ml). After evaporation of the aqueous layer, compound 63 was obtained (0.058 g, yield=45%, purity=83%).

Example scheme A12

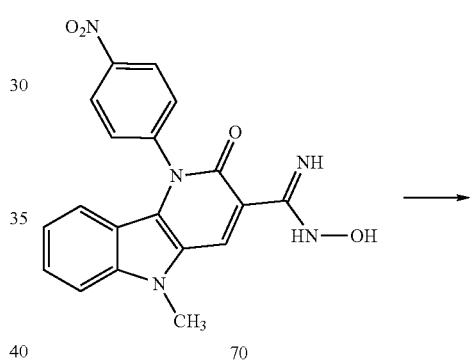
70

72

To a mixture of compound 2 (2.90 mmol, 1.00 g) in ethanol (20 ml) was added hydroxylamine hydrochloride (5 equiv., 14.52 mmol, 1.01 g) and potassium carbonate (6 equiv., 17.43 mmol, 2.408 g). The mixture was heated at reflux for 24 hours, cooled to room temperature and the precipitate was isolated by filtration and successively washed with water, isopropanol and diisopropyl ether to afford compound 70 (0.933 g, yield=81 %, purity (LC)=94%).

To a mixture of compound 70 (0.265 mmol, 0.100 g) in pyridine (15 ml) was added trifluoroacetic anhydride (1.2 equiv., 0.318 mmol, 0.038 g) and triethylamine (1.5 equiv., 0.400 mmol, 0.040 g) and the mixture was heated at reflux for 12 hours. The solvent was removed under vacuum and the residue was purified by chromatography over silica gel with dichloromethane/methanol (95/5) to afford compound 72 (0.044 g, yield=33%, purity (LC)=91%).

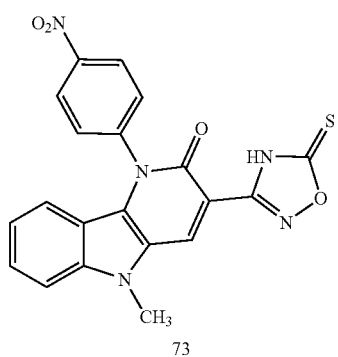
73

Example scheme A11

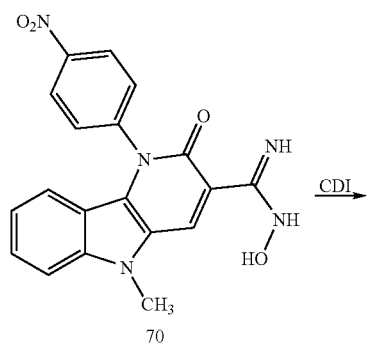
70

To a stirred mixture of compound 70 (0.265 mmol, 0.100 g) in acetonitrile (15 ml) was added 1,1'-thiocarbonyldiimidazole (0.318 mmol, 0.057 g) and 1,8-diazo-bicyclo[5.4.0]undec-7-ene (0.318 mmol, 0.048 g) and the mixture was heated at 80° C. for 1 hour. The solvent was removed under reduced pressure, water was added and the mixture was acidified with 1N hydrochloric acid to pH=1. The precipitate was filtered and washed successively with water, isopropanol and diisopropyl ether. The precipitate was recrystallized from DMF/water and the crystals where isolated by filtration and washed successively with water, isopropanol and diisopropyl ether to afford compound 73 (0.063 g, yield=54%, purity (LC)=96%).

Example scheme A13

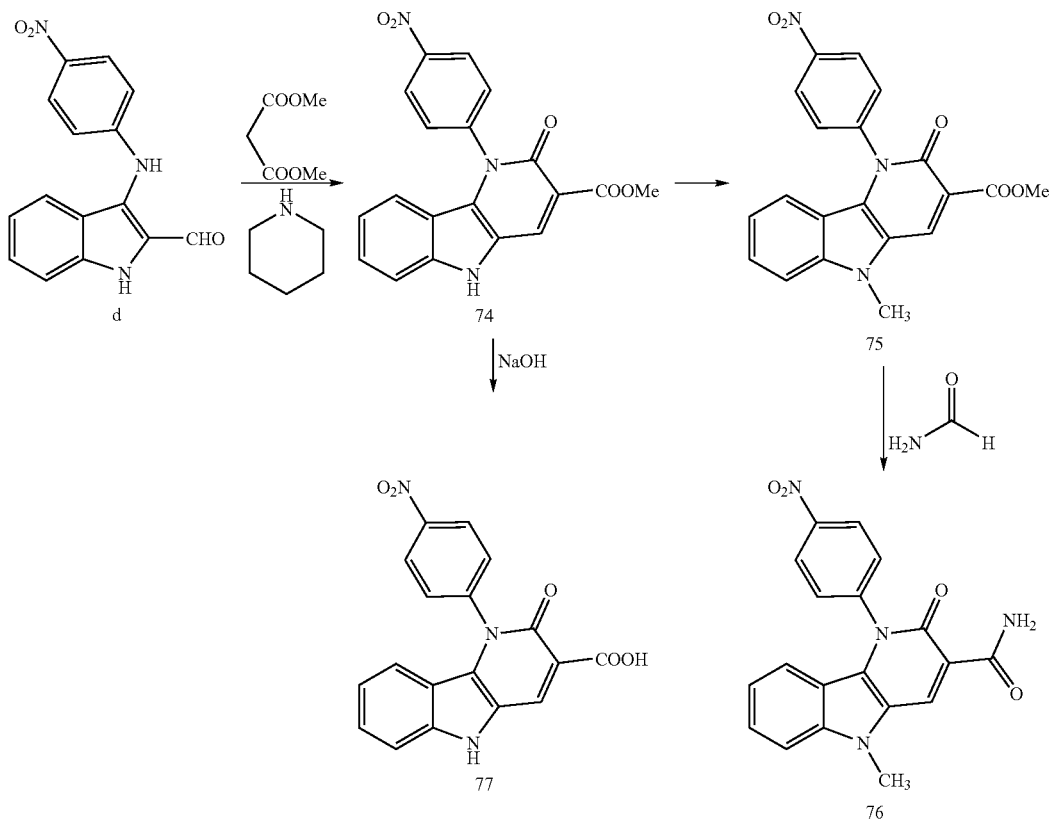

To a mixture of intermediate d (7.43 mmol, 2.091 g) in methanol (50 ml) was added dimethylmalonate (1.2 equiv., 8.92 mmol, 1.179 g) and piperidine (catalytic) and the mixture was heated at reflux for 5 hours. The precipitate was filtered off and successively washed with isopropanol and diisopropyl ether to yield compound 74 (1.53 g, yield=54 %, purity (LC)=95%)

To a mixture of compound 74 (3.48 mmol, 1.265 g) in DMF (35 ml) was added methyliodide (1.5 equiv., 5.22 mmol, 0.741 g) and potassium carbonate (2 equiv., 6.963 mmol, 0.962 g). The mixture was heated to 100° C. for 2 hours, cooled to room temperature and, upon the addition of water, a precipitate was formed. The precipitate was filtered of and successively washed with isopropanol and diisopropyl ether to yield compound 75 (1.213 g, yield=92%, purity (LC)=98%).

To a mixture of compound 75 (0.53mmol, 0.200 g) in DMF (5 ml) was added sodium methoxide (2 equiv., 1.06 mmol, 0.057 g) dissolved in methanol (2ml) and formamide (10 equiv., 5.30 mmol, 0.239 g) and the mixture was heated to 100° C. for 1 hour. The reaction was cooled to room temperature and, upon the addition of water, a precipitate was formed. The precipitate was filtered and successively washed with isopropanol and diisopropyl ether to yield compound 76 (0.150 g, yield=78%, purity(LC)=97%)

A solution of potassium hydroxide (1.10 mmol, 0.062 g) in water (3 ml) was added to a stirred solution of compound 74 in methanol (7 ml) and the mixture was heated at reflux for 2 hours. The mixture was cooled to room temperature and acidified with 2N hydrochloric acid until the product precipitated. The precipitate was isolated by filtration and dried overnight in a vacuum oven at 50° C. to yield compound 77 (0.110 g, yield=40%, purity (LC)>98%).

Example scheme A14

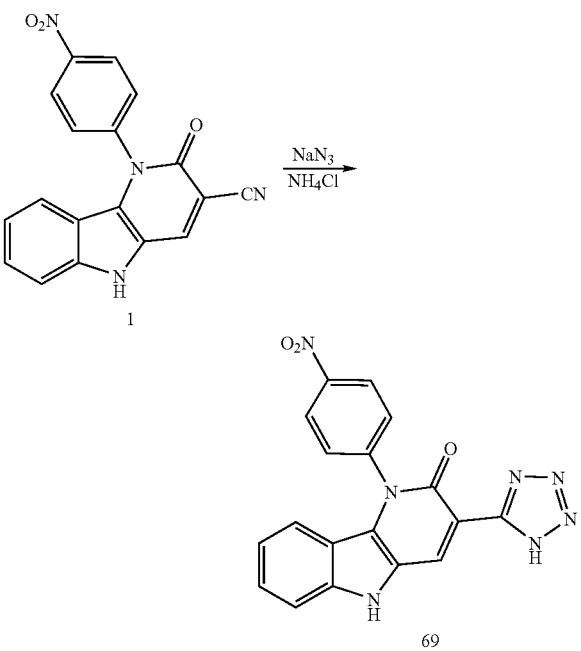

Compound 1 (0.303 mmol, 100 mg) was dissolved in DMF (2 ml). Sodium azide (15 equiv., 4.545 mmol, 294 mg) and ammonium chloride (15 equiv., 4.545 mmol, 240 mg) were added in equal portions over 6 days while the reaction mixture was stirred at 125° C. The reaction mixture was cooled to room temperature, poured into water (30 ml) and stirred at room temperature for ½ hour. The precipitate was isolated by filtration. The precipitate was washed with water. Recrystallisation from acetonitrile/acetone afforded compound 69 (23 mg, yield=20%, purity (LC)>95%).

Example scheme A15

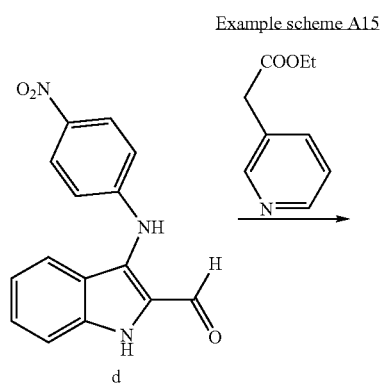

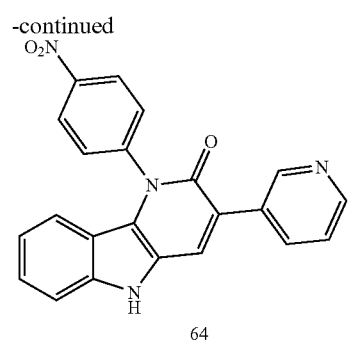

To a mixture of intermediate d (1.00 mmol, 0.281 g) in THF (10 ml), was added potassium tert-butoxide (1.10 equiv., 1.10 mmol, 0.123 g) and ethyl 3-pyridylacetate (1.00 equiv., 1.00 mmol, 0.165 g). The mixture was stirred and heated at 90° C. overnight. The reaction mixture was concentrated. The residue was dissolved in ethyl acetate and washed with water. The organic phase was dried with magnesium sulphate, filtered and evaporated to dryness. The residue was purified with preparative HPLC, affording compound 64 (0.008 g, yield=2%, purity (LC)>50%).

Example scheme B1

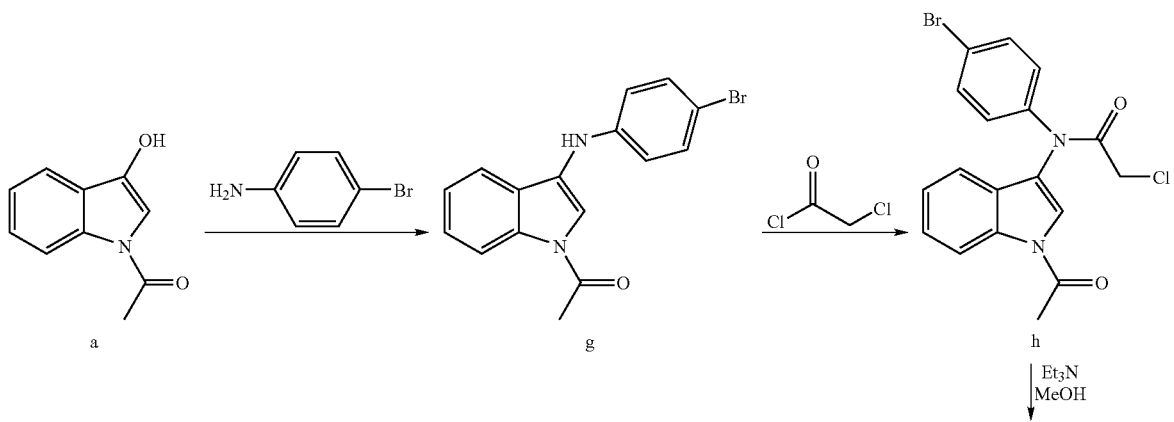

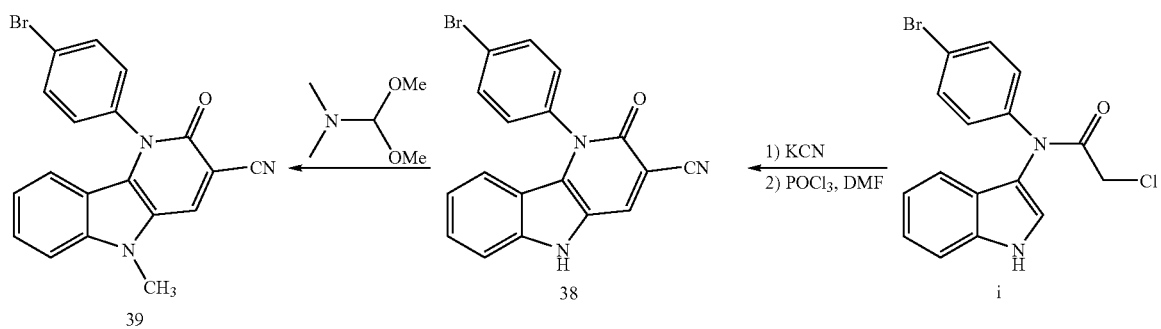

To a mixture of N-acetyl-3-hydroxyindole (0.057 mol, 10.00 g) in toluene (100 ml), 4-bromoaniline (1.1 equiv., 0.063 mol, 10.80 g) and a catalytic amount of p-toluenesulfonic acid were added. The reaction mixture was heated at reflux for 4 hours with azeotropic removal of water. Upon cooling to room temperature, intermediate g crystallised. The precipitate was isolated by filtration and washed with toluene, affording intermediate g (9.60 g, yield=51%, purity (LC)>95%).

A mixture of g (0.056 mol, 18.53 g) in chloroacetyl chloride (85 ml) was heated at reflux for 15 minutes. The reaction mixture was concentrated under reduced pressure. Isopropanol (50 ml) was added to the residue and the reaction mixture was heated to reflux for 10 minutes. The reaction mixture was cooled, the precipitate was filtered and washed with isopropanol, affording intermediate h (17.00 g, yield=74%, purity (LC)=95%).

To a mixture of intermediate h (0.0419 mol, 17.00 g) in methanol (170 ml), triethylamine (1.2 equiv., 0.0503 mol, 5.09 g) was added. The reaction mixture was heated at reflux for 1 hour. The cooled reaction mixture was filtered. The precipitate was washed with diethyl ether, affording intermediate i (13.41 g, yield=88%, purity (LC)=95%).

In a first reaction vessel, potassium cyanide (2.50 equiv., 0.0965 mol, 6.28 g) was added to a solution of intermediate i (0.0386 mol, 14.03 g) in DMF (140 ml). The reaction was heated at reflux for 3 hours and cooled to room temperature. In a second reaction vessel, dry DMF (45 ml) was cooled to 0° C. Phosphorus oxychloride (2.5 equiv., 0.0965 mol, 14.8 g) was added dropwise keeping the internal temperature <10° C. and the reaction mixture was stirred at 0° C. for an additional ½ hour. The contents of first reaction vessel were then added dropwise to the stirred POCl$_3$-DMF complex in the second reaction vessel while the temperature was kept <10° C. The reaction mixture was stirred overnight at room temperature, poured into water (860 ml) and stirred at 70° C. for 6 hours. The cooled reaction mixture was filtered. The precipitate was washed with isopropanol and diisopropyl ether, affording compound 38 (12.18 g, yield=87%, purity (LC)>95%).

N,N-Dimethylformamide dimethyl acetal (10 equiv., 0.233 mol, 27.72 g) was added to a solution of compound 38 (0.0233 mol, 8.49 g) in DMF (85 ml). The reaction mixture was heated at reflux for 1 hour. The reaction mixture was cooled to room temperature, poured into water (500 ml) and stirred for ½ hour. The precipitate was isolated by filtration, washed with water and diisopropyl ether, affording compound 39 (4.54 g, yield=51%, purity (LC)=95%). $^1$H NMR (δ, DMSO-D6): 3.92 (3H, s), 6.10 (1H, d, J≈8 Hz), 6.91 (1H, t, J≈8 Hz), 7.44 (1H, t, J≈8 Hz), 7.52 (2H, d, J=8.6 Hz), 7.63 (1H, d, J≈8 Hz), 7.91 (2H, d, 8.6Hz), 8.95 (1H, s).

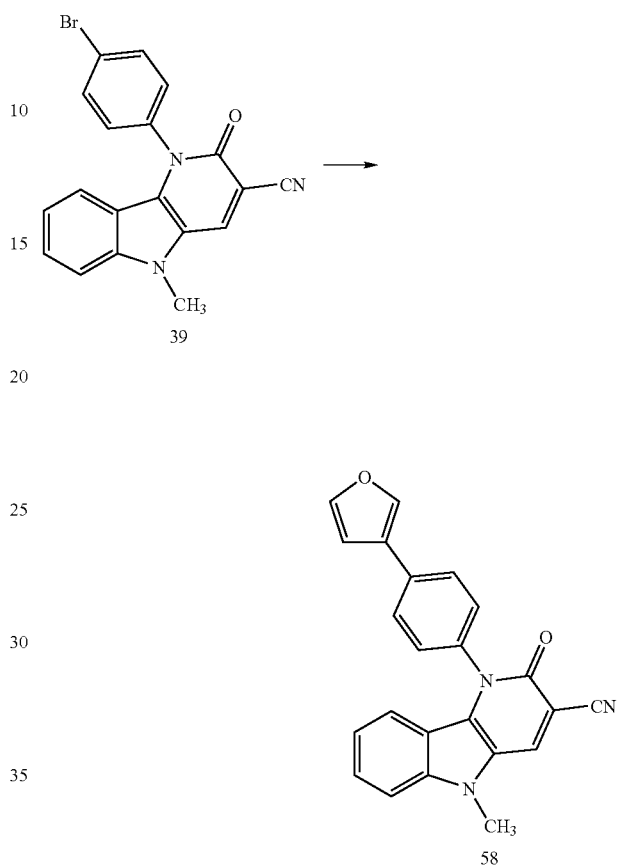

Example scheme B2

39

58

Tris(dibenzylideneacetone)dipalladium(0) (0.1 equiv., 0.026 mmol, 24 mg) was added to a solution of tri(t-butyl) phosphine in toluene (0.24 equiv., 0.0635 mmol, 0.4 M, 159 µl) in a sealed tube. Dry THF (3 ml) was added and the reaction mixture was stirred under nitrogen at room temperature for 10 minutes. In a second sealed tube, compound 39 (0.264 mmol, 100 mg), 3-furylboronic acid (2 equiv., 0.53 mmol, 59 mg) and potassium fluoride (3.3 equiv., 0.87 mmol, 51 mg) were mixed and to this stirred suspension, the solution from the first sealed tube was added with a syringe. The reaction mixture was stirred under nitrogen at room temperature for 2 days. The reaction mixture was filtered over decalite and the decalite was washed with dichloromethane (100 ml). The combined filtrates were concentrated in vacuo, affording a dark brown oil. This residue was dissolved in DMF (2 ml), poured into water (20 ml) and stirred at room temperature for ½ hour. The precipitate was isolated by filtration, washed with water, isopropanol and diisopropyl ether and further purified by preparative HPLC, affording compound 58 (25 mg, yield=26%, purity (LC)>95%).

Example scheme C1

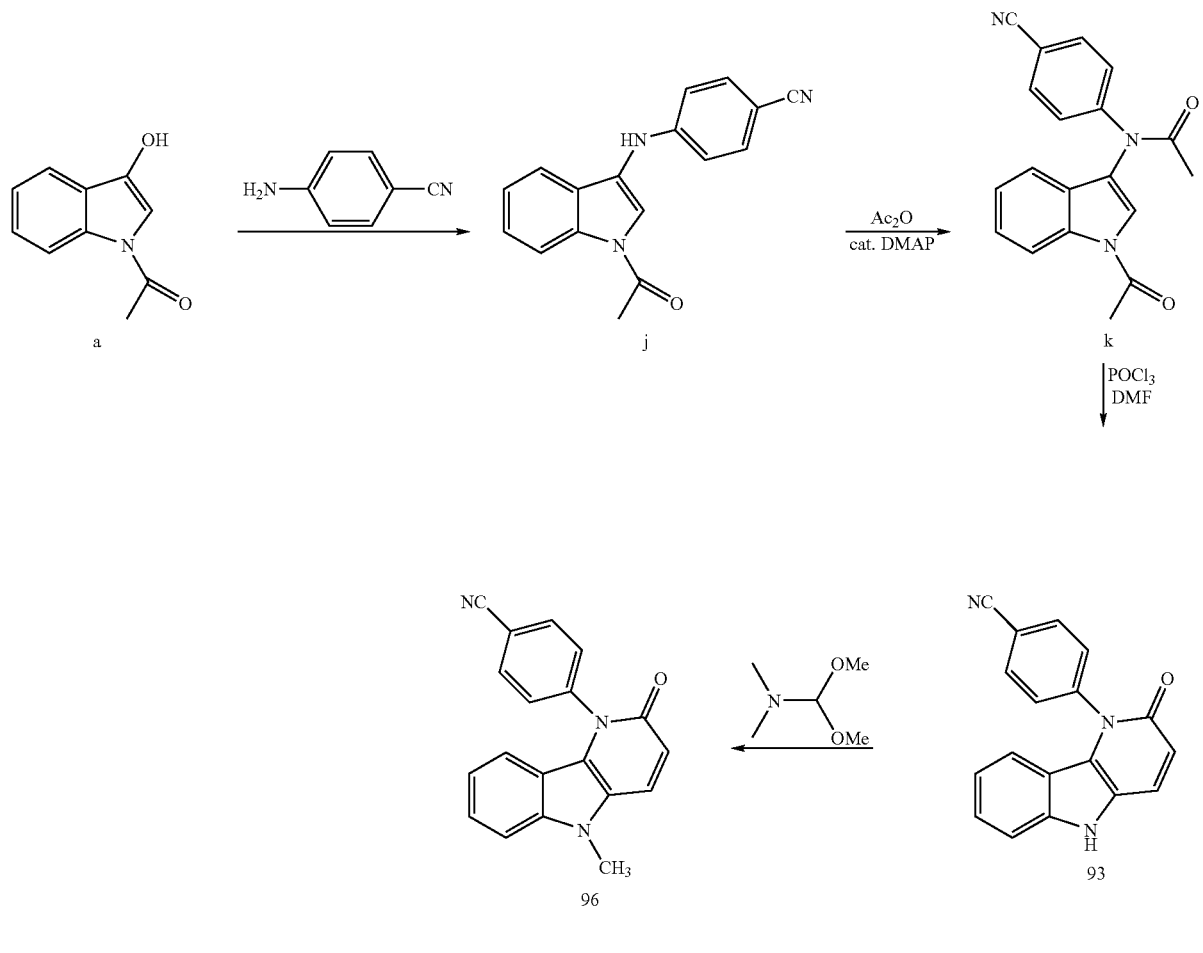

To a mixture of N-acetyl-3-hydroxyindole a (85.624 mmol, 15 g) in acetic acid (150 ml) was added 4-aminobenzonitrile (1.5 equiv., 0.128 mol, 15.17 g) and the mixture was heated at reflux for 4 hours. The reaction mixture was cooled on ice for 1 hour, allowing the reaction product to crystallize. The precipitate was filtered off and washed successively with isopropanol and diisopropyl ether, affording intermediate j as a white powder (9.24 g, yield=58%, purity(LC)>98%).

To a mixture of intermediate j (0.053 mol, 14.7 g) in acetic anhydride (150 ml) was added a catalytic amount of dimethylaminopyridine, and the mixture was heated at reflux overnight. The solvent was removed under reduced pressure to give a black tar, containing intermediate k. The crude reaction mixture was used as such in the next step.

The crude mixture of intermediate k was dissolved DMF (200 ml) and cooled on an ice bath. To this stirred reaction mixture, a premixed solution (using cooling) of phosphorus oxychloride (5 equiv., 0.31 mol, 30ml) and DMF (50 ml) were added dropwise and stirring at 0° C. was continued for a few hours. Then, the contents of the reaction were poured into ice-water (1.5l) and heated at reflux overnight: The mixture was allowed to cool to room temperature, filtered and the precipitate was washed successively with water, isopropanol, diisopropyl ether affording compound 93 as black crystals (12.4 g, yield=81% (two steps), purity (LC)>98%)

To a mixture of compound 93 (0.043 mol, 12.4 g) in DMF (120 ml) was added N,N-dimethylformamide dimethyl acetal (5equiv., 0.217 mol, 29ml) and the mixture was heated at reflux. After 3 h another portion of N,N-dimethylformamide dimethyl acetal (5 equiv., 0.217 mol, 29 ml) was added and the reaction mixture was heated at reflux overnight. The reaction mixture was poured into a mixture of water (800 ml) and acetic acid (10 ml) and stirred for 1 hour to give a black precipitate. The precipitate was filtered off and washed successively with water, isopropanol and diisopropyl ether affording compound 96 as a black powder (8.20 g, yield=63%, purity (LC)>98%). $^1$H NMR ($\delta$, DMSO-D6): 3.90 (3H, s), 6.06 (1H, d, J≈8 Hz), 6.61 (1H, d, J=9.60 Hz), 6.85 (1H, t, J≈8 Hz Hz), 7.31 (1H, t, J≈8Hz), 7.58 (1H, d, J≈8Hz), 7.72 (2H, d, J=8.3 Hz), 8.15→8.19 (3H, m)

Example scheme C2

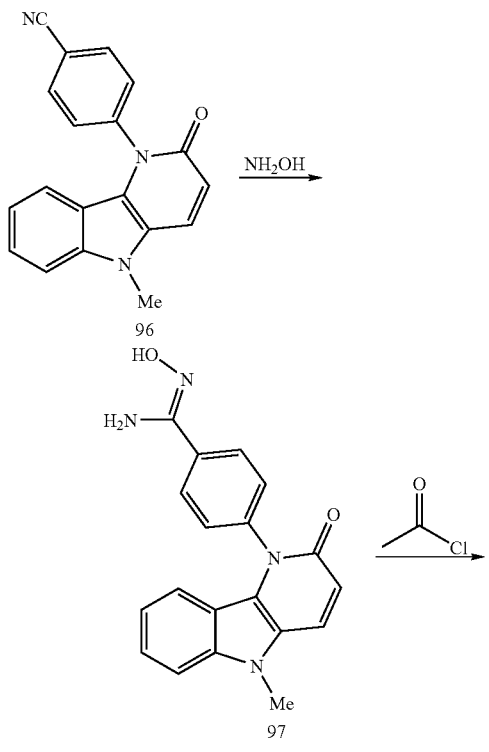

sium sulfate, filtered and the solvent was removed under reduced pressure. The product was purified by flash chromatography (eluent: dichloromethane/methanol: 9/1) affording compound 103 as orange crystals.

Example scheme C3

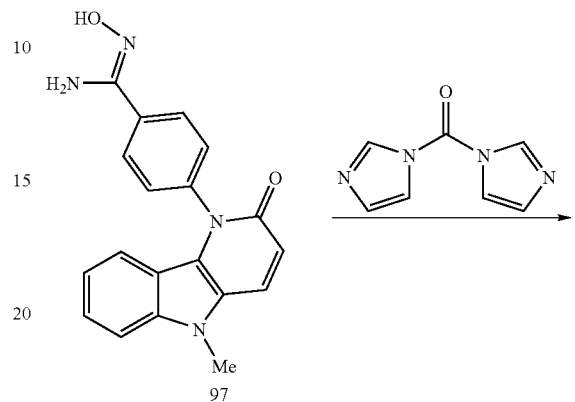

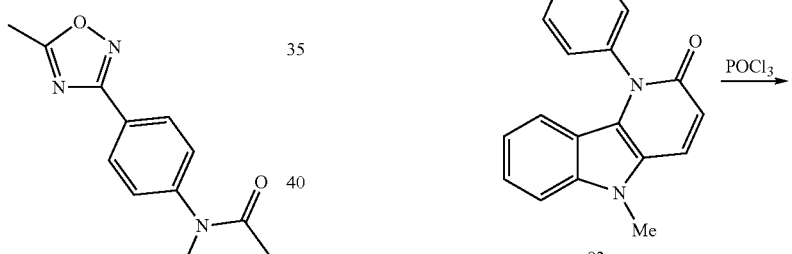

To a stirred solution of 96 (40.758 mmol, 12.2 g) in ethanol (130 ml) was added hydroxylamine hydrochloride (5 equiv., 0.143 mol, 9.91 g) and potassium carbonate (6 equiv., 0.171 mol, 23.6 g) and the mixture was heated at 70° C. overnight. The solvent was removed under reduced pressure. The residue was taken up in dichloromethane (250 ml) and water (1 l) and vigorously stirred for 1 hour. The mixture was filtered and the precipitate washed with water, isopropanol and diisopropyl ether affording compound 97 as a black powder (5.68 g, yield=60%, purity (LC)=90%)

To a stirred solution of compound 97 (0.0003 mol, 100 mg) in pyridine (2 ml), was added acetyl chloride (1.2 equiv., 0.00036 mol, 28 mg) and the reaction mixture was heated at reflux overnight. The solvent was removed under reduce pressure, the residue was taken up in dichloromethane (25 ml) and washed with brine. The organic layer was dried with magne-

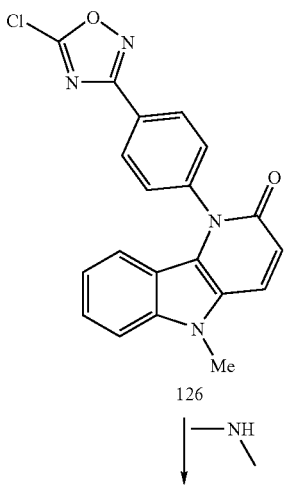

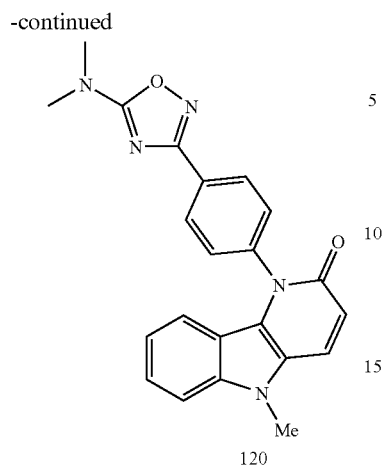

120

To a mixture of compound 97 (0.3 mmol, 100 mg) in acetonitrile (5 ml) was added 1,1'-carbonyldiimidazole (1.2 equiv., 0.36 mmol, 0.060 g) and stirred under heating (80° C.) for 6 hours. The solvent was removed under reduced pressure, the residue was taken up in dichloromethane (25 ml) and brine (25 ml) and vigorously stirred for 30 min. Filtration of the solvent mixture afforded compound 83 (0.067 g, yield=62%, purity (LC)>98%).

A flask containing compound 83 (0.1 g, 0.279 mmol) was equipped with a CaCl$_2$ tube. Phosphorus oxychloride (3 ml) was added dropwise and the mixture was heated at reflux overnight. The reaction mixture was poured into ice-water (150 ml) and stirred for 1 hour. The mixture was filtered and washed with water, isopropanol, and diisopropyl ether affording compound 126 (0.080 g, yield=71%, purity (LC)=93%).

To a stirred solution of compound 126 (0.090 g, 0.239 mmol) in acetonitrile (4 ml) was added methylamine 40% in water (10 equiv, 2.390 mmol, 269 mg) and the reaction mixture was stirred at room temperature for 2 hours. The solvent was removed under reduced pressure affording compound 120 (0.091 g, yield=99%, purity>95%).

Example scheme C4

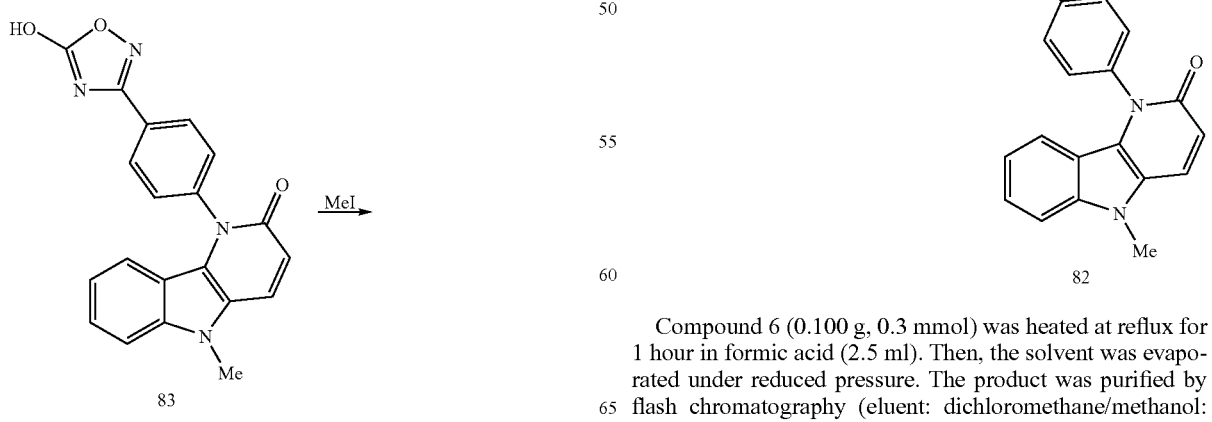

83

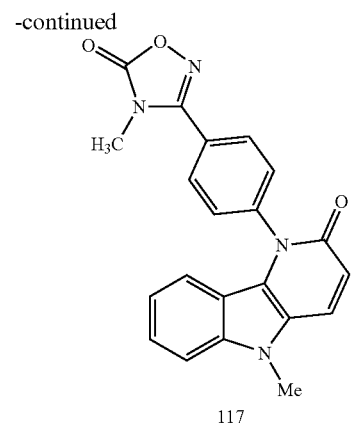

117

To a mixture of compound 83 (0.279 mmol, 0.100 g) and potassium carbonate (2 equiv., 0.519 mmol, 0.071 g) in DMF (5 ml) was added dropwise methyl iodide (2 equiv., 0.519 mmol, 0.074 g) in DMF (5 ml). The reaction mixture was stirred a room temperature for 5 h. The solvent was removed under reduced pressure and the residue was mixed with water (100 ml) and vigorously stirred for 1 hour. The precipitate was filtered off and washed with water, isopropanol and diisopropyl ether affording compound 117 (0.072 g, yield=74%, purity (LC)=90%).

Example scheme C5

97

$\xrightarrow{\text{HCOOH}}$

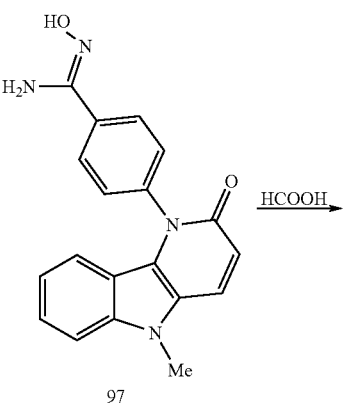

82

Compound 6 (0.100 g, 0.3 mmol) was heated at reflux for 1 hour in formic acid (2.5 ml). Then, the solvent was evaporated under reduced pressure. The product was purified by flash chromatography (eluent: dichloromethane/methanol: 9/1) affording compound 82 (0.022 g, yield=16%, purity (LC)=77%).

Example scheme C6

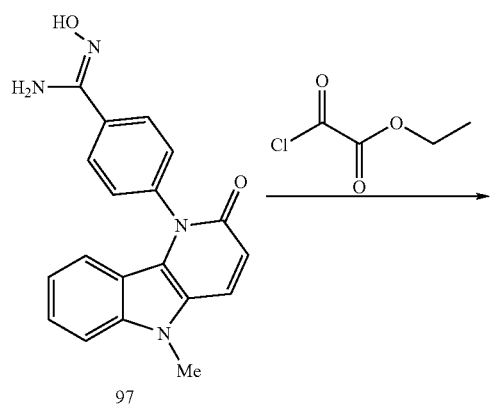

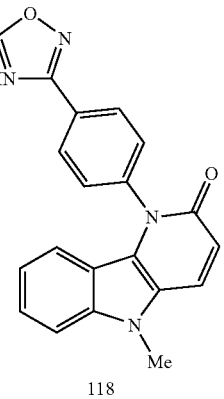

To a mixture of compound 97 (0.1 g, 0.3 mmol) in acetonitryle (3 ml) was added 1,1'-thiocarbonyldiimidazole (1.2 equiv., 0.36 mmol, 0.064 g) and 1,8-diazabicyclo-[5.4.0]undec-7-ene (1.2 equiv., 0.36 mmol, 0.055 g) and the mixture was heated at reflux for 1 hour. The solvent was removed under reduced pressure and the residue was washed with water, isopropanol, diisopropyl ether affording compound 118 (0.081 g, yield=72%, purity (LC)>95%).

Example scheme C8

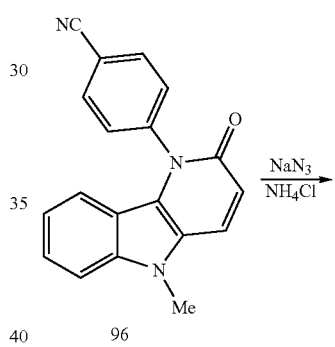

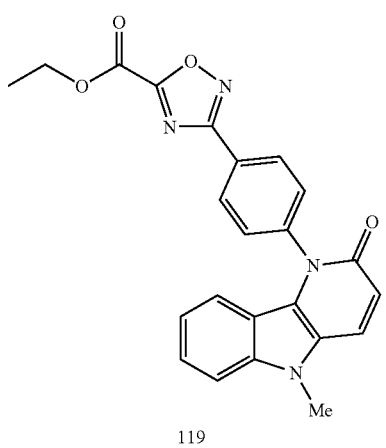

To a mixture of compound 97 (0.200 g, 0.6 mmol) and triethylamine (1.5 equiv., 0.9 mmol, 0.091 g) in THF (3 ml) was added dropwise a solution of ethyl oxalyl chloride (1.2 equiv., 0.72 mmol, 0.1 g) in THF (1 ml). The mixture was stirred at room temperature for 1.5 hour. Then, under argon atmosphere, tetrabutylammonium fluoride (0.3 equiv, 0.18 mmol, 0.048 g) was added and the mixture was stirred overnight. The reaction mixture was diluted with ethyl acetate (40 ml) and washed with water and brine. The organic layer was dried with magnesium sulfate, filtered and the solvent was removed under reduced pressure. The crude product was recrystallized from ethyl acetate/hexane, affording compound 119 as a yellow powder (0.006 g, yield 2%, purity (LC)>95%).

Example scheme C7

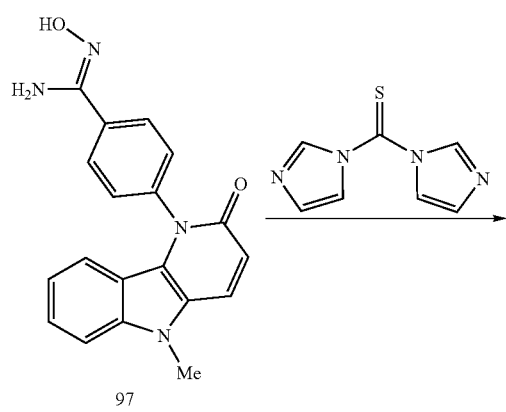

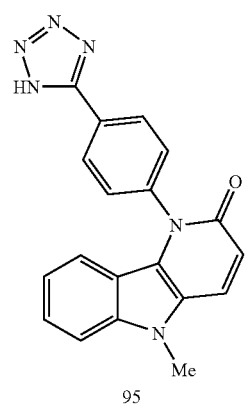

Compound 96 (0.175 mmol, 50 mg) was dissolved in DMF (2 ml). Sodium azide (10.4 equiv., 1.848 mmol, 120 mg) and ammonium chloride (11.6 equiv., 2.036 mmol, 108 mg) were added in 10 equal portions over 50 hour while the reaction mixture was heated at 125° C. The reaction mixture was cooled to room temperature. Then it was poured into ice-water (30 ml). The reaction mixture was acidified with 1 N hydrochloric acid and stirred at room temperature for 1 hour. A precipitate was isolated by filtration. The precipitate was washed with water, isopropanol and diisopropyl ether. The precipitate was purified by preparative HPLC, affording compound 95 (1 mg, yield 2%, purity (LC)>95%)

Example scheme C9

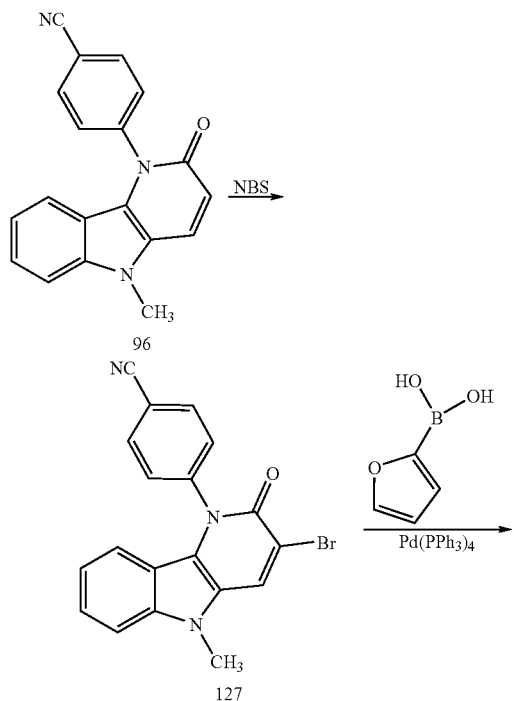

To a mixture of compound 96 (0.0083 mol, 2.5 g) in dichloromethane (50 ml) was added N-bromosuccinimide (1 equiv., 0.0083 mol, 1.48 g) and the mixture was stirred at room temperature for 4 hours. The solvent was removed under reduced pressure. The reaction mixture was dissolved in DMF (30 ml) and precipitated by the addition of water (150 ml). The precipitate was filtrated and washing with water, isopropanol, diisopropyl ether, affording compound 127 (2.59 g, yield=74%, purity (LC)=91%)

To a mixture of compound 127 (0.50 mmol, 0.190 g) in toluene (3 ml), ethanol (1 ml) and water (5 drops), was added potassium carbonate (1.20 equiv., 0.60 mmol, 0.083 g), tetrakis(triphenylphosphine)palladium(0) (0.10 equiv., 0.05 mmol, 0.058 g) and 2-Furylboronic acid (1.20 equiv., 0.60 mmol, 0.067 g). The mixture was stirred and heated at 100° C. overnight. The reaction mixture was concentrated in vacuo and the residue was dissolved in ethyl acetate and washed with water. The organic phase was dried with MgSO₄, filtered, and evaporated under reduced pressure. The residue was purified by chromatography using silica gel, affording compound 88 (yield=54%, purity=90%).

Example scheme C10

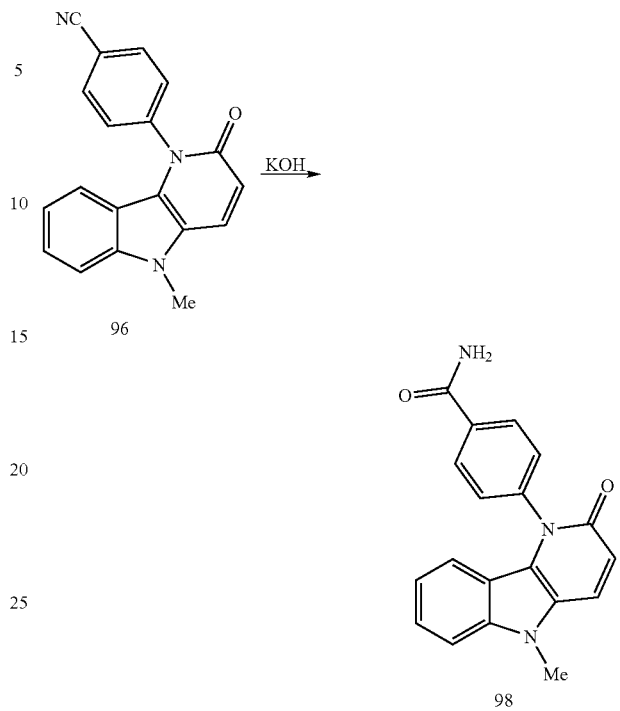

To a mixture of compound 96 (0.3344 mmol, 0.100 g) in ethanol (9 ml) and water (1 ml) was added potassium hydroxide (1 equiv., 0.3344 mmol, 0.019 g). The reaction mixture was heated at reflux overnight and the solvent was removed under reduced pressure. The residue was dissolved in dichloromethane, washed with water, dried with magnesium sulfate and filtered. The solvent was removed under reduced pressure affording compound 98 (0.055 g, yield=52%, purity (LC)>95%).

Example scheme C11

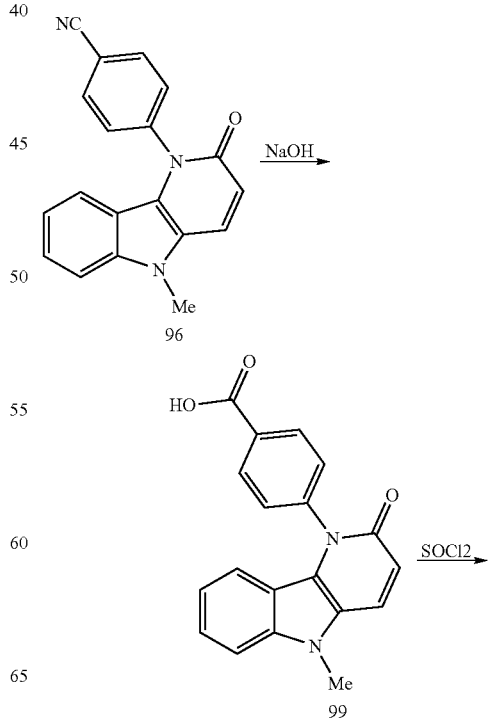

-continued

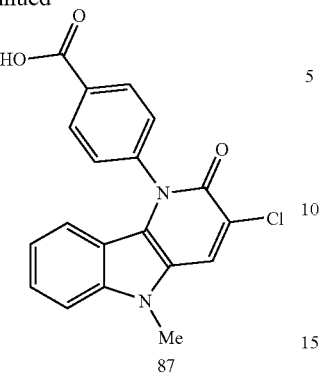

87

To a mixture of compound 96 (1.670 mmol, 0.5 g) in ethanol (5 ml) was added sodium hydroxide 50% in water (0.5 ml), and the mixture was heated at reflux overnight. The reaction mixture was diluted with water and 1N hydrochloric acid was added until pH=2 causing 99 to precipitate. The precipitate was filtered off, washed with water, and dried in a vacuum oven at 50° C. affording compound 99 as a brown powder (0.46 g, yield=87%, purity (LC)>95%).

To a mixture of compound 99 (0.628 mmol, 0.200 g) in dichloromethane (7 ml) was added thionylchloride (3 ml) in 3 portions over 24 h while the mixture was heated at reflux. The solvent was removed under reduced pressure and the residue was dissolved in ethanol (5 ml). To this stirred solution was added sodium hydroxide 50% in water (1 ml), and the mixture was stirred at room temperature for 1 hour. The reaction mixture was diluted with water and 1N hydrochloric acid was added until pH=2 causing compound 87 to precipitate. The precipitate was filtered off, washed with water, and dried in a vacuum oven at 50° C. affording 87 as a brown powder (0.033 g, yield=12%, purity (LC)=87%).

Example scheme C12

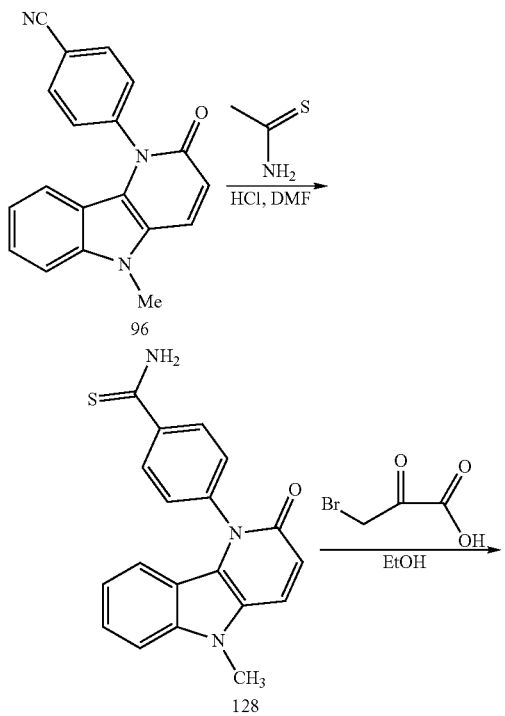

-continued

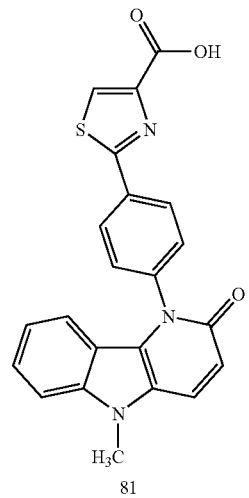

81

To a vigorously stirred solution of DMF (25 ml), saturated with hydrochloric acid, was added 96 (1 g, 3.34 mmol) and thioacetamide (2 equiv., 0.502 g, 6.7 mmol). The mixture was stirred at 60° C. for 12 hours. The mixture was added slowly to an aqueous saturated solution of $KHCO_3$ (50 ml). The aqueous solution was extracted with ethyl acetate (3×20 ml) and the combined fractions were dried ($MgSO_4$) and evaporated under reduced pressure to give compound 128 (500 mg, 45%) as a solid.

To a stirred solution of thioamide 128 (170 mg, 0.5 mmol) in ethanol (20 ml), bromopyruvic acid (1.2 equiv., 103 mg, 0.6 mmol) was added. The mixture was heated to reflux for 3 hours. The solvent was evaporated under reduced pressure and purified by preparative HPLC to give a compound 81 (20 mg, yield=11%) as a solid.

Example scheme D1

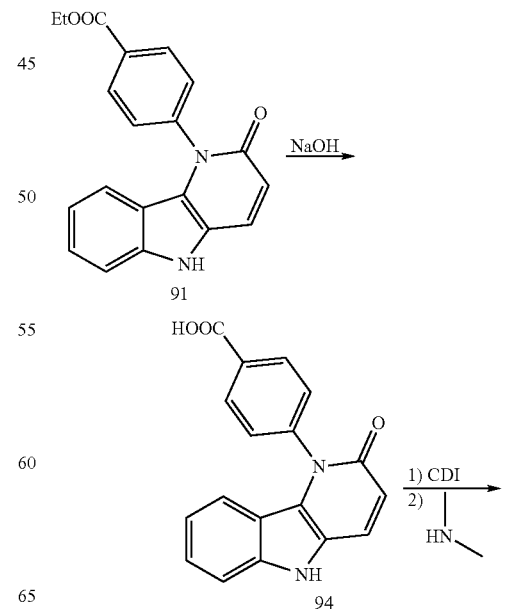

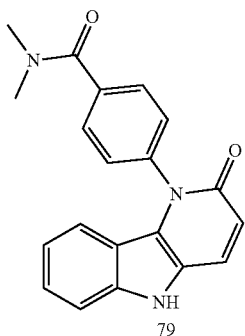

79

To a stirred solution of compound 91 (25 mmol, 83 mg) in DMF (1 ml) was added 2N NaOH (2 ml) and the mixture was heated at 100° C. for 1 hour. The mixture was cooled to room temperature, diluted with water (10 ml) and acidified with concentrated hydrochloric acid to pH=1 causing a white powder to precipitate. The powder was isolated by filtration and successively washed with water, isopropanol and diisopropyl ether to afford 94 (67 mg, yield=88%, purity (LC)>97%)

To a mixture of compound 94 (0.329 mmol, 100 mg) in dry DMF (2 ml), 1,1'-carbonyldiimidazole (1.2 equiv., 0.395 mmol, 64 mg) was added. The reaction mixture was stirred at room temperature for 1 hour. Then a solution of 40% dimethylamine in water (1 ml) was added and the reaction mixture was stirred at room temperature overnight. The reaction mixture was concentrated and the residue was purified by preparative HPLC, affording compound 79 (11 mg, yield=10%, purity (LC)=88%)

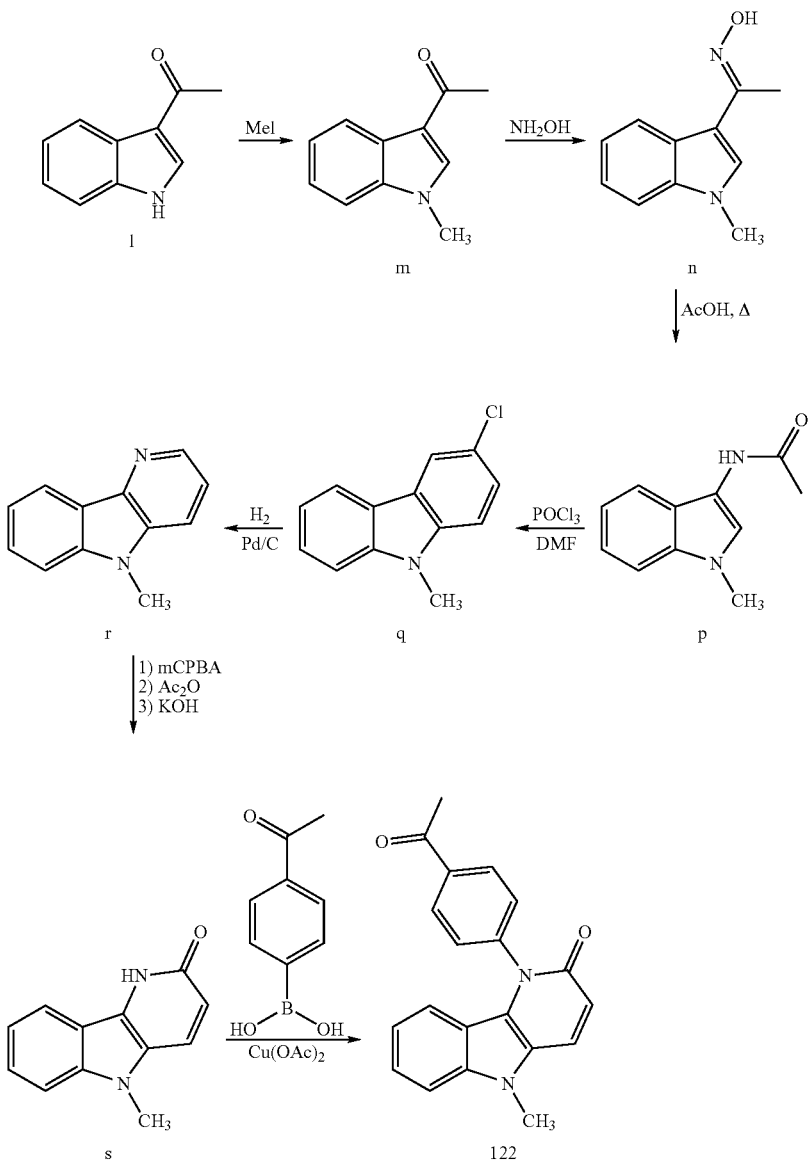

Example scheme E1

To a mixture of 3-acetylindole 1 (0.157 mol, 25.0 g) in DMF (200 ml) was added potassium carbonate (1.05 equiv., 0.165 mol, 22.8 g) and methyl iodide (1.1 equiv., 0.173 mol, 24.5 g). The mixture was stirred at room temperature overnight. To the mixture was added potassium carbonate (2.1 equiv., 0.330 mol, 45.6 g) and methyl iodide (2.2 equiv., 0.346 mol, 49.0 g). The mixture was stirred at room temperature for 3 hours. The mixture was concentrated under reduced pressure to ⅕$^{th}$ of the original volume. The residue was dissolved in dichloromethane and washed with water. The organic phase was dried with MgSO$_4$, concentrated in vacuo, affording intermediate m (purity (LC)=90%). The crude product was used without further purification in the next step.

To a mixture of intermediate m (0.312 mol, 54.0 g) in ethanol (150 ml and water (100 ml) was added acetic acid, sodium salt (2.4 equiv., 0.748 mol, 61.0 g) and hydroxylamine hydrochloride (3 equiv., 0.935 mol, 65.0 g). The mixture was stirred and heated at reflux for 2.5 hours. The mixture was cooled to room temperature. The reaction mixture was poured into water (750 ml). The precipitate was isolated by filtration and washed with water. The crude precipitate was dissolved in THF (200 ml) and toluene (50 ml) and the mixture was evaporated to dryness (2×), affording intermediate n (purity (LC)=80%). The crude product was used as such in the next reaction.

Intermediate n (0.312 mol, 58.7 g) was dissolved in acetic acid (300 ml). The mixture was stirred and heated at reflux for 2 hours. The mixture was concentrated in vacuo. Toluene (100 ml) added and evaporated to dryness (2×). Crystallization from ethanol (400 ml) gave crude intermediate p (31.0 g, purity (LC)=90%). Recrystallization in ethanol (300 ml) afforded p [C. Papamicaël, G. Quéguiner, J. Bourguignon, G. Dupas *Tetrahedron* 2001, 57, 5385-5391] as brown crystals (29.4 g, yield=50%, purity (LC)>98%).

To cooled (0° C.) dry DMF (40 ml) was added dropwise phosphorus oxychloride (2.5 equiv., 0.199 mol, 30.6 g) and the reaction mixture was stirred for 0.5 h at 0° C. Then, a solution of p (0.080 mol, 15.0 g) in DMF (160 ml) was added. The cooling was removed and the reaction mixture was allowed to warm to room temperature overnight. The reaction mixture was poured into ice-water (2 l) and stirred for 0.5 hours. A brown precipitate was isolated by filtration and washed with water. The precipitate was dried for 24 hours in open air, affording intermediate q as a brown powder (6.10 g, yield=35%, purity (LC)=95%).

A mixture of intermediate q (0.005 mol, 1.13 g), Pd/C-catalyst (10%, 0.50 g) and triethylamine (6.8 equiv., 0.036 mol, 3.60 g) in THF (200 ml) was hydrogenated at atmospheric pressure for 2 hours. The catalyst was removed by filtration. The filtrate was evaporated to give r as a brown powder (0.88 g, yield=92%, purity (LC)>95%).

To a mixture of intermediate r (0.005 mol, 0.880 g) and ethanol (5 ml) was added 3-chloroperoxybenzoic acid (70-75%, 1.2 equiv., 0.006 mol, 1.43 g). The reaction mixture was heated at reflux for 2 hours. Pyridine (0.5 equiv., 0.002 mol, 0.190 g) was added and the mixture was heated at reflux for 0.5 h. The reaction mixture was cooled to room temperature and evaporated in vacuo to dryness. The residue was mixed with acetic anhydride (10 ml) and heated at reflux for 4 h and evaporated to dry. The residue was dissolved in 2N potassium hydroxide (50 ml) and stirred for 1 h. The pH of the reaction mixture was adjusted to 1 by the addition of concentrated hydrochloric acid. A brown precipitate was isolated by filtration. The precipitate was washed with a saturated sodium bicarbonate solution (2×10 ml), water, isopropanol and diisopropyl ether, affording intermediate s as a brown powder (0.680 g, yield=71%, purity (LC)>95%).

A mixture of s (0.001 mol, 0.2 g), copper(II) acetate (2 equiv., 0.002 mol, 0.366 g), 4-acetylphenylboronic acid (2 equiv., 0.002 mol, 0.328 g) and powdered molecular sieves (4 Å) in DMF/pyridine (9/1) (3 ml) was heated in a stoppered flask at 80° C. overnight. The molecular sieves were removed by filtration and washed with acetonitrile. The combined filtrates was evaporated under reduced pressure and the crude mixture was purified with by preparative HPLC affording compound 122 (0.066 g, yield=21%, purity (LC)>95%).

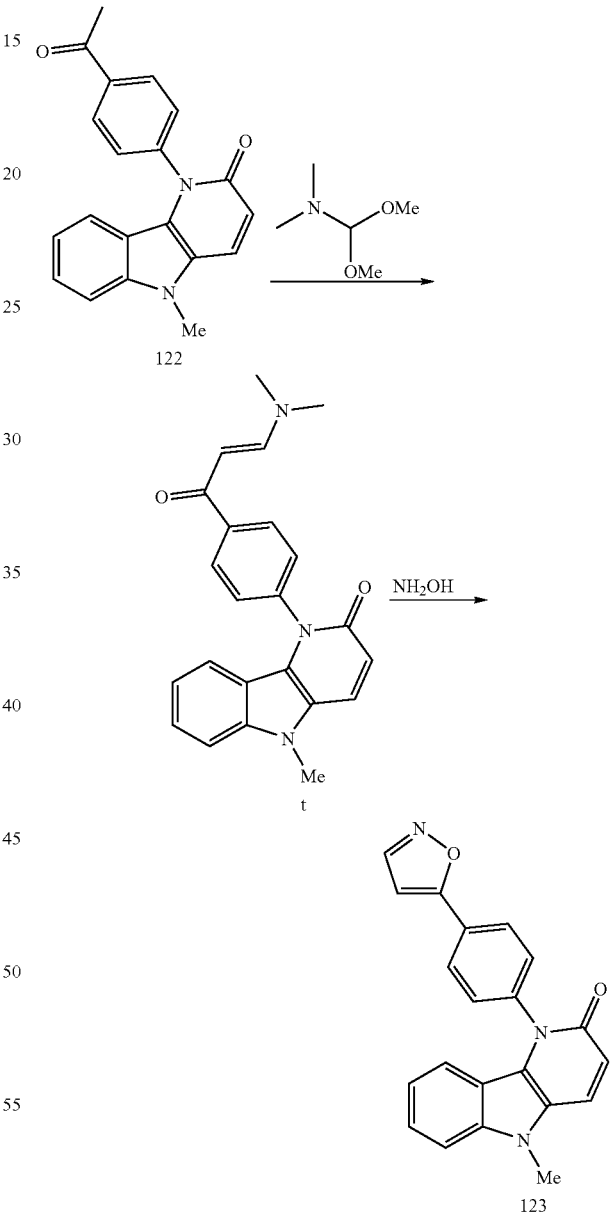

Example scheme E2

To a mixture of compound 122 (0.316 mmol, 0.100 g) in acetonitrile (10 ml) was added N,N-dimethylformamide dimethyl acetal (5 equiv., 1.581 mmol, 0.1883 g) and the mixture was heated at reflux overnight. The solvent was removed under reduced pressure and the crude residue t was used as such the next step.

To a crude mixture of intermediate t in acetic acid (3 ml) was added hydroxylamine hydrochloride (4 equiv., 1.077 mmol, 0.0748 g) and acetic acid sodium salt (3 equiv., 0.8077 mmol, 0.0662 g). The mixture was heated (70° C.) overnight and the solvent was removed under reduced pressure. The product was purified using preparative HPLC affording compound 123 (0.021 g, yield=23%, purity (LC)=91%).

Example scheme F1

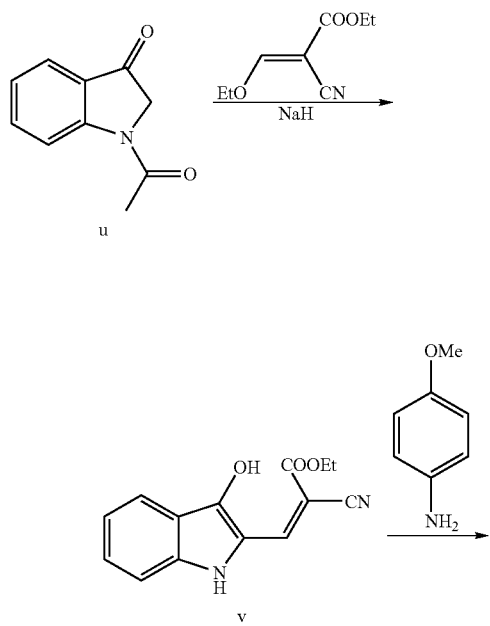

-continued

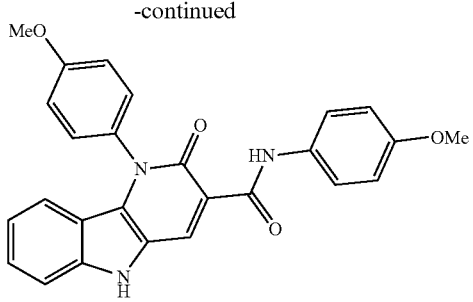

90

To a cooled (–78° C.) stirred suspension of sodium hydride (50% in mineral oil, 2.2 equiv., 44 mmol, 2.11 g) in tetrahydrofuran (30 ml), under a nitrogen atmosphere, was added dropwise, a solution of intermediate u (20 mmol, 3.5 g) in tetrahydrofuran (50 ml) and the reaction was kept at –78° C. for 30 minutes. A solution of ethoxymethylene ethyl cyanoacetate (1.1 equiv., 2.2 mmol, 3.72 g) in tetrahydrofuran (30 ml) was added dropwise at –78° C. over a period of 15 minutes. The reaction was kept at –78° C. for 1 hour. The cooling was removed and the mixture was allowed to warm to room temperature overnight. The reaction mixture was poured into ice-water (400 ml) and acidified with concentrated hydrochloric acid to pH=1. A green precipitate was filtered and dried overnight in open air to afford intermediate v [J. Y. Mérour, S. Piroëlle *J. Heterocyclic Chem.* 1991, 28, 1869-1873] (4.7 g, yield=92%, purity (LC)>95%).

Intermediate v (0.195 mmol, 50 mg) and 4-methoxyaniline (1.5 equiv., 0.293 mmol, 36 mg) were heated at reflux for 1 hour in acetic acid (2 ml) and cooled to room temperature. A yellow precipitate was isolated by filtration and washed with isopropanol and diisopropyl ether to afford compound 90 (28 mg, yield=33%, purity (LC)=97%)

The following tables list examples of compounds of the present invention which compounds have been prepared analogous to one of the foregoing synthesis schemes.

TABLE 2

| Comp. No. | Synthesis scheme | $R^2$ | Salt form |
|---|---|---|---|
| 1 | A1 | H | |
| 2 | A1 | $CH_3$ | |
| 3 | A9 | 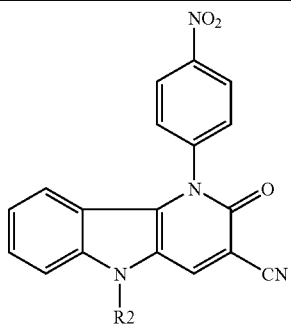 | |

TABLE 2-continued

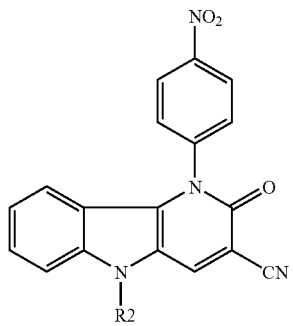

| Comp. No. | Synthesis scheme | R² | Salt form |
|---|---|---|---|
| 4 | A7 | (1-methylbutyl) CH(CH₃)CH₂CH₂CH₃ | |
| 5 | A7 | (2-methylbutyl) CH₂CH(CH₃)CH₂CH₃ | |
| 6 | A7 | benzyl | |
| 7 | A7 | CH₂CH=CHCH₃ (but-2-enyl) | |
| 8 | A7 | 1-butyl | |
| 9 | A7 | ethyl | |
| 10 | A7 | cyclopentyl | |
| 11 | A7 | 3-morpholinopropyl | |
| 12 | A7 | pent-4-enyl (CH₂CH₂CH₂CH=CH₂) | |
| 13 | A7 | 3-(pyrrolidin-1-yl)propyl | |
| 14 | A7 | 3-(pyrrolidin-1-yl)propyl | chlorohydrate |
| 15 | A7 | 3-(pyrrolidin-1-yl)propyl | oxalate |
| 16 | A7 | 3-(pyrrolidin-1-yl)propyl | methanesulfonate |
| 17 | A7 | 3-(piperidin-1-yl)propyl | |
| 18 | A7 | 4-(dimethylamino)butyl | |
| 19 | A9 | CH₂CH₂C(=O)OH | |

TABLE 2-continued

[Structure: tricyclic core with N-(4-nitrophenyl), C=O, CN substituents, and N-R2]

| Comp. No. | Synthesis scheme | R² | Salt form |
|---|---|---|---|
| 20 | A9 | -CH₂CH₂-C(=O)-N(piperazine)N-CH₃ | |
| 21 | A8 | -(CH₂)₄-N(piperidine) | |
| 22 | A8 | -(CH₂)₅-N(piperazine)N-CH₃ | |
| 23 | A8 | -(CH₂)₅-N(morpholine) | |
| 24 | A8 | -(CH₂)₄-N(pyrrolidine) | |
| 25 | A8 | -(CH₂)₅-N(pyrrolidine) | |
| 26 | A8 | -(CH₂)₄-N(piperazine)N-CH₃ | |
| 27 | A7 | -CH₂CH₂-CN | |
| 28 | A8 | -(CH₂)₄-N(morpholine) | |
| 29 | A8 | -(CH₂)₅-N(piperidine) | |
| 30 | A9 | -CH₂CH₂-C(=O)-O-CH₂CH₃ | |
| 31 | A7 | -(CH₂)₃-CN | |
| 32 | A8 | -(CH₂)₅-N(CH₃)₂ | |

TABLE 2-continued
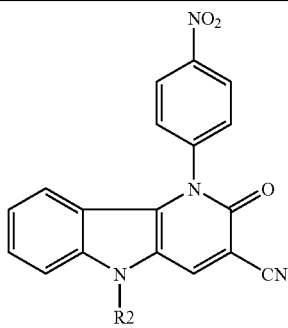
| Comp. No. | Synthesis scheme | R² | Salt form |
|---|---|---|---|
| 33 | A7 | 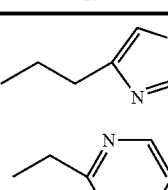 | |
| 34 | A7 | 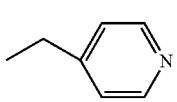 | |
| 35 | A7 | 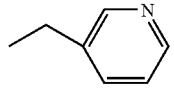 | |
| 36 | A7 | 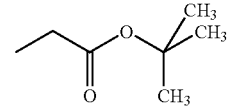 | |
| 125 | A9 | 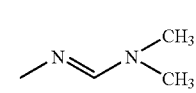 | |
TABLE 3
| Comp. No. | Synthesis scheme | R² | R$_{3a}$ | R$_{3b}$ |
|---|---|---|---|---|
| 37 | B1 | H | F | H |
| 38 | B1 | H | Br | H |
| 39 | B1 | CH$_3$ | Br | H |
| 40 | A2 | CH$_3$ | N=CH-N(CH$_3$)CH$_3$ | H |
| 41 | A1 | H | F | NO$_2$ |
| 42 | A1 | H | H | NO$_2$ |
| 43 | A1 | CH$_3$ | H | NO$_2$ |
| 44 | B1 | CH$_3$ | F | H |

TABLE 3-continued
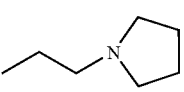
| Comp. No. | Synthesis scheme | R² | R₃ₐ | R₃ᵦ |
|---|---|---|---|---|
| 45 | A1 | H | CN | H |
| 46 | A1 | CH₃ | CN | H |
| 47 | A7 | 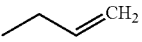 | CN | H |
| 48 | B2 | CH₃ | 2-furanyl | H |
| 49 | A7 | 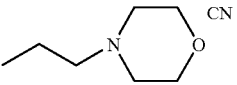 | CN | H |
| 50 | A7 | 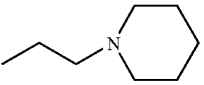 | CN | H |
| 51 | A7 | 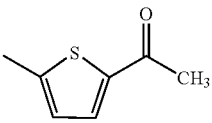 | CN | H |
| 52 | B2 | CH₃ | 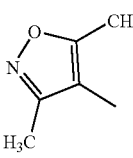 | H |
| 53 | B2 | CH₃ | 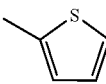 | H |
| 54 | A2 | H | NH₂ | H |
| 55 | B2 | CH₃ | 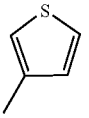 | H |
| 56 | B1 | CH₃ | —O—CH₃ | H |
| 57 | B2 | CH₃ | 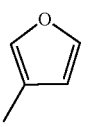 | H |
| 58 | B2 | CH₃ |  | H |

TABLE 3-continued

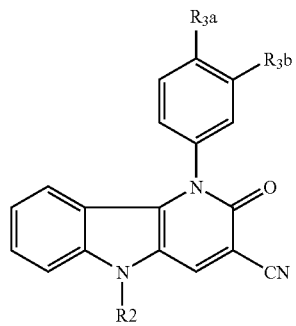

| Comp. No. | Synthesis scheme | R² | R₃ₐ | R₃ᵦ |
|---|---|---|---|---|
| 59 | A5 | CH₃ | pyrrol-1-yl | H |
| 60 | E1 | CH₃ | OH | H |
| 61 | A6 | CH₃ | 1,2,4-triazol-4-yl | H |

TABLE 4

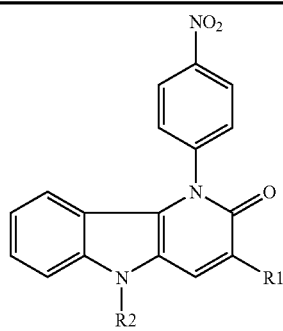

| Comp. No. | Synthesis scheme | R₁ | R₂ |
|---|---|---|---|
| 62 | A10 | 3,5-dimethyl-1,2,4-oxadiazol-? | CH₃ |
| 63 | A11 | 3-methyl-1,2,4-oxadiazol-5(4H)-one | CH₃ |
| 64 | A15 | pyridin-3-yl | H |
| 65 | A13 | C(O)OCH₂CH₃ | H |
| 66 | C1 | H | H |
| 67 | C1 | H | CH₃ |
| 68 | C9 | Br | CH₃ |

TABLE 4-continued

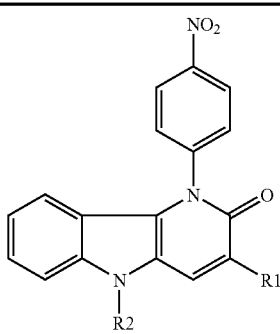

| Comp. No. | Synthesis scheme | R₁ | R₂ |
|---|---|---|---|
| 69 | A14 | tetrazol-5-yl | H |
| 70 | A10 | C(NH₂)=N-OH | CH₃ |
| 71 | A10 | 3-methyl-5-tert-butyl-1,2,4-oxadiazol-yl | CH₃ |
| 72 | A10 | 3-methyl-5-CF₃-1,2,4-oxadiazol-yl | CH₃ |

TABLE 4-continued

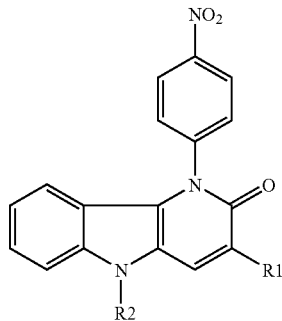

| Comp. No. | Synthesis scheme | R₁ | R₂ |
|---|---|---|---|
| 73 | A12 | (3-methyl-1,2,4-oxadiazole-5-thione) | CH₃ |
| 74 | A13 | (methyl acetate group) | H |
| 75 | A13 | (methyl acetate group) | CH₃ |

TABLE 4-continued

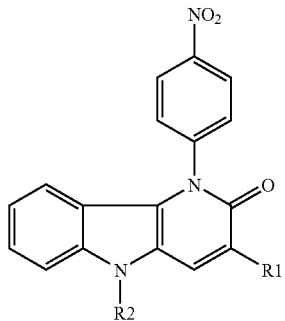

| Comp. No. | Synthesis scheme | R₁ | R₂ |
|---|---|---|---|
| 76 | A13 | (acetamide group) | CH₃ |
| 77 | A13 | (acetic acid group) | H |
| 78 | C9 | (4-methylpyridine) | CH₃ |

TABLE 5

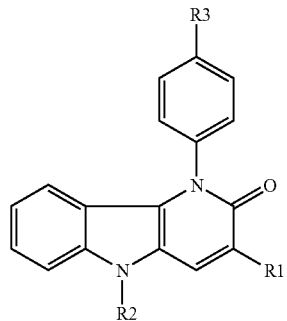

| Comp. No | Synthesis scheme | R¹ | R² | R³ |
|---|---|---|---|---|
| 79 | D1 | H | H | (N,N-dimethylacetamide group) |
| 80 | C2 | H | CH₃ | (3-methyl-5-benzyl-1,2,4-oxadiazole) |
| 81 | C12 | H | CH₃ | (2-methylthiazole-4-carboxylic acid) |

TABLE 5-continued
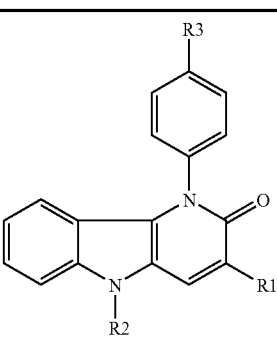
| Comp. No | Synthesis scheme | R¹ | R² | R³ |
|---|---|---|---|---|
| 82 | C5 | H | CH₃ | 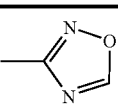 |
| 83 | C3 | H | CH₃ | 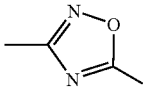 |
| 84 | C4 | H | CH₃ | 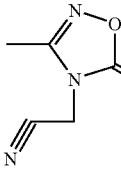 |
| 85 | C2 | H | CH₃ | 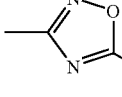 |
| 86 | C9 | Br | CH₃ | 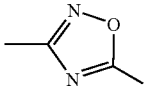 |
| 87 | C11 | Cl | CH₃ | —COOH |
| 88 | C9 | 2-furanyl | CH₃ | —CN |
| 89 | A4 | CN | CH₃ | —NH₂ |
| 90 | F1 | 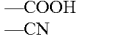 | H | —OCH₃ |
| 91 | C1 | H | H | 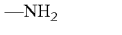 |
| 92 | C1 | H | CH₃ | 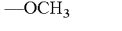 |
| 93 | C1 | H | H | —CN |
| 94 | D1 | H | H | —COOH |
| 95 | C8 | H | H | 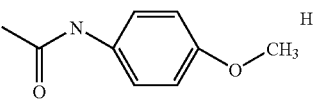 |

TABLE 5-continued
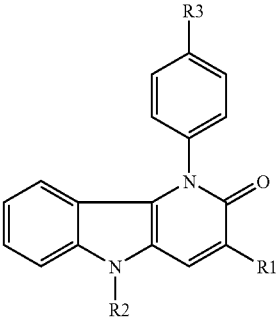
| Comp. No | Synthesis scheme | R¹ | R² | R³ |
|---|---|---|---|---|
| 96 | C1 | H | CH₃ | —CN |
| 97 | C2 | H | CH₃ | 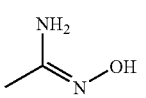 |
| 98 | C10 | H | CH₃ | 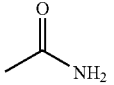 |
| 99 | C11 | H | CH₃ | —COOH |
| 100 | C2 | H | CH₃ | 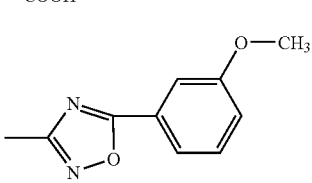 |
| 101 | C2 | H | CH₃ | 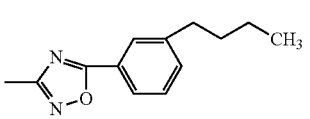 |
| 102 | C2 | H | CH₃ | 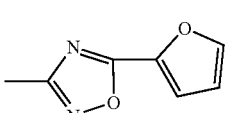 |
| 103 | C2 | H | CH₃ | 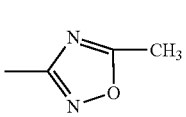 |
| 104 | C12 | H | CH₃ | 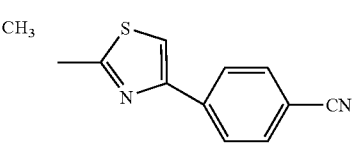 |
| 105 | C12 | H | CH₃ | 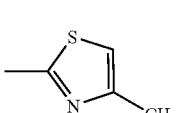 |
| 106 | C2 | H | CH₃ | 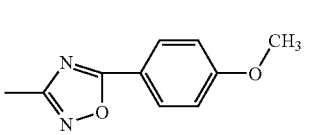 |

TABLE 5-continued
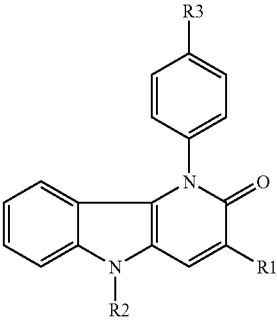
| Comp. No | Synthesis scheme | R¹ | R² | R³ |
|---|---|---|---|---|
| 107 | C2 | H | CH₃ | 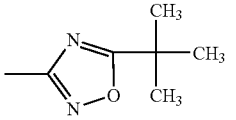 |
| 108 | C2 | H | CH₃ | 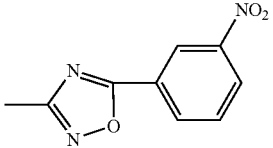 |
| 109 | C2 | H | CH₃ | 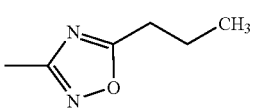 |
| 110 | C2 | H | CH₃ | 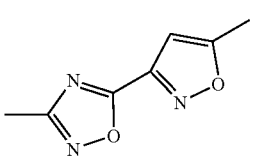 |
| 111 | C2 | H | CH₃ | 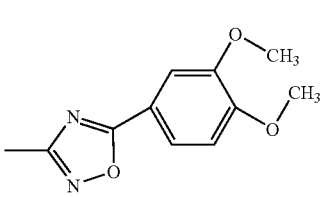 |
| 112 | C2 | H | CH₃ | 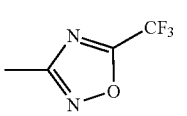 |
| 113 | A10 + C2 | 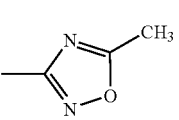 | H | 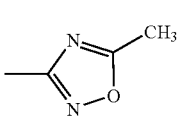 |
| 114 | C2 | H | CH₃ | 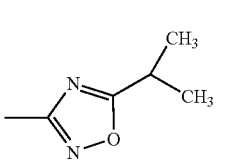 |

TABLE 5-continued
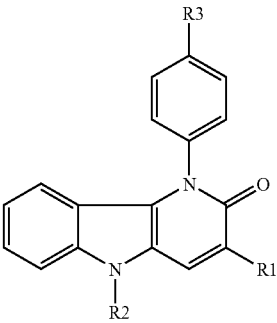
| Comp. No | Synthesis scheme | R¹ | R² | R³ |
|---|---|---|---|---|
| 115 | C2 | H | CH₃ | 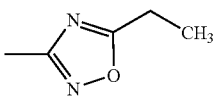 |
| 116 | A10 + C2 | 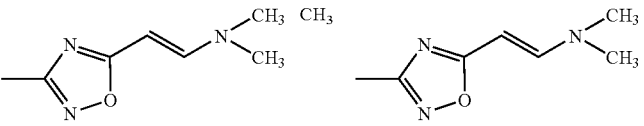 | CH₃ | 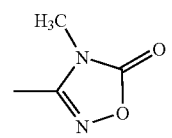 |
| 117 | C4 | H | CH₃ | 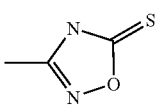 |
| 118 | C7 | H | CH₃ | 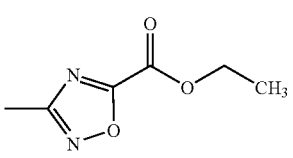 |
| 119 | C6 | H | CH₃ | 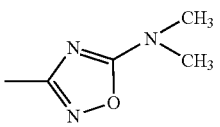 |
| 120 | C3 | H | CH₃ |  |
| 121 | E1 | H | CH₃ | —I |
| 122 | E1 | H | CH₃ | 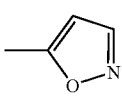 |
| 123 | E2 | H | CH₃ | 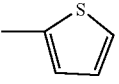 |
| 124 | C9 | (thiophene) | CH₃ | —CN |

TABLE 5-continued

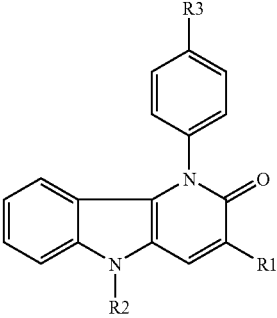

| Comp. No | Synthesis scheme | R¹ | R² | R³ |
|---|---|---|---|---|
| 126 | C3 | H | $CH_3$ | 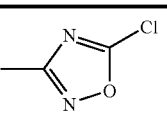 |
| 127 | C9 | Br | $CH_3$ | CN |
| 128 | C12 | H | $CH_3$ | 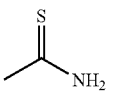 |

Time of Addition Experiment

A time of addition experiment was performed to determine the mechanism of action of the compounds of the present invention. In the time of addition experiment, compounds are added to cells that were infected with HIV, at time zero (Zero hours). The compounds are subsequently added at different points in time. The time point until which a compound can be added to prevent virus replication, provides an indication of the mechanism of action of the compound.

In the present experiment, MT4 cells were infected with HIV-1 strain LAI at time zero. In different experiments, compounds were subsequently added at the points in time indicated in the X-axis of FIG. 1 (in hours). The compounds were added at the following end concentrations during incubation: DS5000, 1 µM; efavirenz (EFV), 1 µM; saquinavir (SQV), 1 µM; Reference 1, 10 µM (Reference 1 is an integrase inhibitor selected from WO 99/62520 and is present in CAS database: 251963-93-6); Compound 2, 50 µM; Control: normalized virus production. The virus production was determined using p24 monitoring using a kit according to the manufacturers instructions (p24 ELISA kit, catalog reference NEK-050, Perkin Elmer).

Compound 2 delayed virus production using a mechanism related to reverse transcriptase.

In vitro Inhibition of HIV Reverse Transcriptase

The assay was run using kit TRK 1022 (Amersham Life Sciences) according to the manufacturer's instructions with slight modifications. Compounds were diluted in steps of ¼ in 100% DMSO and subsequently transferred to Medium A (1/50 dilution; medium A: RPMI 1640+10% FetalClone II+Gentamycin 20 mg/L). 25 µl of compound (in 2% DMSO in Medium A) or 25 µl of 2% DMSO in medium A was added to wells. To each well was added 25.5 µl master mix (master mix: 5 µl primer/template beads, 10 µl assay buffer, 0.5 µl tracer (3H-TTP), 5 µl HIV RT enzyme solution at a final enzyme activity of 15 mU per 50 µl reaction, 5 µl medium A). The plates were sealed, marked as radioactive and incubated during 4 hours at 37° C. Subsequently, 100 µl stop solution was added to each well (except R1). The radioactivity was counted in a TopCount.

Compound 2 inhibits HIV reverse transcriptase in vitro and consequently does not need conversion to an active metabolite in order to inhibit reverse transcriptase.

Metabolization of the Compounds of the Present Invention

The present experiment provides insight into the hepatic first pass metabolization of compounds.

Aliquots of human liver microsomal fractions (prepared by centrifugation at 12000 $g^{-1}$) were transferred into 10 ml glass tubes that are immersed in ice. Subsequently, test compound was added to yield a final concentration of 10 µM test compound. After adding 500 µl of a co-factor solution (cofactor solution: 1 mg/ml glucose-6-phosphate, 1 mg/ml $MgCl_2.6H_2O$, 0.5 units/ml glucose-6-phosphate dehydrogenase in 0.5 M phohsphate buffer. pH 7.4), homogenisation buffer (homogenisation buffer: 1,15% KCl in 0.05 M phosphate buffer, pH 7.4) was added to give a final volume of 1 ml. The incubations, 30 or 120 minutes at 37° C., were initiated by adding 10 µl of a solution of nicontinamide adenine dinucleotide phosphate (1.25 mg/ml) in homogenisation buffer. After a preincubation during 5 minutes at 37° C., the tubes were continuously shaken at 100 oscillations/minute in a water bath. The reactions were terminated by addition of an equal volume of DMSO. Blank incubations containing boiled microsomal fractions were incubated under the same conditions as the drug incubations. The degree of metabolism was determined by direct measurement of the residual parent compound in the reaction mixture using LC-MS. In parallel, the residual anti-HIV activity in the reaction mixture was detected using a colorimetric anti-HIV assay as described in Pauwels et al. J. Virol. Methods 1988 (20) 309-321. The residual activity is defined as the percent difference in $EC_{50}$ between the drug incubations and the blank incubations.

The results in Table 6 indicate that compound 2 underwent little or no hepatic first pass metabolism. Te same result was obtained for other compounds like compound numbers 11, 13 and 17.

Table 6. Microsomal Metabolization.

The amount of compound was determined using LC-MS at the time points indicated between brackets. The results are indicated as a % vis-à-vis the amount determined at the start of the experiment (time=0; normalized to 100%).

| Compound name Concentration | Compound 2 10 µM |
|---|---|
| DLM (0 min) (in %) | 100 |
| DLM (30 min) (in %) | 91 |
| DLM (120 min) (in %) | 108 |
| HLM (0 min) (in %) | 100 |
| HLM (30 min) (in %) | 98 |
| HLM (120 min) (in %) | 128 |

DLM: dog liver microsomes,
HLM: human liver microsomes,
min: minutes.

Antiviral Analyses:

The compounds of the present invention were examined for anti-viral activity in a cellular assay. The assay demonstrated that these compounds exhibit potent anti-HIV activity against a wild type laboratory HIV strain (HIV-1 strain LAI). The cellular assay was performed according to the following procedure.

HIV- or mock-infected MT4 cells were incubated for five days in the presence of various concentrations of the inhibitor. At the end of the incubation period, the replicating virus in the control cultures has killed all HIV-infected cells in the absence of any inhibitor. Cell viability was determined by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution was monitored at 540 nm. The values correlate directly to the number of living cells remaining in the culture at the completion of the five day incubation. The inhibitory activity of the compound was monitored on the virus-infected cells and was expressed as $EC_{50}$ and $EC_{90}$. These values represent the amount of the compound required to protect 50% and 90%, respectively, of the cells from the cytopathogenic effect of the virus. The toxicity of the compound was measured on the mock-infected cells and was expressed as $CC_{50}$, which represents the concentration of compound required to inhibit the growth of the cells by 50%. The selectivity index (SI) (ratio $CC_{50}/EC_{50}$) is an indication of the selectivity of the anti-HIV activity of the inhibitor. Wherever results are reported as e.g. $pEC_{50}$ or $pCC_{50}$ values, the result is expressed as the negative logarithm of the result expressed as $EC_{50}$ or $CC_{50}$ respectively.

Because of the increasing emergence of drug resistant HIV strains, the present compounds were also tested for their potency against clinically isolated HIV strains harbouring several mutations (Tables 1 and 7). These mutations are associated with resistance to reverse transcriptase inhibitors and result in viruses that show various degrees of phenotypic cross-resistance to the currently commercially available drugs such as for instance AZT, didanosine, nevirapine, lamivudine and zalcibatine.

Results:

As a measure of the broad spectrum activity of the present compounds, the $EC_{50}$ was determined. Table 7 shows the results of the antiviral testing of the respective compounds expressed in $pEC_{50}$. The fold resistance rounded to the nearest integer is mentioned between brackets.

As can be seen in this table, the present compounds are effective in inhibiting a broad range of mutant strains: Row A: $pEC_{50}$ value towards mutant A, Row B: $pEC_{50}$ towards mutant B, Row C: $pEC_{50}$ towards mutant C, Row D: $pEC_{50}$ towards mutant D, Row E: $pEC_{50}$ towards mutant E, Row F: $pEC_{50}$ towards mutant F, Row G: $pEC_{50}$ towards mutant G, Row H: $pEC_{50}$ towards mutant G, Row H: $pEC_{50}$ towards mutant H, Row I: $pEC_{50}$ towards mutant I, Row J: $pEC_{50}$ towards mutant J, Row K: $pEC_{50}$ towards mutant K, Row HIV-2: $pEC_{50}$ towards mutant HIV-2, Row SIV (simian immunodeficiency virus): $pEC_{50}$ towards mutant SIV. Row WT: pEC50 against wild type HIV-LAI strain. The toxicity (Tox) is expressed as the $pCC_{50}$ value as determined with mock transfected cells. ND means not determined.

TABLE 7

Results of the toxicity testing and the resistance testing.

| Strain | Compound 1 | Compound 2 |
|---|---|---|
| WT | 6.5 | 7.6 |
| A | 5.6 (8) | 7.0 (4) |
| B | 5.9 (4) | 7.5 (1) |
| C | 5.6 (8) | 7.1 (3) |
| D | 6.0 (3) | 7.3 (2) |
| E | 5.7 (6) | 7.2 (3) |
| F | 5.9 (4) | 7.4 (2) |
| G | 6.2 (2) | 7.2 (3) |
| H | 5.8 (5) | 6.9 (5) |
| I | 6.1 (3) | 7.2 (3) |
| J | 5.8 (5) | 6.9 (5) |
| K | 6.5 (1) | 7.0 (4) |
| HIV-2 | 5.2 | 6.6 |
| SIV | 5.1 | 6.5 |
| Tox | <4.49 | <4.49 |

For comparative purposes, 2-(dimethylamino)-4,5-dihydro-5-methyl-1-(4-nitrophenyl)-4-(2-oxopropyl)-1H-pyrido[3,2-b]indole-3-carbonitrile as mentioned in WO 02/055520 has a $pEC_{50}$ for wild type HIV virus of 5.5 indicating an increase in potency for the compounds of the present invention ranging between about 1 and 2 log units.

The other compounds exemplified in the present application have also been tested for their antiviral activity. With respect to their ability to inhibit the wild-type HIV-LAI strain, the compound numbers 5, 7, 8, 9, 11, 12, 13, 14, 15, 16, 17, 18, 21, 23, 25, 26, 27, 28, 29, 32, 35, 43, 67, 68, 71 and 72 had an $EC_{50}$ value of lower than 1 µM. The compound numbers 3, 6, 10, 19, 20, 22, 24, 30, 31, 33, 34, 36, 38, 39, 40, 41, 42, 46, 47, 48, 49, 51, 52, 53, 56, 62, 66, 69, 70, 73, 76, 81, 82, 84, 85, 86, 87, 93, 94, 96, 97, 98, 99, 102, 103, 106, 109, 110, 111, 114, 115 and 117 had an $EC_{50}$ value between 1 µM and 32 µM. The compound numbers 37, 44, 45, 50, 57, 58, 63, 79, 80, 83, 89, 90, 91, 92, 95, 100, 101, 104, 105, 108, 112, 113, 118, 119 and 120 had an $EC_{50}$ value of higher than 32 µM.

Oral Availability in the Rat and the Dog

Compounds of formula (I) were formulated as a 20 mg/ml solution or suspension in DMSO, PEG400 or cyclodextin 40% (CD40%) in water. For most experiments in the rat, three dosing groups were formed: 1/ single intraperitoneal dose at 20 mg/kg using the DMSO formulation; 2/ single oral dose at 20 mg/kg using the PEG400 formulation and 3/ single oral dose at 20 mg/kg using the cyclodextrin formulation. Blood was sampled at regular time intervals after dosing and drug concentrations in the serum were determined using a LC-MS bioanalytical method.

Formulation

Active ingredient, in casu a compound of formula (I), can be dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropyl-methylcellulose (HPMC), typically 5 mPa·s, can be dissolved in organic solvents such as ethanol, methanol methylene chloride. Suitably the polymer can be dissolved in ethanol. The polymer and compound solutions can be mixed and subsequently spray dried. The ratio of compound/polymer can be selected from 1/1 to 1/6. Intermediate ranges can be 1/1.5 and 1/3. A suitable ratio can be 1/6. The spray-dried powder, a solid dispersion, can subsequently be filled in capsules for administration. The drug load in one capsule can range between 50 and 100 mg depending on the capsule size used.

Film-coated Tablets

Preparation of Tablet Core

A mixture of 100 g of active ingredient, in casu a compound of formula (I), 570 g lactose and 200 g starch can be mixed well and thereafter humidified with a solution of 5 g sodium dodecyl sulfate and 10 g polyvinylpyrrolidone in about 200 ml of water. The wet powder mixture can be sieved, dried and sieved again. Then there can be added 100 g microcrystalline cellulose and 15 g hydrogenated vegetable oil. The whole can be mixed well and compressed into tablets, giving 10.000 tablets, each comprising 10 mg of the active ingredient.

Coating

To a solution of 10 g methylcellulose in 75 ml of denaturated ethanol there can be added a solution of 5 g of ethylcellulose in 150 ml of dichloromethane. Then there can be added 75 ml of dichloromethane and 2.5 ml 1,2,3-propanetriol. 10 g of polyethylene glycol can be molten and dissolved in 75 ml of dichloromethane. The latter solution can be added to the former and then there can be added 2.5 g of magnesium octadecanoate, 5 g of polyvinylpyrrolidone and 30 ml of concentrated color suspension and the whole can be homogenated. The tablet cores can be coated with the thus obtained mixture in a coating apparatus.

The invention claimed is:

1. A compound of formula (I)

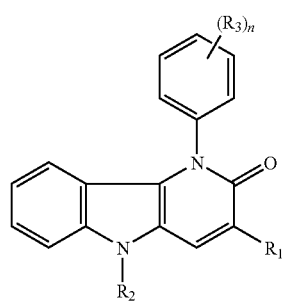

(I)

or a pharmaceutically acceptable salt, or stereoisomeric form, wherein n is 1, 2 or 3;

$R_1$ is hydrogen, cyano, halo, aminocarbonyl, hydroxycarbonyl, $C_{1-4}$alkyloxycarbonyl, $C_{1-4}$alkylcarbonyl, mono- or di($C_{1-4}$alkyl)aminocarbonyl, arylaminocarbonyl, N-(aryl)-N—($C_{1-4}$alkyl)aminooarbonyl, methanimidamidyl, N-hydroxy-methanimidamidyl, or mono- or di($C_{1-4}$alkyl)methanimidamidyl, or $Het_1$;

$R_2$ is hydrogen, $C_{1-10}$alkyl, $C_{2-10}$alkenyl, $C_{3-7}$cycloalkyl, wherein said $C_{1-10}$alkyl, $C_{2-10}$alkenyl and $C_{3-7}$cycloalkyl, each individually and independently, may be optionally substituted with a substituent selected from the group consisting of cyano, $NR_{4a}R_{4b}$, pyrrolidinyl, piperidinyl, homopiperidinyl, piperazinyl, 4-($C_{1-4}$alkyl))-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $N(R_{4a}R_{4b})$carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-ylcarbonyl, thiomorpholin-1-ylcarbonyl, 1-oxothiomorpholin-1-ylcarbonyl and 1,1-dioxo-thiomorpholin-1-ylcarbonyl;

$R_3$ is nitro, cyano, amino, halo, hydroxy, $C_{1-4}$alkyloxy, hydroxycarbonyl, aminocarbonyl, $C_{1-4}$alkyloxycarbonyl, mono- or di($C_{1-4}$alkyl)aminocarbonyl, $C_{1-4}$alkylcarbonyl, methanimidamidyl, mono- or di($C_{1-4}$alkyl)methanimidamidyl, N-hydroxy-methanimidamidyl or $Het_1$;

$R_{4a}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

$R_{4b}$ is hydrogen, $C_{1-4}$alkyl or $C_{1-4}$alkyl substituted with a substituent selected from the group consisting of amino, mono- or di($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

aryl is phenyl optionally substituted with one or more substituents each individually selected from the group consisting of $C_{1-6}$alkyl, $C_{1-4}$alkoxy, halo, hydroxy, amino, trifluoromethyl, cyano, nitro, hydroxy$C_{1-6}$alkyl, cyano$C_{1-6}$alkyl, mono- or di($C_{1-4}$alkyl)amino, amino$C_{1-4}$alkyl, mono- or di($C_{1-4}$alkyl)amino$C_{1-4}$alkyl;

$Het_1$ is a 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl mono- or di($C_{1-4}$alkyl)amino$C_{1-4}$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadlazolyl, thiadiazolyl and triazolyl moieties may optionally be substituted with $C_{1-4}$alkyl provided that the compound of formula (1) is different from 2,5-dihydro-1-(4-nitrophenyl)-2-oxo-1H-pyrido[3,2-b]indole-3-carbonitrile, and 2,5-dihydro-5-methyl-1-(4-nitrophenyl)-2-oxo-1H-pyrido[3,2-b]indole-3-carbonitrile.

2. A compound according to claim 1 wherein n is 1, $R_3$ is nitro, $R_1$ is cyano, $C_{1-4}$alkyloxyoarbonyl or $C_{1-4}$alkylaminocarbonyl; and $R_2$ is hydrogen or $C_{1-6}$alkyl.

3. A compound according to claim 1 wherein
n is 1 or 2:
$R_3$ is nitro, cyano, amino, halo, hydroxy, $C_{1-4}$alkyloxy, hydroxycarbonyl, aminocarbonyl, aminothiocarbonyl, $C_{1-4}$alkyloxycarbonyl, $C_{1-4}$alkylcarbonyl, mono- or di($C_{1-4}$alkyl)methanimidamidyl, N-hydroxy-methanimidamidyl or $Het_1$.

4. A compound according to claim 1 wherein
$R_1$ is hydrogen, cyano, halo, aminocarbonyl, hydroxycarbonyl, $C_{1-4}$alkyloxycarbonyl, arylaminocarbonyl, N-hydroxy-methanimidamidyl, mono- or di($C_{1-4}$alkyl)methanimidamidyl, or $Het_1$; and
aryl is phenyl optionally substituted with one or more substituents each individually selected from the group consisting of $C_{1-6}$alkyl, $C_{1-4}$alkoxy, cyano, nitro; and
$Het_1$ is a 5-membered ring system wherein one, two, three or four ring members are heteroatoms each individually and independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{3-7}$cycloalkyl, halo, cyano, trifluoromethyl, cyano$C_{1-4}$alkyl, mono- or di($C_{1-4}$alkyl)amino, mono- or di($C_{1-4}$alkyl)amino$C_{2-6}$alkenyl, isoxazolyl, aryl, hydroxycarbonyl, $C_{1-4}$alkyloxycarbonyl, oxo, thio; and wherein the foregoing isoxazolyl may optionally be substituted with $C_{1-4}$alkyl.

5. A compound according to claim 1 wherein
$R_2$ is hydrogen, $C_{1-10}$alkyl, $C_{2-10}$alkenyl, $C_{3-7}$cycloalkyl or $C_{1-10}$alkyl substituted with substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl or 4-($C_{1-4}$alkyl)-piperazin-1-ylcarbonyl; and
$R_{4a}$ is $C_{1-4}$alkyl; and
$R_{4b}$ is $C_{1-4}$alkyl or $C_{1-4}$alkyl substituted morpholinyl.

6. A compound according to claim 1 wherein
$R_2$ is hydrogen, $C_{1-10}$alkyl, $C_{2-10}$alkenyl, $C_{3-7}$cycloalkyl or $C_{1-10}$alkyl substituted with substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl or 4-($C_{1-4}$alkyl)-piperazin-1-ylcarbonyl; and
aryl is phenyl optionally substituted with one or more substituents each individually selected from the group consisting of $C_{1-6}$alkyl, $C_{1-4}$alkoxy, cyano, and nitro.

7. A compound according to claim 1 wherein
$R_2$ is hydrogen, $C_{1-10}$alkyl, $C_{2-10}$alkenyl, $C_{3-7}$cycloalkyl or $C_{1-10}$alkyl substituted with substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl or 4-($C_{1-4}$alkyl)-piperazin-1-ylcarbonyl; and
aryl is phenyl optionally substituted with one or more substituents each individually selected from the group consisting of $C_{1-6}$alkyl, $C_{1-4}$alkoxy, cyano, and nitro; and $R_{4a}$ is $C_{1-4}$alkyl; and
$R_{4b}$ is $C_{1-4}$alkyl or $C_{1-4}$alkyl substituted morpholinyl.

8. A compound according to claim 1 wherein
$R_3$ is nitro, cyano, amino, halo, hydroxy, $C_{1-4}$alkyloxy, hydroxycarbonyl, aminocarbonyl, aminothiocarbonyl, $C_{1-4}$alkyloxycarbonyl, $C_{1-4}$alkylcarbonyl, mono- or di($C_{1-4}$alkyl)methanimidamidyl, N-hydroxy-methanimidamidyl or $Het_1$; and
$Het_1$ is a 5-membered ring system wherein one, two, three or four ring members are heteroatoms each individually and independently selected from the group consisting of nitrogen, oxygen and sulfur, and wherein the remaining ring members are carbon atoms;
and, where possible, any nitrogen ring member may optionally be substituted with $C_{1-4}$alkyl;
any ring carbon atom may, each individually and independently, optionally be substituted with a substituent selected from the group consisting of $C_{1-4}$alkyl, $C_{3-7}$cycloalkyl, halo, cyano, trifluoromethyl, cyano$C_{1-4}$alkyl, mono- or di($C_{1-4}$alkyl)amino, mono- or di($C_{1-4}$alkyl)amino$C_{2-6}$alkenyl, isoxazolyl, aryl, hydroxycarbonyl, $C_{1-4}$alkyloxycarbonyl, oxo, thio; and wherein the foregoing isoxazolyl may optionally be substituted with $C_{1-4}$alkyl.

9. A compound according to claim 1 wherein
n is 1; and
$R_1$ is hydrogen, cyano, halo, aminocarbonyl, hydroxycarbonyl, $C_{1-4}$alkyloxycarbonyl, arylaminocarbonyl, N-hydroxy-methanimidamidyl, mono- or di($C_{1-4}$alkyl)methanimidamidyl or, $Het_1$; and
$R_2$ is hydrogen, $C_{1-10}$alkyl, $C_{2-10}$alkenyl, $C_{3-7}$cycloalkyl or $C_{1-10}$alkyl substituted with substituent selected from the group consisting of cyano, $NR_{4a}R_{4b}$, pyrrolidinyl, piperidinyl, 4-($C_{1-4}$alkyl)-piperazinyl, morpholinyl, aryl, imidazolyl, pyridyl, hydroxycarbonyl, $N(R_{4a}R_{4b})$carbonyl, $C_{1-4}$alkyloxycarbonyl or 4-($C_{1-4}$alkyl)-piperazin-1-ylcarbonyl; and
$R_3$ is nitro, cyano, amino, halo, hydroxy, $C_{1-4}$alkyloxy, hydroxycarbonyl, aminocarbonyl, aminothiocarbonyl, $C_{1-4}$alkyloxycarbonyl, $C_{1-4}$alkylcarbonyl, mono- or di($C_{1-4}$alkyl)methanimidamidyl, N-hydroxy-methanimidamidyl or $Het_1$.

10. A compound according to claim 1 wherein the compound has the formula (II)

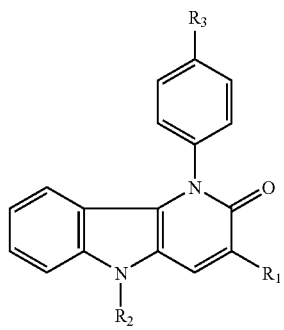

(II)

11. A compound according to claim 1 wherein $R_3$ is nitro.
12. A compound according to claim 1 wherein $R_1$ is cyano.
13. A compound according to claim 1 wherein $R_1$ is $C_{1-4}$alkyloxycarbonyl or $C_{1-4}$alkylaminocarbonyl.
14. A compound according to claim 1 wherein $R_2$ is $C_{2-6}$alkyl.
15. A compound according to claim 1 wherein
n is 1,
$R_1$ is cyano, halo or oxadiazolyl optionally substituted with a substituent selected from the group consisting of $C_{1-4}$alkyl, $C_{2-6}$alkenyl, $C_{3-7}$cycloalkyl, hydroxy, $C_{1-4}$alkoxy, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_4$alkyl, aryl$C_{1-4}$alkyl, amino$C_{2-6}$alkenyl, mono- or di($C_{1-4}$alkyl)amino$C_{2-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl;

$R_2$ is $C_{1-6}$alkyl, hydrogen, or $C_{2-6}$alkenyl; and $R_3$ is nitro, $C_{1-6}$alkyl optionally substituted with piperidinyl, pyrrolidinyl, $N(R_{4a}R_{4b})$, morpholinyl, pyridyl, cyano, or 4-($C_{1-4}$alkyl)-piperazin-1-yl.

16. A compound according to claim 1 wherein the compound is 5-isobutyl-1-(4-nitro-phenyl)-2-oxo-2,5-dihydro-1H-pyrido[3,2-b]indole-3-carbonitrile;

5-Allyl-1-(4-nitro-phenyl)-2-oxo-2,5-dihydro-1H-pyrido[3,2-b]indole-3-carbonitrile;

5-Butyl-1-(4-nitro-phenyl)-2-oxo-2,5-dihydro-1H-pyrido[3,2-b]indole-3-carbonitrile;

5-Ethyl-1-(4-nitro-phenyl)-2-oxo-2,5-dihydro-1H-pyrido[3,2-b]indole-3-carbonitrile;

5-(2-Morpholin-4-yl-ethyl)-1-(4-nitro-phenyl)-2-oxo-2,5-dihydro-1H-pyrido[3,2-b]indole-3-carbonitrile;

5-Methyl-1-(4-nitro-phenyl)-1,5-dihydro-pyrido[3,2-b]indol-2-one;

5-But-3-enyl-1-(4-nitro-phenyl)-2-oxo-2,5-dihydro-1H-pyrido[3,2-b]indole-3-carbonitrile;

1-(4-Nitro-phenyl)-2-oxo-5-(2-pyrrolidin-1-yl-ethyl)-2,5-dihydro-1H-pyrido[3,2-b]indole-3-carbonitrile;

1-(4-Nitro-phenyl)-2-oxo-5-(2-piperidin-1-yl-ethyl)-2,5-dihydro-1H-pyrido[3,2-b]indole-3-carbonitrile;

5-(3-Dimethylamino-propyl)-1-(4nitro-phenyl)-2-oxo-2,5-dihydro-1H-pyrido[3,2-b]-indole-3-carbonitrile;

3-Bromo-5-methyl-1-(4-nitro-phenyl)-1,5-dihydro-pyrido[3,2-b]indol-2-one

5-Methyl-1-(3-nitro-phenyl)-2-oxo-2,5-dihydro-1H-pyrido[3,2-b]indole-3-carbonitrile;

1-(4-Nitro-phenyl)-2-oxo-5-(3piperidin-1-propyl)-2,5-dihydro-1H-pyrido[3,2-b]indole-3-carbonitrile;

5-(4-Morpholin-4-yl-butyl)-1-(4-nitro-phenyl)-2-oxo-2,5-dihydro-1H-pyrido[3,2-b]indole-3-carbonitrile;

1-(4-Nitro-phenyl)-2-oxo-5-(4-pyrrolidin-1-yl-butyl)-2,5-dihydro-1H-pyrido[3,2-b]indole-3-carbonitrile;

5-[3-(4-Methyl-piperazin-1-yl)-propyl]-1-(4-nitropheny)-2-oxo-2,5-dihydro-1H-pyrido[3,2-b]indole-3-carbonitrile;

5-Cyanomethyl-1-(4-nitro-phenyl)-2-oxo-2,5-dihydro-1H-pyrido[3,2-b]indole-3-carbonitrile;

5-(3-Morpholin-4-yl-propyl)-1-(4-nitro-phenyl)-2-oxo-2,5-dihydro-1H-pyrido[3,2-b]-indole-3-carbonitrile;

1-(4-Nitro-phenyl)-2-oxo-5-(4-piperidin-1-yl-butyl)-2,5-dihydro-1H-pyrido[3,2-b]indole-3-carbonitrile;

5-(4Dimethylamino-butyl)-1-(4-nitro-phenyl)-2-oxo-2,5-dihydro-1H-pyrido[3,2-b]indole-3-carbonitrile;

1-(4-Nitro-phenyl)-2-oxo-5-pyridin-4-ylmethyl-2,5-dihydro-1H-pyrido[3,2-b]indole-3-carbonitrile;

3-(5-tert-Butyl-[1,2,4]oxadiazol-3-yl)-5-methyl-1-(4-nitro-phenyl)-1,5-dihydro -pyrido[3,2-b]indol-2-one; or 5-Methyl-1-(4nitro-phenyl)-3-(5-trifluoromethyl-[1,2,4]oxadiazol-3-yl)-1,5-dihydro -pyrido[3,2-b]indol-2-one; or a pharamaceutically acceptable salt or stereoisomer thereof.

17. A pharmaceutical composition, comprising an effective amount of at least one compound of formula (I) as defined in claim 1 and a pharmaceutically tolerable excipient.

\* \* \* \* \*

UNITED STATES PATENT AND TRADEMARK OFFICE
CERTIFICATE OF CORRECTION

PATENT NO. : 7,608,726 B2  Page 1 of 1
APPLICATION NO. : 10/535007
DATED : October 27, 2009
INVENTOR(S) : Kesteleyn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1038 days.

Signed and Sealed this

Fourteenth Day of December, 2010

David J. Kappos
*Director of the United States Patent and Trademark Office*